(12) United States Patent
Hammock et al.

(10) Patent No.: US 9,296,693 B2
(45) Date of Patent: Mar. 29, 2016

(54) ACYL PIPERIDINE INHIBITORS OF SOLUBLE EPOXIDE HYDROLASE

(75) Inventors: Bruce D. Hammock, Davis, CA (US); Tristan Rose, Orinda, CA (US); Christophe Morisseau, West Sacramento, CA (US); Kin Sing Lee, Davis, CA (US)

(73) Assignee: The Regents of the University of California, Oakland, CA (US)

(*) Notice: Subject to any disclaimer, the term of this patent is extended or adjusted under 35 U.S.C. 154(b) by 417 days.

(21) Appl. No.: 13/575,588

(22) PCT Filed: Jan. 28, 2011

(86) PCT No.: PCT/US2011/022901
§ 371 (c)(1),
(2), (4) Date: Feb. 12, 2013

(87) PCT Pub. No.: WO2012/054093
PCT Pub. Date: Apr. 26, 2012

(65) Prior Publication Data
US 2013/0143925 A1 Jun. 6, 2013

Related U.S. Application Data

(60) Provisional application No. 61/299,495, filed on Jan. 29, 2010.

(51) Int. Cl.
*C07D 211/58* (2006.01)
*C07D 211/96* (2006.01)
*C12Q 1/34* (2006.01)
*A61K 31/445* (2006.01)

(52) U.S. Cl.
CPC ............ *C07D 211/58* (2013.01); *A61K 31/445* (2013.01); *C07D 211/96* (2013.01); *C12Q 1/34* (2013.01)

(58) Field of Classification Search
CPC .. C07D 211/58; C07D 211/96; A61K 31/445; C12Q 1/34
USPC ...................... 514/329; 435/184, 18; 546/224
See application file for complete search history.

(56) References Cited

U.S. PATENT DOCUMENTS

| | | | |
|---|---|---|---|
| 3,587,060 A | 6/1971 | Quinn et al. |
| 3,703,537 A | 11/1972 | Richter et al. |
| 3,755,415 A | 8/1973 | Richter et al. |
| 4,252,954 A | 2/1981 | Abdulla et al. |
| 5,273,982 A | 12/1993 | Alig et al. |
| 5,314,902 A | 5/1994 | Tjoeng et al. |
| 5,445,956 A | 8/1995 | Hammock et al. |
| 5,492,918 A | 2/1996 | Wild et al. |
| 5,637,113 A | 6/1997 | Tartaglia et al. |
| 5,877,224 A | 3/1999 | Brocchini et al. |
| 5,962,455 A | 10/1999 | Blum et al. |
| 6,150,415 A | 11/2000 | Hammock et al. |
| 6,211,241 B1 | 4/2001 | Islam et al. |
| 6,287,285 B1 | 9/2001 | Michal et al. |
| 6,290,722 B1 | 9/2001 | Wang |
| 6,299,604 B1 | 10/2001 | Ragheb et al. |
| 6,322,847 B1 | 11/2001 | Zhong et al. |
| 6,329,395 B1 | 12/2001 | Dugar et al. |
| 6,335,029 B1 | 1/2002 | Kamath et al. |
| 6,344,358 B1 | 2/2002 | Matsuoka et al. |
| 6,387,900 B1 | 5/2002 | Pevarello et al. |
| 6,531,506 B1 | 3/2003 | Kroetz et al. |
| 6,613,572 B2 | 9/2003 | Matsuoka et al. |
| 6,693,202 B1 | 2/2004 | Aggen et al. |
| 6,710,043 B1 | 3/2004 | Yamada et al. |
| 8,188,289 B2 | 5/2012 | Hammock et al. |
| 2002/0090732 A1 | 7/2002 | Matsuoka et al. |
| 2004/0014745 A1 | 1/2004 | Yamada et al. |
| 2004/0054187 A1 | 3/2004 | Mammen et al. |
| 2004/0092487 A1 | 5/2004 | Kroetz et al. |
| 2004/0242637 A1 | 12/2004 | Hartman et al. |
| 2005/0026844 A1 | 2/2005 | Hammock et al. |
| 2007/0225283 A1 | 9/2007 | Hammock et al. |
| 2008/0221100 A1 | 9/2008 | Gless et al. |
| 2008/0227780 A1 | 9/2008 | Gless et al. |
| 2009/0197916 A1 | 8/2009 | Wang et al. |

FOREIGN PATENT DOCUMENTS

| | | |
|---|---|---|
| CA | 2 360 360 A1 | 7/2000 |
| DE | 123 466 A | 12/1976 |
| EP | 0 503 627 A1 | 9/1992 |
| EP | 1 031 564 A1 | 8/2000 |
| JP | 4-13666 A | 1/1992 |
| JP | 7-133224 A | 5/1995 |
| JP | 2001-158789 A | 6/2001 |
| JP | 2003-522120 A | 7/2003 |
| JP | 2004-002414 A | 1/2004 |

(Continued)

OTHER PUBLICATIONS

AN 2000: 473143, CAPLUS abstract of Jefferson et al., "Solid-phase synthesis of a heterocyclic ethylenediamine-derivatized library," J. Comb. Chem., 2(5):441-444 (2000) abstract only.
Arand, M. et al., "Sequence similarity of mammalian epoxide hydrolases to the bacterial haloalkane dehalogenase and other related proteins" FEBS Lett., 338:251-256 (1994).
Argiriadi, M.A. et al., "Binding of alkylurea inhibitors to epoxide hydrolase implicates active site tyrosines in substrate activation" J. Biol. Chem., 275:15265-15270 (2000).
Argiriadi, M.A. et al., "Detoxification of encironmental mutagens and carcinogens: structure, mechanism, and evolution of liver epoxide hydrolase" Proc. Natl. Acad. Sci. USA, 96:10637-10642 (1999).
Bardin, C. W. (ed.), *Current Therapy in Endocrinology and Metabolism*, 6th Edition, Mosby—Year Book, Inc., St. Louis, MO 1997.
Beetham, J. et al., "cDNA cloning and expression of a soluble epoxide hydrolase from human liver" Arch. Biochem. Biophys., 305(1):197-201 (1993).

(Continued)

*Primary Examiner* — Sarah Pihonak
*Assistant Examiner* — Jason A Deck
(74) *Attorney, Agent, or Firm* — DLA Piper LLP (US)

(57) ABSTRACT

Inhibitors of the soluble epoxide hydrolase (sEH) are provided that incorporate multiple pharmacophores and are useful in the treatment of diseases.

2 Claims, 6 Drawing Sheets

(56) References Cited

FOREIGN PATENT DOCUMENTS

| | | |
|---|---|---|
| RU | 2 208 608 C2 | 7/2003 |
| WO | WO 98/02435 | 1/1998 |
| WO | WO 99/07700 A1 | 2/1999 |
| WO | WO 99/09024 A1 | 2/1999 |
| WO | WO 00/42011 A1 | 7/2000 |
| WO | WO 00/48593 A1 | 8/2000 |
| WO | WO 00/72834 A2 | 12/2000 |
| WO | WO 00/72834 A3 | 12/2000 |
| WO | WO 00/76457 A2 | 12/2000 |
| WO | WO 00/76457 A3 | 12/2000 |
| WO | WO 01/42212 A1 | 6/2001 |
| WO | WO 02/14311 A2 | 2/2002 |
| WO | WO 02/14311 A3 | 2/2002 |
| WO | WO 03/009845 A1 | 2/2003 |
| WO | WO 03/061597 A2 | 7/2003 |
| WO | WO 03/061597 A3 | 7/2003 |
| WO | WO 03/070242 A1 | 8/2003 |
| WO | WO 03/070727 A1 | 8/2003 |
| WO | WO 03/076426 A2 | 9/2003 |
| WO | WO 03/076426 A3 | 9/2003 |
| WO | WO 03/082861 A2 | 10/2003 |
| WO | WO 03/082861 A3 | 10/2003 |
| WO | WO 03/097586 A1 | 11/2003 |
| WO | WO 03/097618 A1 | 11/2003 |
| WO | WO 2004/007459 A2 | 1/2004 |
| WO | WO 2004/007459 A3 | 1/2004 |
| WO | WO 2004/026836 A2 | 4/2004 |
| WO | WO 2004/026836 A3 | 4/2004 |
| WO | WO 2004/063181 A1 | 7/2004 |
| WO | WO 2004/064730 A2 | 8/2004 |
| WO | WO 2004/064730 A3 | 8/2004 |
| WO | WO 2004/089296 A2 | 10/2004 |
| WO | WO 2004/094381 A1 | 11/2004 |
| WO | WO 2004/111009 A1 | 12/2004 |
| WO | WO 2004/111031 A1 | 12/2004 |
| WO | WO 2005/014580 A1 | 2/2005 |
| WO | WO 2005/030209 A1 | 4/2005 |
| WO | WO 2005/037199 A2 | 4/2005 |
| WO | WO 2005/037199 A3 | 4/2005 |
| WO | WO 2005/089763 A1 | 9/2005 |
| WO | WO 2005/113511 A1 | 12/2005 |
| WO | WO 2006/009741 A1 | 1/2006 |
| WO | WO 2006/014136 A1 | 2/2006 |
| WO | WO 2006/014359 A2 | 2/2006 |
| WO | WO 2006/014359 A3 | 2/2006 |
| WO | WO 2006/016039 A1 | 2/2006 |
| WO | WO 2006/045119 A2 | 4/2006 |
| WO | WO 2008051873 A2 * | 5/2008 |
| WO | WO 2009/129501 A1 | 10/2009 |
| WO | WO 2009/129508 A1 | 10/2009 |

OTHER PUBLICATIONS

Beetham, J. et al., "Gene evolution of epoxide hydrolases and recommended nomenclature" DNA Cell Biol., 14(1):61-71 (1995).
Campbell, W.B., "New role for epoxyeicosatrienoic acids as anti-inflammatory mediators" Trends Pharmacol. Sci., 21:125-127 (2000).
Capdevila, J.H. et al., "Cytochrome P450 and arachidonic acid bioactivation: molecular and functional properties of the arachidonate monooxygenase" J. Lipid. Res., 41:163-181 (2000).
Carroll, M.A. et al., "A new class of lipid mediators: cytochrome P450 arachidonate metabolites" Thorax, 55:S13-16 (2000).
CAS Accession No. 71:18417; Accessed Dec. 12, 2006.
Chiasson, J. et al., "The efficacy of acarbose in the treatment of patients with non-insulin-dependent diabetes mellitus" Ann. Intern. Med., 121:928-935 (1994).
Coniff, R. et al., "Acarbose: a review of US clinical experience" Clin. Ther., 19:16-26 (1997).
Coniff, R. et al., "Multicenter, placebo-controlled trial comparing acarbose (BAY g5421) with placebo, tolbutamide, and tolbutamide-plus-acarbose in non-insulin-dependent diabetes mellitus" Am. J. Med., 98:443-451 (1995).

Defronzo, R. et al. (eds.), "Introduction" Diabetes Reviews, 5(4):293 (1997).
Dudda, A. et al., "Lipid oxidation products in ischemic porcine heart tissue" Chem. Phys. Lipids, 82:39-51 (1996).
Edwards et al., "Nonpeptidic Inhibitors of Human Neurophil Elastase. 7. Design, Synthesis, and in Vitro Activity of a Series of Pyridopyrimidine Trifluoromethyl Ketones," J. Med. Chem, 1996, 39, 1112-1124.
Fang, X., et al., "Effect of soluble epoxide hydrolase inhibition on epoxyeicosatrienoic acid metabolism in human blood vessels" Am. J. Physiol. Heart Circ. Physiol. 287:H2412-H2420 (2004).
Fisslthaler, B. et al., "Cytochrome P450 2C is an EDHF synthase in coronary arteries" Nature, 401:493-497 (1999).
Fourie et al., International Journal of Pharamceutics, vol. 279, Issues 1-2, Jul. 26, 2004, pp. 59-66.
Fretland, A.J. et al., "Epoxide hyrolases: biochemistry and molecular biology" Chem. Biol. Intereract., 129:41-59 (2000).
Fukushima, A. et al., "Cardiovascular effects of leukotoxin (9,10-epoxy-12-octadecenoate) and free fatty acids in dogs" Cardiovasc. Res., 22:213-218 (1988).
Gibson, G.G. and Skett, P., *Introduction to Drug Metabolism*, Second Ed., Chapman and Hall, New York pp. 199-210 (1994).
Goosen et al. "Physicochemical Characterization and Solubility Analysis of Thalidomide and its N-Alkyl Analogs," Pharmaceutical Research, Jan. 2002, vol. 19, No. 1, pp. 13-19.
Grant, D. et al., "Molecular cloning and expression of murine liver soluble epoxide hydrolase" J. Biol. Chem., 268(23):17628-17633 (1993).
Haffner, S., "Management of dyslipidemia in adults with diabetes" Diabetes Care, 21:160-178 (1998).
Hammock, B.D. et al., "Chapter 3.18: Epoxide Hyrolases" in *Comprehensive Toxicology*. Oxford: Pergamon Press pp. 283-305 (1977).
Honig and Ingram, "Chronic Bronchitis, Emphysema, and Airways Obstruction" in *Harrison's Principles of Internal Medicine*, (Fauci et al., Eds.), 14th Ed., McGraw-Hill, New York, pp. 1451-1460 (1998).
Hwang, S.H. et al. "Orally Bioavailable Potent Soluble Epoxide Hydrolase Inhibitors," 2007, *Journal of Medicinal Chemistry*, pp. A-P.
International Search Report mailed on Jul. 30, 2007, for PCT Application No. PCT/US2007/006412 filed on Mar. 13, 2007, ten pages.
Ishizaki, T. et al., "Endothelin-1 potentiates leukotoxin-induced edematous lung injury" J. Appl. Physiol., 79:1106-1611 (1995).
Ishizaki, T. et al., "Leukotoxin, 9,10-epoxy-12-octadecenoate causes pulmonary vasodilation in rats" Am. J. Physiol., 268:L123-128 (1995).
Ishizaki, T. et al., "Leukotoxin, 9,10-epoxy-12-octadecenoate causes edematous lung injury via activation of vascular nitric oxide synthase" Am. J. Physiol., 269:L65-70 (1995).
Iwamoto, Y. et al., "Effect of combination therapy of troglitazone and sulphonylureas in patients with type 2 diabetes who were poorly controlled by sulphonylurea therapy alone" Diabet. Med., 13:365-370 (1996).
Kim, I-H. et al. "Design, Synthesis, and Biological Activity of 1,3-Disubstituted Ureas as Potent Inhibitors of the Soluble Epoxide Hydrolase of Increased Water Solubility," 2004, *Journal of Medicinal Chemistry*, vol. 47, No. 8, pp. 2110-2122.
Kricheldorf, H.R. et al. "Polykondensation von N-Aryloxycarbonyl-w-aminocarbonsäuren und N-Phenoxycarbonyldipeptiden," 1975, *Die Angewandte Makromolekulare Chemie*, vol. 45, pp. 119-137.
Kwiterovich, P., "State-of-the-art update and review: clinical trials of lipid-lowering agents" Am. J. Cardiol., 82(12A):3U-17U (1998).
Mahler, R. et al., "Type 2 diabetes mellitus: update on diagnosis, pathophysiology, and treatment" J. Clin. Endocrinol. Metab., 84:1165-71 (1999).
McElroy, N.R. et al. "QSAR and Classification of Murine and Human Soluble Epoxide Hydrolase Inhibition by Urea-Like Compounds," 2003, *Journal of Medicinal Chemistry*, vol. 46, No. 6, pp. 1066-1080; pp. 1-39 of supporting information from http://pubs.acs.org/subscribe/journals/jmcmar/suppinfo/jm020269o/jm020269o_s.pdf.
Migawa et al., "A Solid-Phase Synthesis of N,N'-Disubstituted Ureas and Perhydroimidazo[1,5-*a*]pyrazines via the Curtius Rearrangement," Organic Letters, 2000, 2, pp. 3309-3311.

(56) References Cited

OTHER PUBLICATIONS

Moghaddam, M.F. et al., "Bioactivation of leukotoxins to their toxic diols by epoxide hydrolase" Nat. Med., 3:562-567 (1997).
Morisseau, C. et al. "Potent Urea and Carbamate Inhibitors of Soluble Epoxide Hydrolases," Aug. 1999, *P.N.A.S. USA*, vol. 96, pp. 8849-8854.
Morisseau, C. et al. "Structural Refinement of Inhibitors of Urea-Based Soluble Epoxide Hydrolases," *Biochemical Pharmacology*, 2002, vol. 63, pp. 1599-1608.
Morisseau, C., et al., "Inhibition of microsomal epoxide hydrolases by ureas, amides, and amines" Chem. Res. Toxicol. 14:409-415 (2001).
Nakagawa, Y., et al., "3-D QSAR analysis of inhibition of murine soluble epoxide hydrolase (MsEH) by benzoylureas, arylureas, and their analogues" Bioorg. Med. Chem. 8:2663-2673 (2000).
Newman, J.W. et al., "Evaluation of fish models of soluble epoxide hydrolase inhibition" Environ. Health Perspect., 109:61-66 (2001).
Node, K. et al., "Anti-inflammatory properties of cytochrome P450 epoxygenase-derived eicosanoids" Science, 285:1276-1279 (1999).
Oesch, F. et al., "Mammalian epoxide hydrases: inducible enzymes catalyzing the inactivation of carcinogenic and cytotoxic metabolites derived from aromatic and olefinic compounds" Xenobiotica, 3:305-340 (1973).
Oltman, C.L. et al., "Epoxyeicosatrienoic acids and dihydroxyeicosatrienoic acids are potent vasodilators in the canine coronary microcirculation" Circ Res., 83:932-939 (1998).
Ozawa, T. et al., "Existence of leukotoxin 9,10-epoxy-12-octadecenoate in lung lavages from rats breathing pure oxygen and from patients with the adult respiratory distress syndrome" Am. Rev. Respir. Dis., 137:535-540 (1988).
Partial Supplementary European Search Report completed on Aug. 31, 2006, for EP Application No. 04 75 8831, seven pages.
Rautio et al., "Piperazinylalkyl prodrugs of naproxen improve in vitro skin permeation," Eur. J. Pharm. Sci, 2000, 11, pp. 157-163.
Reynolds, H.Y., "Interstitial lung diseases" in *Harrison's Principles of Internal Medicine*, (Fauci et al., Eds.), 14th Ed., McGraw-Hill, New York, pp. 1460-1466 (1998).
Sakai, T. et al., "Leukotoxin, 9,10-epoxy-12-octadecenoate inhibits mitochondrial respiration of isolated perfused rat lung" Am. J. Physiol., 269:L326-331 (1995).
Sinal, C.J. et al., "Targeted disruption of soluble epoxide hydrolase reveals a role in blood pressure regulation" J. Biol. Chem., 275:40504-405010 (2000).
Skwarski et al., Acta Poloniae Pharmaceutica, 1988, 45, pp. 391-394.
Speizer, "Environmental Lung Diseases," *Harrison's Principles of Internal Medicine*, (Fauci et al., Eds.), 14th Ed., 1998, McGraw-Hill, New York, pp. 1429-1436.

Turner, N. et al., "Insulin resistance, impaired glucose tolerance and non-insulin-dependent diabetes, pathologic mechanisms and treatment: Current status and therapeutics possibilities" Prog. Drug Res., 51:33-94 (1998).
United Kingdom Prospective Diabetes Study Group, "UKPDS 28: a randomized trial of efficacy of early addition of metformin in sulfonylurea-treated type 2 diabetes", Diabetes Care, 21: 87-92 (1998).
Walter, E. et al., "Transepithelial transport properties of peptidomimetic thrombin inhibitors in monolayers of a human intestinal cell line (Caco-2) and their correlation to in vivo data" Pharm. Res., 12: 360-365 (1995).
Watanabe, K. et al., "Studies on intestinal absorption of sulpiride (2): transepithelial transport of sulpiride across the human intestinal cell line caco-2" Biol. Pharm. Bull., 25:1345-1350 (2002).
Watanabe, T. et al. "Rapid Determination of Soluble Epoxide Hydrolase Inhibitors in Rat Hepatic Microsomes by High-Performance Liquid Chromatography with Electrospray Tandem Mass Spectrometry," 2001, *Analytical Biochemistry*, vol. 299, pp. 227-234.
Watanabe, T., et al., "In vitro metabolism of the mammalian soluble epoxide hydrolase inhibitor, 1-cyclohexyl-3-dodecyl-urea" Drug Metab. Dispos. 31(7):846-853 (2003).
Weintraub, N.L. et al., "Epoxide hydrolases regulate epoxyeicosatrienoic acid incorporation into coronary endothelial phospholipids" Am. J. Physiol., 277:H2098-2108 (1992).
Yamada, T. et al. "Biochemical Evidence for the Involvement of Tyrosine in Epoxide Activation During the Catalytic Cycle of Epoxide Hydrolase," Jul. 28, 2000, *The Journal of Biological Chemistry*, vol. 275, No. 30, pp. 23082-23088.
Yu, Z. et al., "Soluble epoxide hydrolase regulates hydrolysis of vasoactive epoxyeicosatrienoic acids" Circ. Res., 87:992-998 (2000).
Zeldin, D.C., et al., "Regio- and enantiofacial selectivity of epoxyeicosatrienoic acid hydration by cytosolic epoxide hydrolase" J. Biol. Chem., 268:6402-6407 (1993).
Zhao, X., et al., "Soluble epoxide hydrolase inhibition protects the kidney from hypertension-induced damage" J. Am. Soc. Nephrol. 15:1244-1253 (2004).
Zheng, J. et al., "Leukotoxin-Diol: a putative toxic mediator involved in acute respiratory distress syndrome" Am. J. Respir. Cell Mol. Biol., 25:434-438 (2001).
Written Opinion of the International Searching Authority dated Jun. 8, 2012, issued in related International Patent Application No. PCT/US2011/022901, filed Jan. 28, 2011.
Rose, et al., "1-Aryl-3-(1-acylpiperidin-4-yl)urea Inhibitors of Human and Murine Soluble Epoxide Hydrolase: Structure Activity Relationships, Pharmacokinetics, and Reduction of Inflammatory Pain," 2010, J. Med. Chem. 2010, 53, pp. 7067-7075.
Extended European Search Report regarding EP 11 83 4764, Dec. 17, 2014.

* cited by examiner

Scheme 1. Synthesis of *N*-propioyl piperidine analogues

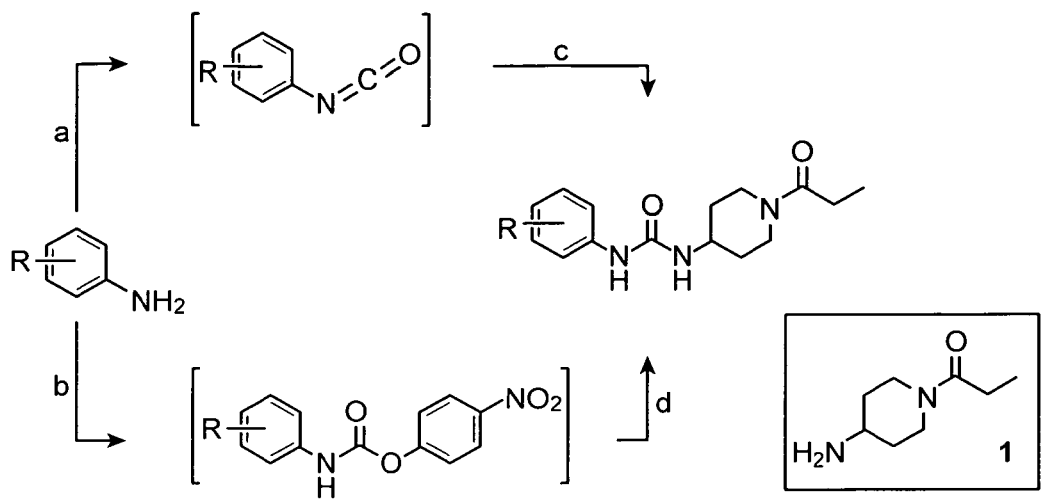

Reaction conditions: (a) triphosgene, DCM, sat. NaHCO$_3$ or 1N NaOH, sat. NaCl, 0 °C, 10min; (b) 4-nitrophenyl chloroformate, Et$_3$N, THF, 0 to 50 °C, 1-3h; (c) 1, THF, 0 °C to rt, 1-24h; (d) 1, DMF, 70 °C, 4h.

Scheme 2. Synthesis of *N*-acyl and *N*-sulfonyl piperidine analogues

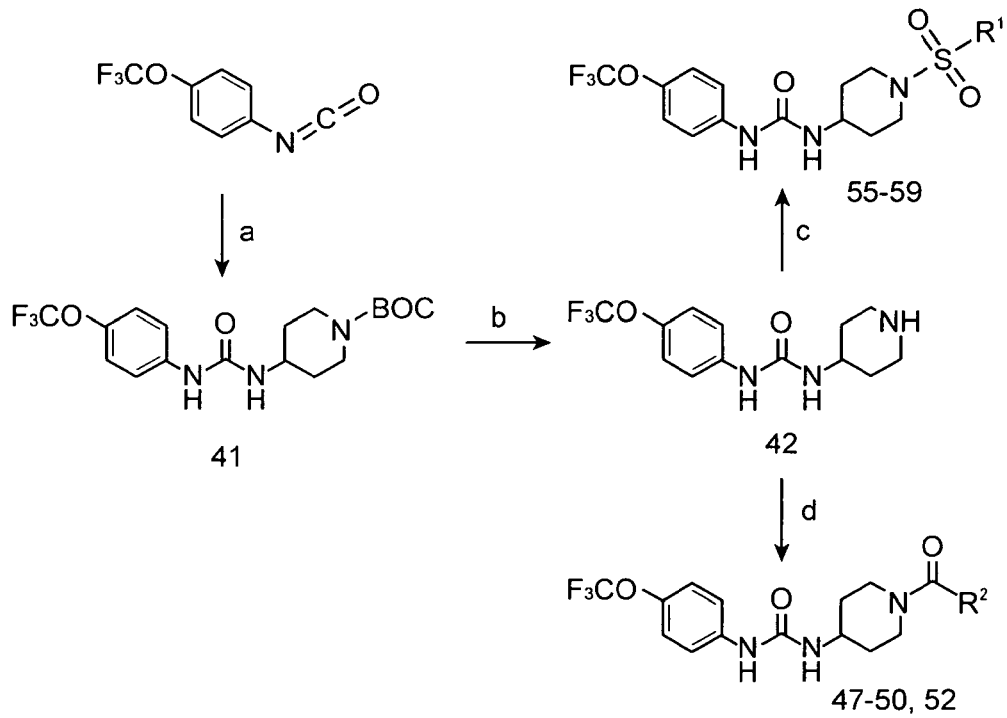

Reagents and conditions: (a) 1-BOC-4-aminopiperidine, THF, 0 °C to rt, 12h; (b) 1N HCl in MeOH, reflux, 3h; (c) R$^2$SO$_2$Cl, Et$_3$N, THF, 0 °C to rt, 12h; (d) EDCI, R$^1$COOH, DMAP, DCM, rt, 12-24h.

FIG. 5

ACYL PIPERIDINE INHIBITORS OF SOLUBLE EPOXIDE HYDROLASE

CROSS-REFERENCE TO RELATED APPLICATIONS

This application is the U.S. National Stage entry under §371 of International Application No. PCT/US2011/022901, filed Jan. 28, 2011, which claims the benefit of U.S. Provisional Application No. 61/299,495, filed Jan. 29, 2010, which are incorporated in their entirety herein for all purposes.

STATEMENT AS TO RIGHTS TO INVENTIONS MADE UNDER FEDERALLY SPONSORED RESEARCH OR DEVELOPMENT

This invention was made with Government support under Grant Nos. R01 ES002710, P42 ES004699 and R01 ES013933, awarded by the NIEHS. The Government has certain rights in this invention.

BACKGROUND OF THE INVENTION

Epoxide hydrolases (EHs, EC 3.3.2.3) catalyze the hydrolysis of epoxides or arene oxides to their corresponding diols by the addition of water (see, Oesch, F., et al., *Xenobiotica* 1973, 3, 305-340). Some EHs play an important role in the metabolism of a variety of compounds including hormones, chemotherapeutic drugs, carcinogens, environmental pollutants, mycotoxins, and other harmful foreign compounds.

There are two well-studied EHs, microsomal epoxide hydrolase (mEH) and soluble epoxide hydrolase (sEH). These enzymes are very distantly related, have different subcellular localization, and have different but partially overlapping substrate selectivities. The soluble and microsomal EH forms are known to complement each other in degrading some plant natural products (see, Hammock, B. D., et al., COMPREHENSIVE TOXICOLOGY. Oxford: Pergamon Press 1977, 283-305 and Fretland, A. J., et al., *Chem. Biol. Intereract* 2000, 129, 41-59).

The major role of the sEH is in the metabolism of lipid epoxides including the metabolism of arachidonic acid (see, Zeldin, D. C., et al., *J. Biol. Chem.* 1993, 268, 6402-6407), linoleic acid (see, Moghaddam, M. F., et al., *Nat. Med.* 1997, 3, 562-567) acid, some of which are endogenous chemical mediators (see, Carroll, M. A., et al., *Thorax* 2000, 55, S13-16). Epoxides of arachidonic acid (epoxyeicosatrienoic acids or EETs) and other lipid epoxides and diols are known effectors of blood pressure (see, Capdevila, J. H., et al., *J. Lipid. Res.* 2000, 41, 163-181), and modulators of vascular permeability (see, Oltman, C. L., et al., *Circ Res.* 1998, 83, 932-939). The vasodilatory properties of EETs are associated with an increased open-state probability of calcium-activated potassium channels leading to hyperpolarization of the vascular smooth muscle (see Fisslthaler, B., et al., *Nature* 1999, 401, 493-497). Hydrolysis of the arachidonate epoxides by sEH diminishes this activity (see, Capdevila, J. H., et al., *J. Lipid. Res.* 2000, 41, 163-181). sEH hydrolysis of EETs also regulates their incorporation into coronary endothelial phospholipids, suggesting a regulation of endothelial function by sEH (see, Weintraub, N. L., et al., *Am. J. Physiol.* 1992, 277, H2098-2108). It has recently been shown that treatment of spontaneous hypertensive rats (SHRs) with selective sEH inhibitors significantly reduces their blood pressure (see, Yu, Z., et al., *Circ. Res.* 2000, 87, 992-998). In addition, it was claimed that male knockout sEH mice have significantly lower blood pressure than wild-type mice (see Sinal, C. J., et al., *J. Biol. Chem.* 2000, 275, 40504-405010), however subsequent studies demonstrated with back breeding into C57b mice that 20-HETE levels increased compensating for the increase in plasma EETs (see, Luria, A. et al., *J. Biol. Chem.* 2007, 282:2891-2898.

The EETs have also demonstrated anti-inflammatory properties in endothelial cells (see, Node, K., et al., *Science* 1999, 285, 1276-1279 and Campbell, W. B. *Trends Pharmacol. Sci.* 2000, 21, 125-127). In contrast, diols derived from epoxylinoleate (leukotoxin) perturb membrane permeability and calcium homeostasis (see, Moghaddam, M. F., et al., *Nat. Med.* 1997, 3, 562-567), which results in inflammation that is modulated by nitric oxide synthase and endothelin-1 (see, Ishizaki, T., et al., *Am. J. Physiol.* 1995, 269, L65-70 and Ishizaki, T., et al., *J. Appl. Physiol.* 1995, 79, 1106-1611). Micromolar concentrations of leukotoxin reported in association with inflammation and hypoxia (see, Dudda, A., et al., *Chem. Phys. Lipids* 1996, 82, 39-51), depress mitochondrial respiration in vitro (see, Sakai, T., et al., *Am. J. Physiol.* 1995, 269, L326-331), and cause mammalian cardiopulmonary toxicity in vivo (see, Ishizaki, T., et al., *Am. J. Physiol.* 1995, 269, L65-70; Fukushima, A., et al., *Cardiovasc. Res.* 1988, 22, 213-218; and Ishizaki, T., et al., *Am. J. Physiol.* 1995, 268, L123-128). Leukotoxin toxicity presents symptoms suggestive of multiple organ failure and acute respiratory distress syndrome (ARDS) (see, Ozawa, T. et al., *Am. Rev. Respir. Dis.* 1988, 137, 535-540). In both cellular and organismal models, leukotoxin-mediated toxicity is dependent upon epoxide hydrolysis (see, Moghaddam, M. F., et al., *Nat. Med.* 1997, 3, 562-567; Morisseau, C., et al., *Proc. Natl. Acad. Sci. USA* 1999, 96, 8849-8854; and Zheng, J., et al., *Am. J. Respir. Cell Mol. Biol.* 2001, 25, 434-438), suggesting a role for sEH in the regulation of inflammation and vascular permeability. The bioactivity of these epoxy-fatty acids suggests that inhibition of vicinal-dihydroxy-lipid biosynthesis may have therapeutic value, making sEH a promising pharmacological target.

Recently, 1,3-disubstituted ureas, carbamates, and amides have been reported as new potent and stable inhibitors of sEH See, U.S. Pat. No. 6,150,415. Compounds 192 and 686 are representative structures for this type of inhibitors (FIG. 1, therein). These compounds are competitive tight-binding inhibitors with nanomolar $K_i$ values that interact stoichiometrically with purified recombinant sEH (see, Morisseau, C., et al., *Proc. Natl. Acad. Sci. USA* 1999, 96, 8849-8854). Based on the X-ray crystal structure, the urea inhibitors were shown to establish hydrogen bonds and to form salt bridges between the urea function of the inhibitor and residues of the sEH active site, mimicking features encountered in the reaction coordinate of epoxide ring opening by this enzyme (see, Argiriadi, M. A., et al., *Proc. Natl. Acad. Sci. USA* 1999, 96, 10637-10642 and Argiriadi, M. A., et al., *J. Biol. Chem.* 2000, 275, 15265-15270). These inhibitors efficiently reduced epoxide hydrolysis in several in vitro and in vivo models (see, Yu, Z., et al., *Circ. Res.* 2000, 87, 992-998; Morisseau, C., et al., *Proc. Natl. Acad. Sci. USA* 1999, 96, 8849-8854; and Newman, J. W., et al., *Environ. Health Perspect.* 2001, 109, 61-66). Despite the high activity associated with these inhibitors, there exists a need for compounds possessing similar or increased activities, preferably with improved solubility and/or pharmacokinetic properties to facilitate formulation and delivery.

The present invention provides such compounds along with methods for their use and compositions that contain them.

BRIEF SUMMARY OF THE INVENTION

In one aspect, the present invention provide a compound of formula II:

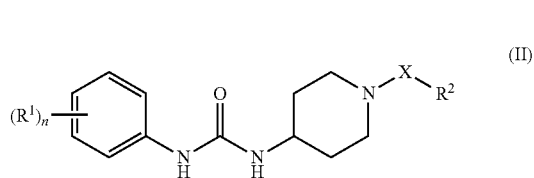

wherein each $R^1$ of formula II is independently H, halogen, $C_{1-6}$ alkyl, $C_{1-6}$ alkoxy, $C_{1-6}$ haloalkyl, $C_{1-6}$ haloalkoxy, —O-aryl, heterocycloalkyl having 5-6 ring members and at least 1 N heteroatom and 10 heteroatom as ring members, —OH, —NO$_2$ or —C(O)OR$^3$, wherein at least 1 $R^1$ is other than H. Alternatively, two $R^1$ groups on adjacent carbons are joined to form a 5-6 membered heterocycloalkyl ring having from 1-20 heteroatoms as ring members. Radical X of formula II is —C(O)— or —S(O)$_2$—. Radical $R^2$ of formula II is $C_{1-6}$ alkyl, $C_{1-6}$ haloalkyl, cycloalkyl having 3-6 ring members, $C_{1-6}$ alkyl-heterocycloalkyl having from 5-6 ring members and at least 2 N heteroatoms as ring members and substituted with a member benzyl or —C(O)—C$_{1-6}$ alkyl, phenyl optionally substituted with OH, or $C_{0-6}$ alkyl-heteroaryl having 5-6 ring members and at least 1 N heteroatom as a ring member and optionally substituted with halogen. Radical $R^3$ of formula II is H or $C_{1-6}$ alkyl. Subscript n of formula II is an integer from 1 to 5. When $R^1$ is $C_{1-6}$ haloalkoxy, then $R^2$ is $C_{2-6}$ alkyl, $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member benzyl or —C(O)—C$_{1-6}$ alkyl, phenyl optionally substituted with OH, or $C_{0-6}$ alkyl-heteroaryl having 5-6 ring members and at least 1 N heteroatom as a ring member and optionally substituted with halogen. The salts and isomers of the compounds of formula II are also encompassed by the present invention.

In another aspect, the present invention provides a compound having formula I:

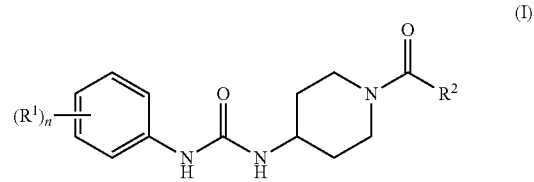

wherein each $R^1$ of formula I is H, halogen, $C_{1-6}$ alkyl, $C_{1-6}$ alkoxy, $C_{1-6}$ haloalkyl, $C_{1-6}$ haloalkoxy, —O-aryl, heterocycloalkyl having 5-6 ring members and at least 1 N heteroatom and 10 heteroatom as ring members, —OH, —NO$_2$ or —C(O)OR$^3$, wherein at least 1 $R^1$ is other than H. Alternatively, two $R^1$ groups on adjacent carbons are joined to form a 5-6 membered heterocycloalkyl ring having from 1-20 heteroatoms as ring members. $R^2$ of formula I is $C_{1-6}$ alkyl and $R^3$ is H or $C_{1-6}$ alkyl. Subscript n of formula I is an integer from 1 to 5. When $R^1$ of formula I is $C_{1-6}$ haloalkoxy, then $R^2$ is $C_{2-6}$ alkyl. The salts and isomers of the compounds of formula I are also encompassed by the present invention.

In another aspect, the present invention provides a compound having formula II:

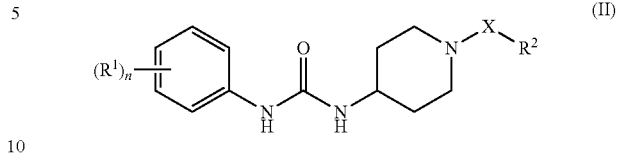

wherein $R^1$ of formula II is $C_{1-6}$ haloalkyl or $C_{1-6}$ haloalkoxy and X is —C(O)— or —S(O)$_2$—. Radical $R^2$ of formula II is $C_{2-6}$ alkyl, $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with benzyl or —C(O)—C$_{1-6}$ alkyl, phenyl optionally substituted with OH, or $C_{0-6}$ alkyl-heteroaryl having 5-6 ring members and at least 1 N heteroatom as a ring member and optionally substituted with halogen. The salts and isomers of the compounds of formula II are also encompassed by the present invention.

In yet another aspect, the present invention provides pharmaceutical compositions having a compound of the present invention and a pharmaceutically acceptable excipient.

In still another aspect, the present invention provides a method for inhibiting a soluble epoxide hydrolase, the method including contacting the soluble epoxide hydrolase with an inhibiting amount of a compound of the present invention.

In still yet another aspect, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said sEH.

BRIEF DESCRIPTION OF THE DRAWINGS

FIG. 5 shows Schemes 1 and 2 for the preparation of the compounds of the present invention.

DETAILED DESCRIPTION OF THE INVENTION

I. Abbreviations and Definitions

Figure 1:
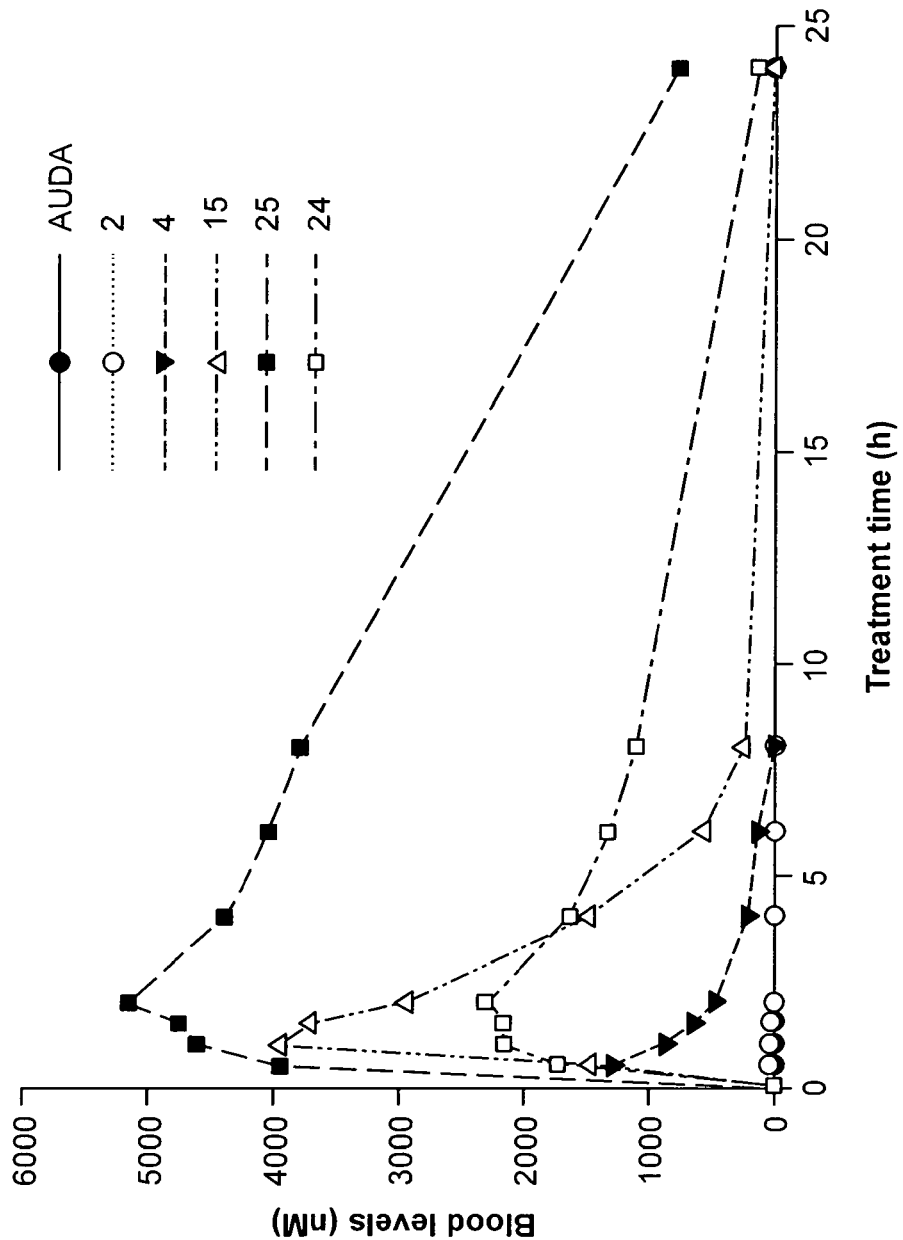
FIG. 1 shows the relative blood pharmacokinetics for AUDA and compounds 2, 4, 15, 24 and 25.
Figure 2:
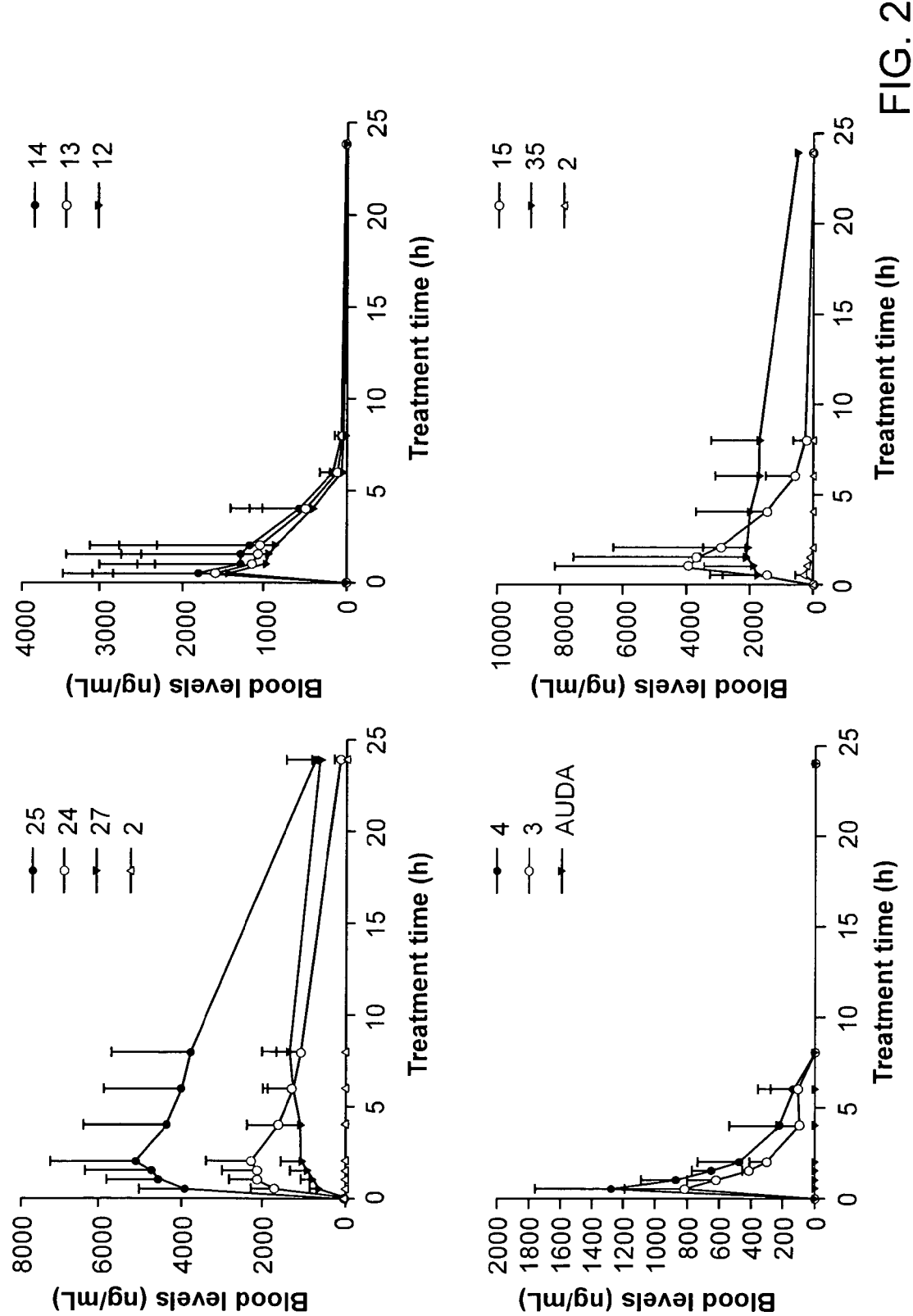
FIG. 2 shows blood pharmacokinetics profiles of compounds AUDA, 2, 3, 4, 12, 13, 14, 15, 24, 25, 27, and 35.
Figure 3:
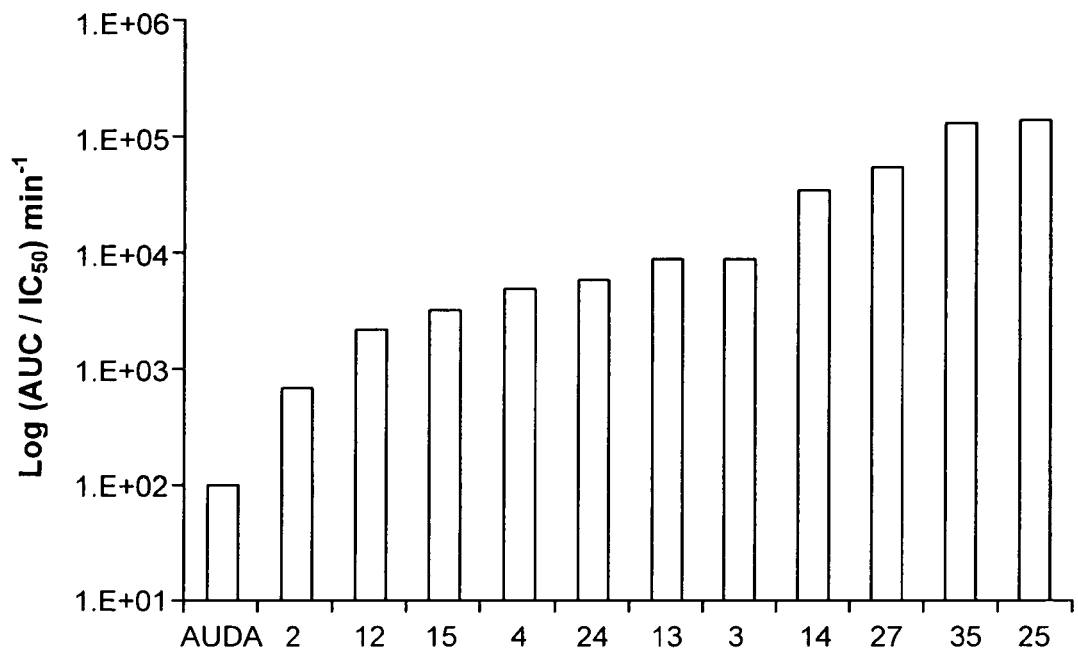
FIG. 3 shows in vivo exposure (estimated as area under the curve from FIG. 1, Table 5) as a function of potency (−log IC$_{50}$) on the homogenous, recombinant human sEH (IC$_{50}$ from Table 7).
Figure 4:
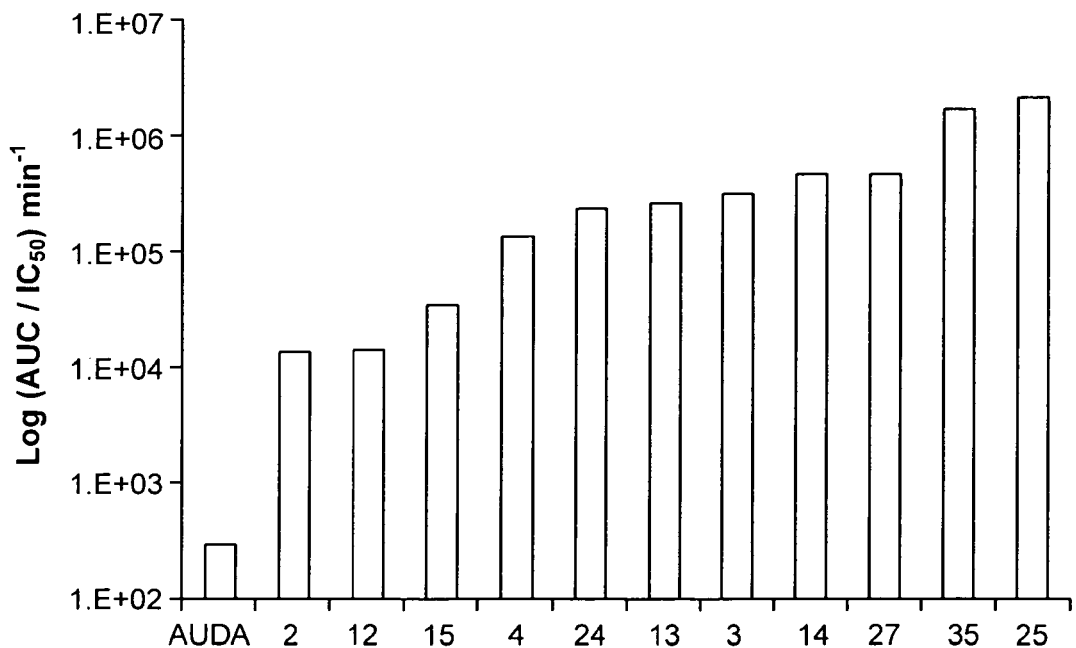
FIG. 4 shows in vivo exposure (estimated as area under the curve from FIG. 1, Table 5) as a function of potency (−log IC$_{50}$) on the homogenous, recombinant murine sEH (IC$_{50}$ from Table 7).
Figure 6:
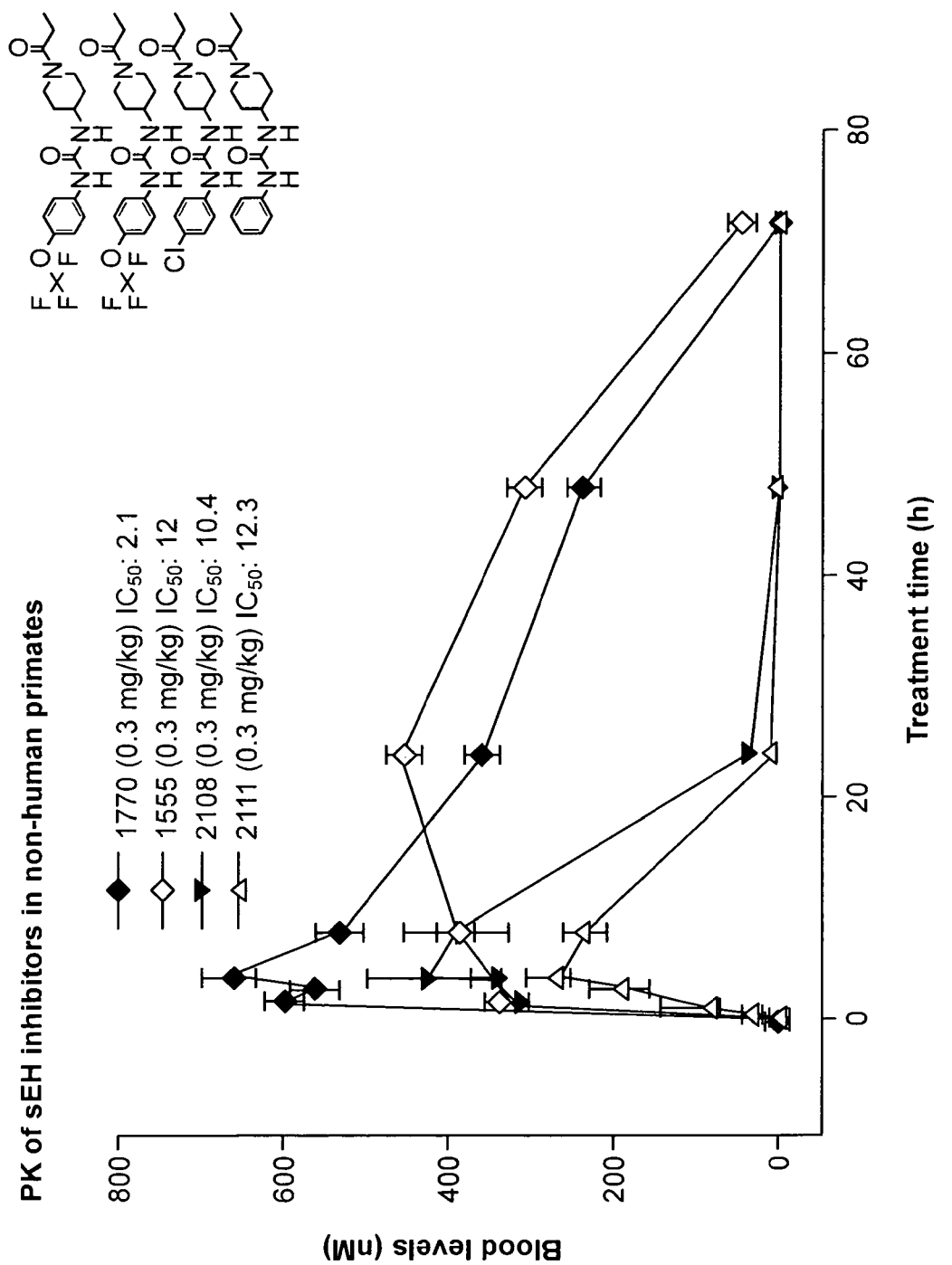
FIG. 6 shows pharmacokinetic data for selected compounds of the present invention in non-human primates.
Figure 7:
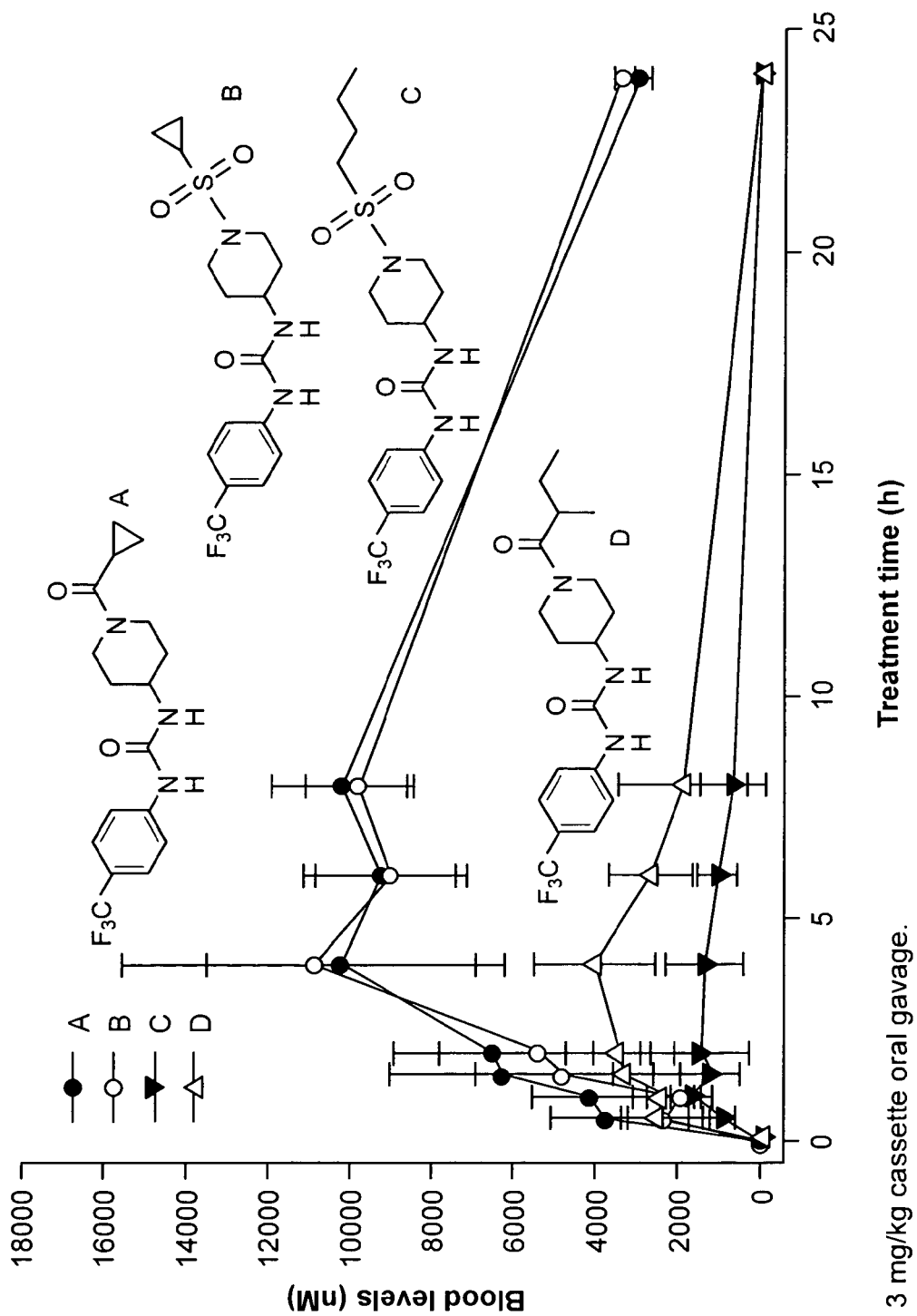
FIG. 7 shows blood pharmacokinetics profiles of compounds 61 (A), 70 (B), 69 (C) and 64 (D).

"cis-Epoxyeicosatrienoic acids" ("EETs") are biomediators synthesized by cytochrome P450 epoxygenases.

"Epoxide hydrolases" ("EH;" EC 3.3.2.3) are enzymes in the alpha/beta hydrolase fold family that add water to 3 membered cyclic ethers termed epoxides.

"Soluble epoxide hydrolase" ("sEH") is an enzyme which in endothelial, smooth muscle and other cell types converts EETs to dihydroxy derivatives called dihydroxyeicosatrienoic acids ("DHETs"). The cloning and sequence of the murine sEH is set forth in Grant et al., *J. Biol. Chem.* 268(23): 17628-17633 (1993). The cloning, sequence, and accession numbers of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., *DNA Cell Biol.* 14(1):61-71 (1995). Soluble epoxide hydrolase represents a single highly conserved gene product with over 90% homology between rodent and human (Arand et al., *FEBS Lett.,* 338:251-256 (1994)).

As used herein, the terms "treat", "treating" and "treatement" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

The term "compound" as used herein is intended to encompass not only the specified molecular entity but also its pharmaceutically acceptable, pharmacologically active derivatives, including, but not limited to, salts, prodrug conjugates such as esters and amides, metabolites, hydrates, solvates and the like.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "sEH-mediated disease or condition" and the like refers to a disease or condition characterized by less than or greater than normal, sEH activity. A sEH-mediated disease or condition is one in which modulation of sEH results in some effect on the underlying condition or disease (e.g., a sEH inhibitor or antagonist results in some improvement in patient well-being in at least some patients).

"Parenchyma" refers to the tissue characteristic of an organ, as distinguished from associated connective or supporting tissues.

"Chronic Obstructive Pulmonary Disease" or "COPD" is also sometimes known as "chronic obstructive airway disease", "chronic obstructive lung disease", and "chronic airways disease." COPD is generally defined as a disorder characterized by reduced maximal expiratory flow and slow forced emptying of the lungs. COPD is considered to encompass two related conditions, emphysema and chronic bronchitis. COPD can be diagnosed by the general practitioner using art recognized techniques, such as the patient's forced vital capacity ("FVC"), the maximum volume of air that can be forcibly expelled after a maximal inhalation. In the offices of general practitioners, the FVC is typically approximated by a 6 second maximal exhalation through a spirometer. The definition, diagnosis and treatment of COPD, emphysema, and chronic bronchitis are well known in the art and discussed in detail by, for example, Honig and Ingram, in Harrison's Principles of Internal Medicine, (Fauci et al., Eds.), 14th Ed., 1998, McGraw-Hill, New York, pp. 1451-1460 (hereafter, "Harrison's Principles of Internal Medicine").

"Emphysema" is a disease of the lungs characterized by permanent destructive enlargement of the airspaces distal to the terminal bronchioles without obvious fibrosis.

"Chronic bronchitis" is a disease of the lungs characterized by chronic bronchial secretions which last for most days of a month, for three months a year, for two years.

As the names imply, "obstructive pulmonary disease" and "obstructive lung disease" refer to obstructive diseases, as opposed to restrictive diseases. These diseases particularly include COPD, bronchial asthma and small airway disease.

"Small airway disease." There is a distinct minority of patients whose airflow obstruction is due, solely or predominantly to involvement of the small airways. These are defined as airways less than 2 mm in diameter and correspond to small cartilaginous bronchi, terminal bronchioles and respiratory bronchioles. Small airway disease (SAD) represents luminal obstruction by inflammatory and fibrotic changes that increase airway resistance. The obstruction may be transient or permanent.

The "interstitial lung diseases (ILDs)" are a group of conditions involving the alveolar walls, perialveolar tissues, and contiguous supporting structures. As discussed on the website of the American Lung Association, the tissue between the air sacs of the lung is the interstitium, and this is the tissue affected by fibrosis in the disease. Persons with the disease have difficulty breathing in because of the stiffness of the lung tissue but, in contrast to persons with obstructive lung disease, have no difficulty breathing out. The definition, diagnosis and treatment of interstitial lung diseases are well known in the art and discussed in detail by, for example, Reynolds, H. Y., in Harrison's Principles of Internal Medicine, supra, at pp. 1460-1466. Reynolds notes that, while ILDs have various initiating events, the immunopathological responses of lung tissue are limited and the ILDs therefore have common features.

"Idiopathic pulmonary fibrosis," or "IPF," is considered the prototype ILD. Although it is idiopathic in that the cause is not known, Reynolds, supra, notes that the term refers to a well defined clinical entity.

"Bronchoalveolar lavage," or "BAL," is a test which permits removal and examination of cells from the lower respiratory tract and is used in humans as a diagnostic procedure for pulmonary disorders such as IPF. In human patients, it is usually performed during bronchoscopy.

"Inhibition", "inhibits", "inhibiting" and "inhibitor" refer to a compound that prohibits or a method of prohibiting, a specific action or function.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "arylalkyl," "alkylamino," "alkylheteroaryl," "alkylheterocycloalkyl" and similar terms. In some embodiments, alkyl groups are those containing 1 to 24 carbon atoms. All numerical ranges in this specification and claims are intended to be inclusive of their upper and lower limits. Additionally, the alkyl and heteroalkyl groups may be attached to other moieties at any position on the alkyl or heteroalkyl radical which would otherwise be occupied by a hydrogen atom (such as, for example, 2-pentyl, 2-methylpent-1-yl and 2-propyloxy). Divalent alkyl groups may be referred to as "alkylene," and divalent heteroalkyl groups may be referred to as "heteroalkylene". The alkyl, alkylene, and heteroalkylene moieties may also be optionally substituted with halogen atoms, or other groups such as oxo, cyano, nitro, alkyl, alkylamino, carboxyl, hydroxyl, alkoxy, aryloxy, and the like.

The terms "cycloalkyl" and "cycloalkylene" refer to a saturated hydrocarbon ring and includes bicyclic and polycyclic rings. Similarly, cycloalkyl and cycloalkylene groups having a heteroatom (e.g. N, O or S) in place of a carbon ring atom may be referred to as "heterocycloalkyl" and "heterocycloalkylene," respectively. Examples of cycloalkyl and heterocycloalkyl groups are, for example, cyclohexyl, norbornyl, adamantyl, morpholinyl, thiomorpholinyl, dioxothiomorpholinyl, and the like. The cycloalkyl and heterocycloalkyl moieties may also be optionally substituted with halogen atoms, or other groups such as nitro, alkyl, alkylamino, carboxyl, alkoxy, aryloxy and the like. In some embodiments, cycloalkyl and cycloalkylene moieties are those having 3 to 12 carbon atoms in the ring (e.g., cyclohexyl, cyclooctyl, norbornyl, adamantyl, and the like). In some embodiments, heterocycloalkyl and heterocycloalkylene moieties are those having 1 to 3 hetero atoms in the ring (e.g., morpholinyl, thiomorpholinyl, dioxothiomorpholinyl, piperidinyl and the like). Additionally, the term "(cycloalkyl) alkyl" refers to a group having a cycloalkyl moiety attached to an alkyl moiety. Examples are cyclohexylmethyl, cyclohexylethyl and cyclopentylpropyl.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy and t-butoxy).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g. N, O or S) in place of a carbon ring atom are referred to as "heteroaryl". Examples of aryl and heteroaryl groups are, for example, phenyl, naphthyl, biphenyl, diphenylmethyl, thienyl, pyridyl and quinoxalyl. The aryl and heteroaryl moieties may also be optionally substituted with halogen atoms, or other groups such as nitro, alkyl, alkylamino, carboxyl, alkoxy, phenoxy and the like. Additionally, the aryl and heteroaryl groups may be attached to other moieties at any position on the aryl or heteroaryl radical which would otherwise be occupied by a hydrogen atom (such as, for example, 2-pyridyl, 3-pyridyl and 4-pyridyl). Divalent aryl groups are "arylene", and divalent heteroaryl groups are referred to as "heteroarylene" such as those groups used as linkers in the present invention.

The terms "arylalkyl" and "alkylaryl", "refer to an aryl radical attached directly to an alkyl group. Likewise, the terms "arylalkenyl" and "aryloxyalkyl" refer to an alkenyl group, or an oxygen which is attached to an alkyl group, respectively. For brevity, aryl as part of a combined term as above, is meant to include heteroaryl as well. The term "aryloxy" refers to an aryl radical as described above which also bears an oxygen substituent which is capable of covalent attachment to another radical (such as, for example, phenoxy, naphthyloxy, and pyridyloxy).

The terms "halo" or "halogen," by themselves or as part of another substituent, mean, unless otherwise stated, a fluorine, chlorine, bromine, or iodine atom. Additionally, terms such as "haloalkyl," and "haloalkoxy" are meant to include monohaloalkyl(oxy) and polyhaloalkyl(oxy). For example, the term "$C_1$-$C_6$ haloalkyl" is mean to include trifluoromethyl, 2,2,2-trifluoroethyl, 4-chlorobutyl, 3-bromopropyl, and the like.

The term "hetero" as used in a "heteroatom-containing alkyl group" (a "heteroalkyl" group) or a "heteroatom-containing aryl group" (a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur or more than one non-carbon atom (e.g., sulfonamide). Similarly, the term "heteroalkyl" refers to an alkyl substituent that is heteroatom-containing, the terms "heterocyclic", "heterocycle", "heterocycloalkyl" or "heterocyclyl" refer to a cyclic substituent or group that is heteroatom-containing and is either aromatic or non-aromatic. The terms "heteroaryl" and "heteroaromatic" respectively refer to "aryl" and "aromatic" substituents that are heteroatom-containing, and the like. The terms "heterocyclic" and "heterocyclyl" include the terms "heteroaryl" and "heteroaromatic". In some embodiments, heterocyclic moieties are those having 1 to 3 hetero atoms in the ring. Examples of heteroalkyl groups include alkoxy, alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing cyclic nonaromatic groups are morpholinyl, piperazinyl, piperidinyl, etc.

The term "carboxylic acid analog" refers to a variety of groups having an acidic moiety that are capable of mimicking a carboxylic acid residue. Examples of such groups are sulfonic acids, sulfinic acids, phosphoric acids, phosphonic acids, phosphinic acids, sulfonamides, and heterocyclic moieties such as, for example, imidazoles, triazoles and tetrazoles.

The term "substituted" refers to the replacement of an atom or a group of atoms of a compound with another atom or group of atoms. For example, an atom or a group of atoms may be substituted with one or more of the following substituents or groups: halo, nitro, $C_1$-$C_8$alkyl, $C_1$-$C_8$alkylamino, hydroxy$C_1$-$C_8$alkyl, halo$C_1$-$C_8$alkyl, carboxyl, hydroxyl, $C_1$-$C_8$alkoxy, $C_1$-$C_8$alkoxy$C_1$-$C_8$alkoxy, thio$C_1$-$C_8$alkyl, aryl, aryloxy, $C_3$-$C_8$cycloalkyl, $C_3$-$C_8$cycloalkyl$C_1$-$C_8$alkyl, heteroaryl, aryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_4$-$C_8$alk(en)(yn)yl groups, cyano, formyl, $C_1$-$C_8$alkylcarbonyl, aryl-carbonyl, heteroarylcarbonyl, $C_1$-$C_8$alkoxycarbonyl, aryloxycarbonyl, aminocarbonyl, $C_1$-$C_8$alkylaminocarbonyl, $C_1$-$C_8$dialkylaminocarbonyl, arylaminocarbonyl, diarylaminocarbonyl, aryl$C_1$-$C_8$alkylaminocarbonyl, halo$C_1$-$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkylamino$C_1$-$C_8$alkyl, arylamino$C_1$-$C_8$alkyl, amino, $C_1$-$C_8$dialkylamino, aryl amino, aryl$C_1$-$C_8$alkylamino, $C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfinyl, $C_1$-$C_8$alkylsulfonyl, arylsulfinyl, arylsulfonyl, aminosulfonyl, $C_1$-$C_8$alkylaminosulfonyl, $C_1$-$C_8$dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

II. General

The present invention derives from the discovery that 1,3-disubstituted ureas (or the corresponding amides or carbamates, also referred to as the primary pharmacophore) can be further functionalized to provide more potent sEH inhibitors with improved physical properties. As described herein, the introduction of a heterocyclic moiety can increase water solubility and oral availability of sEH inhibitors (see below). The combination of these moieties provides a variety of compounds of increased water solubility.

The discovery of the heterocyclic pharmacophores has also led to the employment of combinatorial chemistry approaches for establishing a wide spectrum of compounds having sEH inhibitory activity. The polar pharmacophores divide the molecule into domains each of which can be easily manipulated by common chemical approaches in a combinatorial manner, leading to the design and confirmation of novel orally available therapeutic agents for the treatment of diseases such as hypertension and vascular inflammation. The agents of the present invention treat such diseases while simultaneously increasing sodium excretion, reducing vascular and renal inflammation, and reducing male erectile dysfunction As shown below (see Examples and Figures), alterations in solubility, bioavailability and pharmacological properties leads to compounds that can alter the regulatory lipids of experimental animals increasing the relative amounts of epoxy arachidonate derivatives when compared either to their diol products or to the proinflammatory and hypertensive hydroxyeicosatetraenoic acids (HETEs). Since epoxy arachidonates are anti-hypertensive and anti-inflammatory, altering the lipid ratios can lead to reduced blood pressure and reduced vascular and renal inflammation. This approach has been validated as reported in U.S. patent application Ser. Nos. 10/817,334 and 11/256,685 which are herein incorporated by reference in their entirety.

The heterocyclic group improves water solubility of sEH inhibitors as well as the specificity for the sEH, and a wide diversity of functionalities such as an ester, amide, carbamate, or similar functionalities capable of donating or accepting a hydrogen bond similarly can contribute to this polar group. For example, in pharmaceutical chemistry heterocyclic groups are commonly used to mimic carbonyls as hydrogen bond donors and acceptors. Of course the primary, secondary and tertiary pharmacophore groups can be combined in a single molecule with suitable spacers to improve activity or present the inhibitor as a prodrug.

III. Compounds for Inhibiting Soluble Epoxide Hydrolases

In addition to the methods provided below, the present invention provides compounds that can inhibit the activity of soluble epoxide hydrolases. In particular; the present invention provides compounds having a formula selected from the formulas below. The compounds of the present invention have chemical handles that allow attachment of fluorescent molecules useful for binding studes such as fluorescence polarization or FRET. Affinity ligands can also be attached to the compounds of the present invention.

In some embodiments, the present invention provides a compound having formula II:

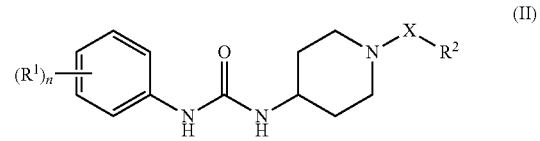

(II)

wherein each $R^1$ of formula II is independently H, halogen, $C_{1-6}$ alkyl, $C_{1-6}$ alkoxy, $C_{1-6}$ haloalkyl, $C_{1-6}$ haloalkoxy, —O-aryl, heterocycloalkyl having 5-6 ring members and at least 1 N heteroatom and 10 heteroatom as ring members, —OH, —$NO_2$ or —C(O)O$R^3$, wherein at least 1 $R^1$ is other than H. Alternatively, two $R^1$ groups on adjacent carbons are joined to form a 5-6 membered heterocycloalkyl ring having from 1-20 heteroatoms as ring members. Radical X of formula II is —C(O)— or —S(O)$_2$—. Radical $R^2$ of formula II is $C_{1-6}$ alkyl, $C_{1-6}$ haloalkyl, cycloalkyl having 3-6 ring members, $C_{1-6}$ alkyl-heterocycloalkyl having from 5-6 ring members and at least 2 N heteroatoms as ring members and substituted with a member benzyl or —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen. Radical $R^3$ of formula II is H or $C_{1-6}$ alkyl. Subscript n of formula II is an integer from 1 to 5. When $R^1$ is $C_{1-6}$ haloalkoxy, then $R^2$ is $C_{2-6}$ alkyl, $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member benzyl or —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen. The salts and isomers of the compounds of formula II are also encompassed by the present invention.

In other embodiments, when $R^1$ is $C_{1-6}$ haloalkoxy and X is —C(O)—, then $R^2$ is cycloalkyl having 3-6 ring members, $C_{1-6}$ alkyl-heterocycloalkyl having from 5-6 ring members and at least 2 N heteroatoms as ring members and substituted with a member benzyl or —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen. In some other embodiments, when $R^1$ is $C_{1-6}$ haloalkoxy and X is —S(O)$_2$—, then $R^2$ is $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member benzyl or —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen.

In some embodiments, the present invention provides a compound having formula I:

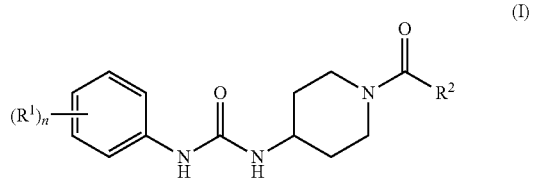

(I)

wherein each $R^1$ of formula I is H, halogen, $C_{1-6}$ alkyl, $C_{1-6}$ alkoxy, $C_{1-6}$ haloalkyl, $C_{1-6}$ haloalkoxy, —O-aryl, heterocycloalkyl having 5-6 ring members and at least 1 N heteroatom and 10 heteroatom as ring members, —OH, —NO$_2$ or —C(O)OR$^3$, wherein at least 1 $R^1$ is other than H. Alternatively, two $R^1$ groups on adjacent carbons are joined to form a 5-6 membered heterocycloalkyl ring having from 1-20 heteroatoms as ring members. $R^2$ of formula I is $C_{1-6}$ alkyl and $R^3$ is H or $C_{1-6}$ alkyl. Subscript n of formula I is an integer from 1 to 5. When $R^1$ of formula I is $C_{1-6}$ haloalkoxy, then $R^2$ is $C_{2-6}$ alkyl. The salts and isomers of the compounds of formula I are also encompassed by the present invention.

In other embodiments, the compounds of the present invention are those having formula Ia:

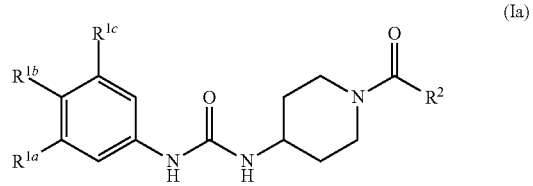

(Ia)

wherein $R^{1a}$, $R^{1b}$ and $R^{1c}$ are each independently selected from the members of the group defined by $R^1$. In some other embodiments, the compounds of the present invention include those having the formula Ib:

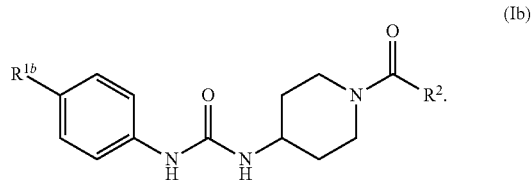

(Ib)

In another embodiment, each $R^1$ of formula I is halogen, $C_{1-6}$ alkyl, $C_{1-6}$ alkoxy, —O-aryl, heterocycloalkyl having 5-6 ring members and at least 1 N heteroatom and 10 heteroatom as ring members, —OH, —NO$_2$ or —C(O)OR$^3$. In other embodiments, each $R^1$ of formula I is halogen or $C_{1-6}$ haloalkyl. In some other embodiments, each $R^1$ of formula I is halogen, $C_{1-6}$ haloalkyl or —O-aryl. Alternatively, two $R^1$ groups on adjacent carbons are joined to form a 5 membered heterocycloalkyl ring having 20 heteroatoms as ring members. In still other embodiments, each $R^1$ of formula I is Cl, perfluoro-isopropyl or phenoxy. In yet other embodiments, $R^2$ of formula I is ethyl.

In some embodiments, the compounds of formula I have the following formula:

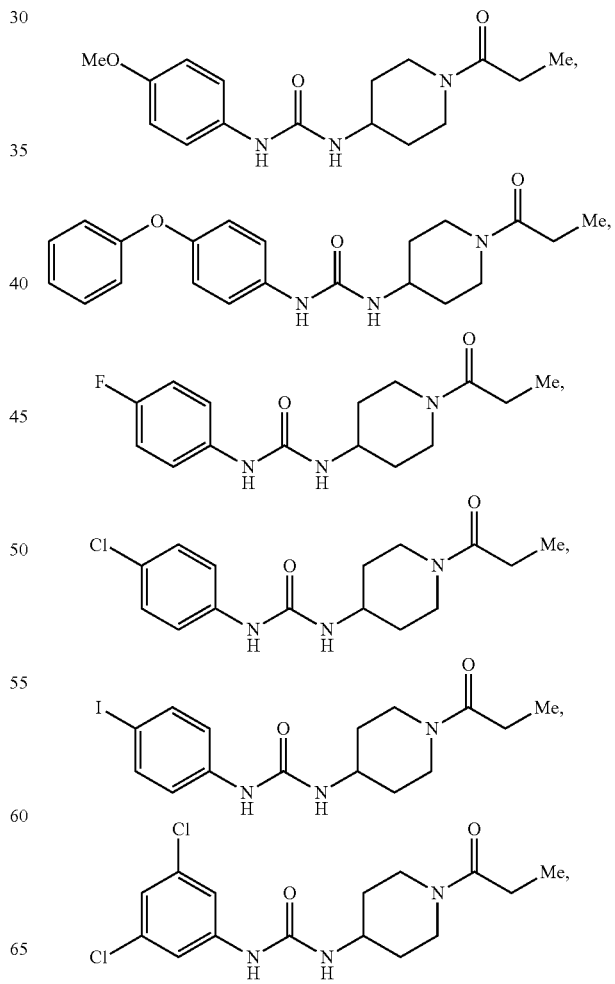

-continued

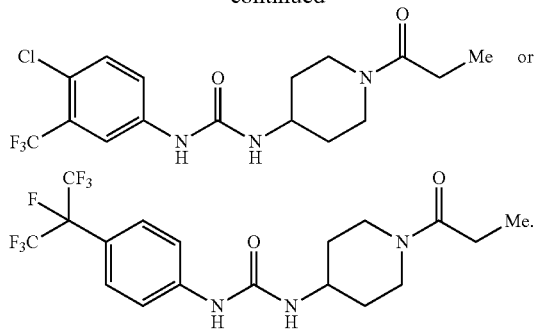

In other embodiments, the present invention provides a compound having formula II:

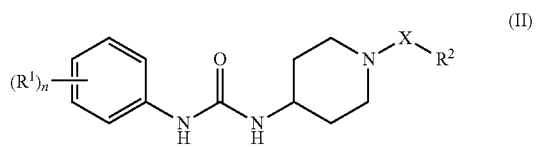

wherein $R^1$ of formula II is $C_{1-6}$ haloalkyl or $C_{1-6}$ haloalkoxy and X is —C(O)— or —S(O)$_2$—. Radical $R^2$ of formula II is $C_{2-6}$ alkyl, $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member the group consisting of benzyl and —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen. The salts and isomers of the compounds of formula II are also encompassed by the present invention.

In another embodiments, the present invention provides a compound having formula II, wherein $R^1$ of formula II is $C_{1-6}$ haloalkoxy and X is —C(O)— or —S(O)$_2$—. Radical $R^2$ of formula II is $C_{2-6}$ alkyl, $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member the group consisting of benzyl and —C(O)—$C_{1-6}$ alkyl, phenyl optionally substituted with OH, or $C_{0-6}$ alkyl-heteroaryl having 5-6 ring members and at least 1 N heteroatom as a ring member and optionally substituted with halogen. The salts and isomers of the compounds of formula II are also encompassed by the present invention.

In some other embodiments, the compounds of the present invention include those having formula IIa:

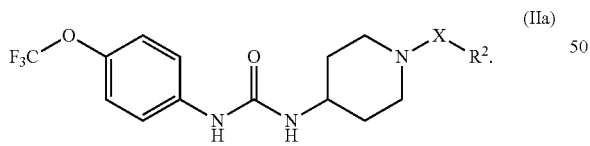

In still other embodiments, the compounds of the present invention include those having formula IIb:

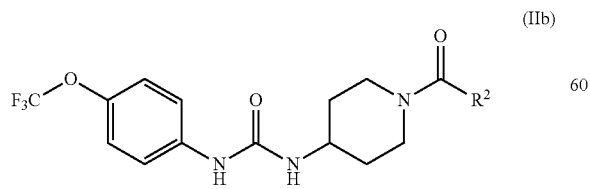

wherein $R^2$ of formula IIb is $C_{2-6}$ haloalkyl, cycloalkyl having 3-6 ring members, $C_{1-6}$ alkyl-heterocycloalkyl having from 5-6 ring members and at least 2 N heteroatoms as ring members and substituted with a member the group consisting of benzyl and —C(O)—$C_{1-6}$ alkyl, phenyl substituted with OH, or $C_{0-6}$ alkyl-heteroaryl having 5-6 ring members and at least 1 N heteroatom as a ring member and optionally substituted with a halogen.

In yet other embodiments, $R^2$ of formula I is —CH$_2$-heterocycloalkyl having 6 ring members and 2 N heteroatoms as ring members and substituted with acetyl. In still yet other embodiments, the compound has the formula:

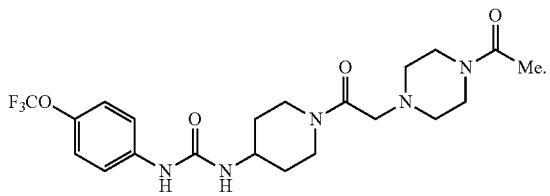 [SMILES: CC(=O)N1CCN(CC(=O)N2CCC(NC(=O)Nc3ccc(OC(F)(F)F)cc3)CC2)CC1]

In another embodiment, the compounds of the present invention are those having formula IIc:

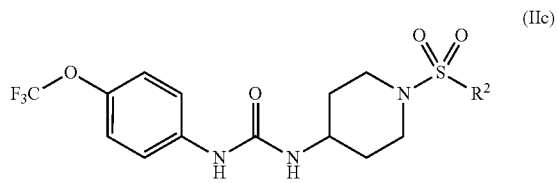

wherein $R^2$ of formula IIc is $C_{2-6}$ alkyl or unsubstituted phenyl. In some embodiments, the compound of formula IIc has the formula:

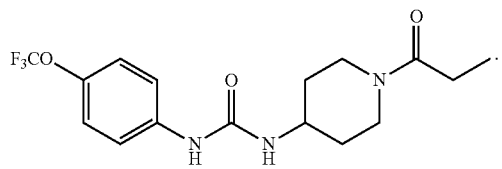 [SMILES: CCC(=O)N1CCC(NC(=O)Nc2ccc(OC(F)(F)F)cc2)CC1]

In another embodiment, the compounds of the present invention are those having formula IId:

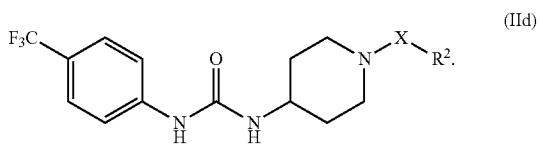

In another embodiment, the compounds of the present invention are those having formula IIe:

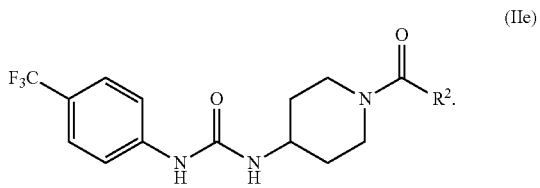

In another embodiment, the compounds of the present invention are those having formula IIf:

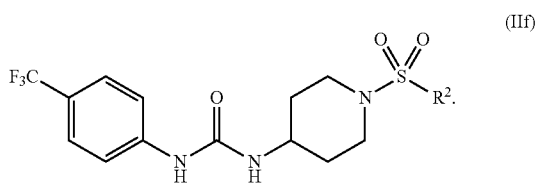

In another embodiment, the compounds of the present invention are:

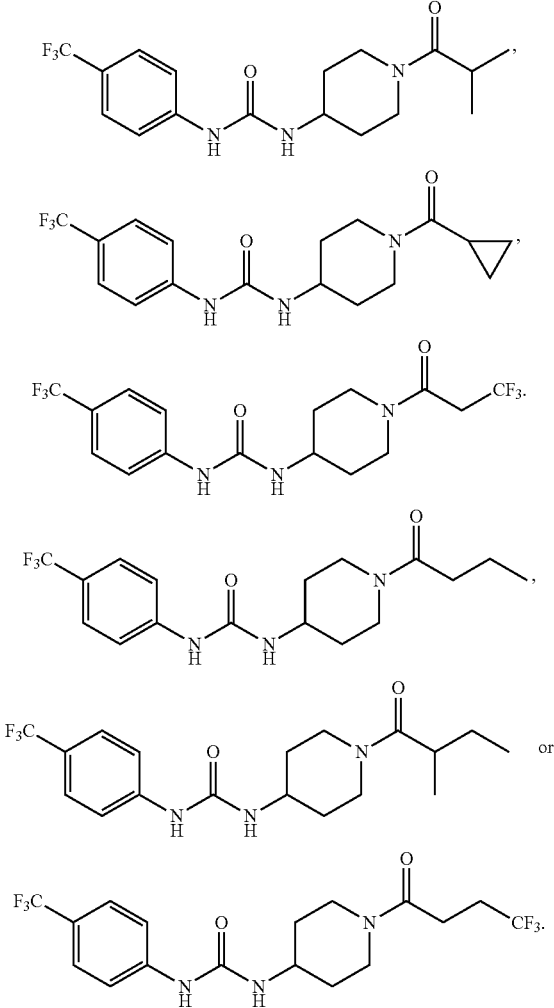

In another embodiment, the compounds of the present invention are:

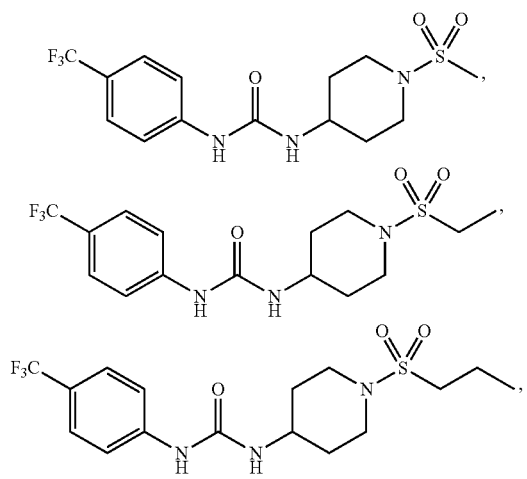

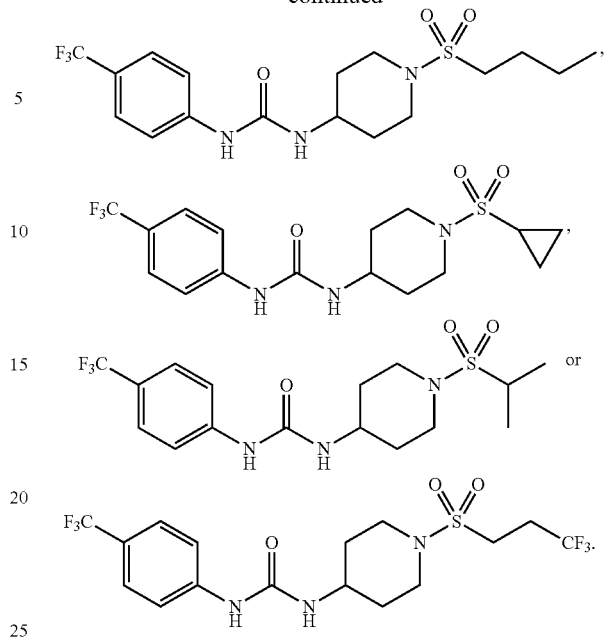

Certain compounds of the present invention possess asymmetric carbon atoms (optical centers) or double bonds; the racemates, diastereomers, geometric isomers and individual isomers are all intended to be encompassed within the scope of the present invention.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In some embodiments, sEH inhibitors for treating hypertension or high blood pressure have an $IC_{50}$ in a defined assay of less than 50 μM. In another embodiment, the compounds have an $IC_{50}$ of 1 μM or less. In another embodiment, the compounds have an $IC_{50}$ of 500 nM or less. In another embodiment, the compounds have an $IC_{50}$ of 150 nM or less. In another embodiment, the compounds have an $IC_{50}$ of 100 nM or less. In another embodiment, the compounds have an $IC_{50}$ of 50 nM or less. In another embodiment, the compounds have an $IC_{50}$ of 1 nM or less.

The compounds of the present invention can be prepared by a variety of methods as outlined generally in the schemes. It should be noted that the synthetic conditions illustrated in the following scheme are also applicable to those inhibitors based on 4-aminomethylpiperidine (those with a $CH_2$ spacer).

Scheme 1 outlines the two general synthetic routes used to form the unsymmetrical 1,3-disubstituted urea pharmacophore. Aryl isocyanates were purchased or formed from their corresponding anilines by reaction with triphosgene in the presence of aqueous base (*J. Org. Chem.* 1996, 61, 3929-3934). The heptafluoroisopropylanilines required for compounds 38 and 39 were prepared as described (EP 1006102, Jun. 7, 2000).

Amine 1 was prepared from 4-aminopiperidine by protection of the primary amine as its benzyl imine (*Bioorg. Med. Chem.* 2003, 11, 4225-4234), reaction with propionyl chloride in the presence of triethylamine and subsequent deprotection. All isocyanates were reacted with amine 1 to give the desired (1-propionylpiperidin-4-yl)ureas 2-16, 18-21 and 24-40. Saponification of methyl ester 21 with methanolic NaOH afforded benzoic acid 22. Phenol 23 was prepared via 4-benzyloxyisocyanate to avoid formation of a carbamate side product.

Compounds 17 and 31 were prepared by conversion of the corresponding aniline to the intermediate 4-nitrophenyl carbamate, which was then reacted with amine 1 to give the desired urea.

Intermediate 41 (Scheme 2) was prepared by the reaction of 4-trifluoromethoxyphenyl isocyanate with 1-BOC-4-aminopiperidine. BOC de-protection gave piperidine 42, which was converted to N-acyl compounds 47-50 and 52 by an EDCI mediated coupling reaction with the respective carboxylic acid (*Bioorg. Med. Chem.* 2003, 11, 4225-4234). Acetylpiperazine 51 was prepared by de-benzylation of 50 and subsequent N-acetylation. Trifluoroacetyl compound 53 was prepared by the reaction of intermediate 42 with ethyl trifluoroacetate. Trihydroxybenzoyl compound 52 was prepared by coupling of 42 with tris O-benzyl protected gallic acid (44) followed by hydrogenolysis (*J. Med. Chem.* 2006, 49, 2829-2837). Intermediate 42 was also converted to N-sulfonyl compounds 55-59 by reaction with the respective sulfonyl chlorides.

IV. Pharmaceutical Compositions

In another embodiment, the present invention provides a pharmaceutical composition, including a compound of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of the present invention, or a pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., *Remington's Pharmaceutical Sciences*, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethylcellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

V. Administration

Administration of the compounds of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Administration may also be directly to the bone surface and/or into tissues surrounding the bone.

The compositions containing a compound or a combination of compounds of the present invention may be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semisolid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a compound or a combination of compounds. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see, for example, *Remington's Pharmaceutical Sciences,* 18TH ED., Mack Publishing Co., Easton, Pa. (1990)). The composition to be administered contains a quantity of the compound or combination of compounds in a pharmaceutically effective amount for relief of a condition being treated (e.g. osteoporosis) when administered in accordance with the teachings of this invention. In addition, pharmaceutically acceptable salts of the compounds of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the compounds or combination of compounds, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The compounds can also be formulated into a suppository disposed, for example, in a polyethylene glycol (PEG) carrier.

Liquid compositions can be prepared by dissolving or dispersing a compound or a combination of compounds and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The compounds of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the compound to the appropriate site or sites. However, one of ordinary skill in the art understands that the dose administered will vary depending on a number of factors, including, but not limited to, the particular compound or set of compounds to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the compounds of the present invention permits a wider margin of safety for dosage concentrations and for repeated dosing.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Methods

In view of the above, the present invention provides, in one aspect, a method for inhibiting a soluble epoxide hydrolase, comprising contacting the soluble epoxide hydrolase with an inhibiting amount of a compound of the present invention.

In other embodiments, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said sEH.

A. Assays to Monitor Soluble Epoxide Hydrolase Activity:

Additionally, the present invention provides a variety of assays and associated methods for monitoring soluble epoxide hydrolase activity, particularly the activity that has been modulated by the administration of one or more of the compounds provided above.

In one group of embodiments, the invention provides methods for reducing the formation of a biologically active diol produced by the action of a soluble epoxide hydrolase, the method comprising contacting the soluble epoxide hydrolase with an amount of a compound of the present invention, sufficient to inhibit the activity of the soluble epoxide hydrolase and reduce the formation of the biologically active diol.

In another group of embodiments, the invention provides methods for stabilizing biologically active epoxides in the presence of a soluble epoxide hydrolase, the method comprising contacting the soluble epoxide hydrolase with an amount of a compound of the present invention, sufficient to inhibit the activity of the soluble epoxide hydrolase and stabilize the biologically active epoxide.

In each of these groups of embodiments, the methods can be carried out as part of an in vitro assay or the methods can be carried out in vivo by monitoring blood titers of the respective biologically active epoxide or diol.

Epoxides and diols of some fatty acids are biologically important chemical mediators and are involved in several biological processes. The strongest biological data support the action of oxylipins as chemical mediators between the vascular endothelium and vascular smooth muscle. Epoxy lipids are anti-inflammatory and anti-hypertensive. Additionally, the lipids are thought to be metabolized by beta-oxidation, as well as by epoxide hydration. The soluble epoxide hydrolase is considered to be the major enzyme involved in the hydrolytic metabolism of these oxylipins. The compounds of the present invention can inhibit the epoxide hydrolase and stabilize the epoxy lipids both in vitro and in vivo. This activity results in a reduction of hypertension in four separate rodent models. Moreover, the inhibitors show a reduction in renal inflammation associated with and independent of the hypertensive models.

More particularly, the present invention provides methods for monitoring a variety of lipids in both the arachidonate and linoleate cascade simultaneously in order to address the biology of the system. A GLC-MS system or a LC-MS method can be used to monitor over 740 analytes in a highly quantitative fashion in a single injection. The analytes include the regioisomers of the arachidonate epoxides (EETs), the diols (DHETs), as well as other P450 products including HETEs. Characteristic products of the cyclooxygenase, lipoxygenase, and peroxidase pathways in both the arachidonate and linoleate series can also be monitored. Such methods are particularly useful as being predictive of certain disease states. The oxylipins can be monitored in mammals following the administration of inhibitors of epoxide hydrolase. Generally, EH inhibitors increase epoxy lipid concentrations at the expense of diol concentrations in body fluids and tissues.

Other compounds for use in this aspect of the invention are those compounds of the present invention in which the primary pharmacophore is separated from a secondary and/or tertiary pharmacophore by a distance that approximates the distance between the terminal carboxylic acid and an epoxide functional group in the natural substrate.

B. Methods of Treating Diseases Modulated by Soluble Epoxide Hydrolases:

In another aspect, the present invention provides methods of treating diseases, especially those modulated by soluble epoxide hydrolases (sEH). The methods generally involve administering to a subject in need of such treatment an effective amount of a compound of the present invention. The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on the disease target, the patient, and the route of administration. Dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

It has previously been shown that inhibitors of soluble epoxide hydrolase ("sEH") can reduce hypertension. See, e.g., U.S. Pat. No. 6,351,506. Such inhibitors can be useful in controlling the blood pressure of persons with undesirably high blood pressure, including those who suffer from diabetes.

In some embodiments, compounds of the present invention are administered to a subject in need of treatment for hypertension, specifically renal, hepatic, or pulmonary hypertension; inflammation, specifically renal inflammation, vascular inflammation, and lung inflammation; adult respiratory distress syndrome; diabetic complications; end stage renal disease; Raynaud syndrome and arthritis.

C. Methods for Inhibiting Progression of Kidney Deterioration (Nephropathy) and Reducing Blood Pressure:

In another aspect of the invention, the compounds of the invention can reduce damage to the kidney, and especially damage to kidneys from diabetes, as measured by albuminuria. The compounds of the invention can reduce kidney deterioration (nephropathy) from diabetes even in individuals who do not have high blood pressure. The conditions of therapeutic administration are as described above.

cis-Epoxyeicosantrienoic acids ("EETs") can be used in conjunction with the compounds of the invention to further reduce kidney damage. EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into DHETs is reduced. Without wishing to be bound by theory, it is believed that raising the level of EETs interferes with damage to kidney cells by the microvasculature changes and other pathologic effects of diabetic hyperglycemia. Therefore, raising the EET level in the kidney is believed to protect the kidney from progression from microalbuminuria to end stage renal disease.

EETs are well known in the art. EETs useful in the methods of the present invention include 14,15-EET, 8,9-EET and 11,12-EET, and 5,6 EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present invention, these favorable properties are believed to protect the vasculature and organs during renal and cardiovascular disease states.

It is now believed that sEH activity can be inhibited sufficiently to increase the levels of EETs and thus augment the effects of administering sEH inhibitors by themselves. This permits EETs to be used in conjunction with one or more sEH inhibitors to reduce nephropathy in the methods of the invention. It further permits EETs to be used in conjunction with one or more sEH inhibitors to reduce hypertension, or inflammation, or both. Thus, medicaments of EETs can be made which can be administered in conjunction with one or more sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable that the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In some embodiments, the EETs, the compound of the invention, or both, are provided in a material that permits them to be released over time to provide a longer duration of action. Slow release coatings are well known in the pharmaceutical art; the choice of the particular slow release coating is not critical to the practice of the present invention.

EETs are subject to degradation under acidic conditions. Thus, if the EETs are to be administered orally, it is desirable that they are protected from degradation in the stomach. Conveniently, EETs for oral administration may be coated to permit them to passage the acidic environment of the stomach into the basic environment of the intestines. Such coatings are well known in the art. For example, aspirin coated with so-called "enteric coatings" is widely available commercially. Such enteric coatings may be used to protect EETs during passage through the stomach. An exemplary coating is set forth in the Examples.

While the anti-hypertensive effects of EETs have been recognized, EETs have not been administered to treat hypertension because it was thought endogenous sEH would hydrolyse the EETs too quickly for them to have any useful effect. Surprisingly, it was found during the course of the studies underlying the present invention that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in at least some improvement in symptoms or pathology, it may not be sufficient in all cases to inhibit progression of kidney damage fully or to the extent intended. This is particularly true where the diseases or other factors have reduced the endogenous concentrations of EETs below those normally present in healthy individuals. Administration of exogenous EETs in conjunction with a sEH inhibitor is therefore expected to be beneficial and to augment the effects of the sEH inhibitor in reducing the progression of diabetic nephropathy.

The present invention can be used with regard to any and all forms of diabetes to the extent that they are associated with progressive damage to the kidney or kidney function. The chronic hyperglycemia of diabetes is associated with long-term damage, dysfunction, and failure of various organs, especially the eyes, kidneys, nerves, heart, and blood vessels. The long-term complications of diabetes include retinopathy with potential loss of vision; nephropathy leading to renal failure; peripheral neuropathy with risk of foot ulcers, amputation, and Charcot joints.

In addition, persons with metabolic syndrome are at high risk of progression to type 2 diabetes, and therefore at higher risk than average for diabetic nephropathy. It is therefore desirable to monitor such individuals for microalbuminuria, and to administer a sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some embodiments, the person has metabolic syndrome and blood pressure below 130/85.

Dyslipidemia or disorders of lipid metabolism is another risk factor for heart disease. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. It is believed that high levels of triglycerides are associated with kidney damage. In particular, levels of cholesterol over 200 mg/dL, and especially levels over 225 mg/dL, would suggest that sEH inhibitors and, optionally, EETs, should be administered. Similarly, triglyceride levels of more than 215 mg/dL, and especially of 250 mg/dL or higher, would indicate that administration of sEH inhibitors and, optionally, of EETs, would be desirable. The administration of compounds of the present invention with or without the EETs, can reduce the need to administer statin drugs (HMG-CoA reductase inhibitors) to the patients, or reduce the amount of the statins needed. In some embodiments, candidates for the methods, uses and compositions of the invention have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the invention have cholesterol levels over 200 mg/dL and blood pressure below 130/85. In some embodiments, the candidates have cholesterol levels over 225 mg/dL and blood pressure below 130/85.

D. Methods of Inhibiting the Proliferation of Vascular Smooth Muscle Cells:

In other embodiments, compounds of the present invention inhibit proliferation of vascular smooth muscle (VSM) cells without significant cell toxicity, (e.g., specific to VSM cells). Because VSM cell proliferation is an integral process in the pathophysiology of atherosclerosis, these compounds are suitable for slowing or inhibiting atherosclerosis. These compounds are useful to subjects at risk for atherosclerosis, such as individuals who have had a heart attack or a test result showing decreased blood circulation to the heart. The conditions of therapeutic administration are as described above.

The methods of the invention are particularly useful for patients who have had percutaneous intervention, such as angioplasty to reopen a narrowed artery, to reduce or to slow the narrowing of the reopened passage by restenosis. In some embodiments, the artery is a coronary artery. The compounds of the invention can be placed on stents in polymeric coatings to provide a controlled localized release to reduce restenosis. Polymer compositions for implantable medical devices, such as stents, and methods for embedding agents in the polymer for controlled release, are known in the art and taught, for example, in U.S. Pat. Nos. 6,335,029; 6,322,847; 6,299,604; 6,290,722; 6,287,285; and 5,637,113. In some embodiments, the coating releases the inhibitor over a period of time, preferably over a period of days, weeks, or months. The particular polymer or other coating chosen is not a critical part of the present invention.

The methods of the invention are useful for slowing or inhibiting the stenosis or restenosis of natural and synthetic vascular grafts. As noted above in connection with stents, desirably, the synthetic vascular graft comprises a material which releases a compound of the invention over time to slow or inhibit VSM proliferation and the consequent stenosis of the graft. Hemodialysis grafts are a particular embodiment.

In addition to these uses, the methods of the invention can be used to slow or to inhibit stenosis or restenosis of blood vessels of persons who have had a heart attack, or whose test results indicate that they are at risk of a heart attack.

In one group of embodiments, compounds of the invention are administered to reduce proliferation of VSM cells in persons who do not have hypertension. In another group of embodiments, compounds of the invention are used to reduce proliferation of VSM cells in persons who are being treated for hypertension, but with an agent that is not an sEH inhibitor.

The compounds of the invention can be used to interfere with the proliferation of cells which exhibit inappropriate cell cycle regulation. In one important set of embodiments, the cells are cells of a cancer. The proliferation of such cells can be slowed or inhibited by contacting the cells with a compound of the invention. The determination of whether a particular compound of the invention can slow or inhibit the proliferation of cells of any particular type of cancer can be determined using assays routine in the art.

In addition to the use of the compounds of the invention, the levels of EETs can be raised by adding EETs. VSM cells contacted with both an EET and a compound of the invention exhibited slower proliferation than cells exposed to either the EET alone or to the a compound of the invention alone. Accordingly, if desired, the slowing or inhibition of VSM cells of a compound of the invention can be enhanced by adding an EET along with a compound of the invention. In the case of stents or vascular grafts, for example, this can conveniently be accomplished by embedding the EET in a coating along with a compound of the invention so that both are released once the stent or graft is in position.

E. Methods of Inhibiting the Progression of Obstructive Pulmonary Disease, Interstitial Lung Disease, or Asthma:

Chronic obstructive pulmonary disease, or COPD, encompasses two conditions, emphysema and chronic bronchitis, which relate to damage caused to the lung by air pollution, chronic exposure to chemicals, and tobacco smoke. Emphysema as a disease relates to damage to the alveoli of the lung, which results in loss of the separation between alveoli and a consequent reduction in the overall surface area available for gas exchange. Chronic bronchitis relates to irritation of the bronchioles, resulting in excess production of mucin, and the consequent blocking by mucin of the airways leading to the alveoli. While persons with emphysema do not necessarily have chronic bronchitis or vice versa, it is common for persons with one of the conditions to also have the other, as well as other lung disorders.

Some of the damage to the lungs due to COPD, emphysema, chronic bronchitis, and other obstructive lung disorders can be inhibited or reversed by administering inhibitors of the enzyme known as soluble epoxide hydrolase, or "sEH". The effects of sEH inhibitors can be increased by also administering EETs. The effect is at least additive over administering the two agents separately, and may indeed be synergistic.

The studies reported herein show that EETs can be used in conjunction with sEH inhibitors to reduce damage to the lungs by tobacco smoke or, by extension, by occupational or environmental irritants. These findings indicate that the co-administration of sEH inhibitors and of EETs can be used to inhibit or slow the development or progression of COPD, emphysema, chronic bronchitis, or other chronic obstructive lung diseases which cause irritation to the lungs.

Animal models of COPD and humans with COPD have elevated levels of immunomodulatory lymphocytes and neutrophils. Neutrophils release agents that cause tissue damage and, if not regulated, will over time have a destructive effect. Without wishing to be bound by theory, it is believed that reducing levels of neutrophils reduces tissue damage contributing to obstructive lung diseases such as COPD, emphysema, and chronic bronchitis. Administration of sEH inhibitors to rats in an animal model of COPD resulted in a reduction in the number of neutrophils found in the lungs. Administration of EETs in addition to the sEH inhibitors also reduced neutrophil levels. The reduction in neutrophil levels in the presence of sEH inhibitor and EETs was greater than in the presence of the sEH inhibitor alone.

While levels of endogenous EETs are expected to rise with the inhibition of sEH activity caused by the action of the sEH inhibitor, and therefore to result in at least some improvement in symptoms or pathology, it may not be sufficient in all cases to inhibit progression of COPD or other pulmonary diseases. This is particularly true where the diseases or other factors have reduced the endogenous concentrations of EETs below those normally present in healthy individuals. Administration of exogenous EETs in conjunction with an sEH inhibitor is therefore expected to augment the effects of the sEH inhibitor in inhibiting or reducing the progression of COPD or other pulmonary diseases.

In addition to inhibiting or reducing the progression of chronic obstructive airway conditions, the invention also provides new ways of reducing the severity or progression of chronic restrictive airway diseases. While obstructive airway diseases tend to result from the destruction of the lung parenchyma, and especially of the alveoli, restrictive diseases tend to arise from the deposition of excess collagen in the parenchyma. These restrictive diseases are commonly referred to as "interstitial lung diseases", or "ILDs", and include conditions such as idiopathic pulmonary fibrosis. The methods, compositions and uses of the invention are useful for reducing the severity or progression of ILDs, such as idiopathic pulmonary fibrosis. Macrophages play a significant role in stimulating interstitial cells, particularly fibroblasts, to lay down collagen. Without wishing to be bound by theory, it is believed that neutrophils are involved in activating macrophages, and that the reduction of neutrophil levels found in the studies reported herein demonstrate that the methods and uses of the invention will also be applicable to reducing the severity and progression of ILDs.

In some embodiments, the ILD is idiopathic pulmonary fibrosis. In other embodiments, the ILD is one associated with an occupational or environmental exposure. Exemplars of such ILDs, are asbestosis, silicosis, coal worker's pneumoconiosis, and berylliosis. Further, occupational exposure to any of a number of inorganic dusts and organic dusts is believed to be associated with mucus hypersecretion and respiratory disease, including cement dust, coke oven emissions, mica, rock dusts, cotton dust, and grain dust (for a more complete list of occupational dusts associated with these conditions, see Table 254-1 of Speizer, "Environmental Lung Diseases," Harrison's Principles of Internal Medicine, infra, at pp. 1429-1436). In other embodiments, the ILD is sarcoidosis of the lungs. ILDs can also result from radiation in medical treatment, particularly for breast cancer, and from connective tissue or collagen diseases such as rheumatoid arthritis and systemic sclerosis. It is believed that the methods, uses and compositions of the invention can be useful in each of these interstitial lung diseases.

In another set of embodiments, the invention is used to reduce the severity or progression of asthma. Asthma typically results in mucin hypersecretion, resulting in partial airway obstruction. Additionally, irritation of the airway results in the release of mediators which result in airway obstruction. While the lymphocytes and other immunomodulatory cells recruited to the lungs in asthma may differ from those recruited as a result of COPD or an ILD, it is expected that the invention will reduce the influx of immunomodulatory cells, such as neutrophils and eosinophils, and ameliorate the extent of obstruction. Thus, it is expected that the administration of sEH inhibitors, and the administration of sEH inhibitors in combination with EETs, will be useful in reducing airway obstruction due to asthma.

In each of these diseases and conditions, it is believed that at least some of the damage to the lungs is due to agents released by neutrophils which infiltrate into the lungs. The presence of neutrophils in the airways is thus indicative of continuing damage from the disease or condition, while a reduction in the number of neutrophils is indicative of reduced damage or disease progression. Thus, a reduction in the number of neutrophils in the airways in the presence of an agent is a marker that the agent is reducing damage due to the disease or condition, and is slowing the further development of the disease or condition. The number of neutrophils present in the lungs can be determined by, for example, bronchoalveolar lavage.

F. Prophylatic and Therapeutic Methods to Reduce Stroke Damage

Inhibitors of soluble epoxide hydrolase ("sEH") and EETs administered in conjunction with inhibitors of sEH have been shown to reduce brain damage from strokes. Based on these results, we expect that inhibitors of sEH taken prior to an ischemic stroke will reduce the area of brain damage and will likely reduce the consequent degree of impairment. The reduced area of damage should also be associated with a faster recovery from the effects of the stroke.

While the pathophysiologies of different subtypes of stroke differ, they all cause brain damage. Hemorrhagic stroke differs from ischemic stroke in that the damage is largely due to compression of tissue as blood builds up in the confined space within the skull after a blood vessel ruptures, whereas in ischemic stroke, the damage is largely due to loss of oxygen supply to tissues downstream of the blockage of a blood vessel by a clot. Ischemic strokes are divided into thrombotic strokes, in which a clot blocks a blood vessel in the brain, and embolic strokes, in which a clot formed elsewhere in the body is carried through the blood stream and blocks a vessel there. But, in both hemorrhagic stroke and ischemic stroke, the damage is due to the death of brain cells. Based on the results observed in our studies, however, we would expect at least some reduction in brain damage in all types of stroke and in all subtypes.

A number of factors are associated with an increased risk of stroke. Given the results of the studies underlying the present invention, sEH inhibitors administered to persons with any one or more of the following conditions or risk factors: high blood pressure, tobacco use, diabetes, carotid artery disease, peripheral artery disease, atrial fibrillation, transient ischemic attacks (TIAs), blood disorders such as high red blood cell counts and sickle cell disease, high blood cholesterol, obesity, alcohol use of more than one drink a day for women or two drinks a day for men, use of cocaine, a family history of stroke, a previous stroke or heart attack, or being elderly, will reduce the area of brain damaged of a stroke. With respect to being elderly, the risk of stroke increases for every 10 years. Thus, as an individual reaches 60, 70, or 80, administration of sEH inhibitors has an increasingly larger potential benefit. As noted in the next section, the administration of EETs in combination with one or more sEH inhibitors can be beneficial in further reducing the brain damage. One can expect beneficial effects from sEHI with or without EETs in a variety of diseases which lead to ischemia reperfusion injury such as heart attacks.

In some uses and methods, the sEH inhibitors and, optionally, EETs, are administered to persons who use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

Clot dissolving agents, such as tissue plasminogen activator (tPA), have been shown to reduce the extent of damage from ischemic strokes if administered in the hours shortly after a stroke. tPA, for example, is approved by the FDA for use in the first three hours after a stroke. Thus, at least some of the brain damage from a stroke is not instantaneous, but occurs over a period of time or after a period of time has elapsed after the stroke. It is therefore believed that administration of sEH inhibitors, optionally with EETs, can also reduce brain damage if administered within 6 hours after a stroke has occurred, more preferably within 5, 4, 3, or 2 hours after a stroke has occurred, with each successive shorter interval being more preferable. Even more preferably, the inhibitor or inhibitors are administered 2 hours or less or even 1 hour or less after the stroke, to maximize the reduction in brain damage. Persons of skill are well aware of how to make a diagnosis of whether or not a patient has had a stroke. Such determinations are typically made in hospital emergency rooms, following standard differential diagnosis protocols and imaging procedures.

In some uses and methods, the sEH inhibitors and, optionally, EETs, are administered to persons who have had a stroke within the last 6 hours who: use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

The conditions of therapeutic administration for all of these indications are as described above.

The following examples are provided to illustrate the invention and are not intended to limit any aspect of the invention as set forth above or in the claims below.

VII. Examples

Example 1

Synthesis of Compounds 1-59

General.

All reagents and solvents were purchased from commercial suppliers and were used without further purification. All reactions were performed under an inert atmosphere of dry nitrogen. Flash chromatography was performed on silica gel using a dry loading technique, where necessary for poorly soluble products, and elution with the appropriate solvent system. Melting points were determined using an OptiMelt melting point apparatus and are uncorrected. $^1$H-NMR spectra were collected using a Bruker Avance 500 MHz spectrometer or Varian Mercury 300 MHz spectrometer. Signal multiplicities are represented as singlet (s), doublet (d), double doublet (dd), triplet (t), quartet (q), quintet (quint), multiplet (m), broad (br), broad singlet (brs), broad doublet (br d), broad triplet (br t), broad multiplet (br m), doublet of doublet of doublets (ddd) and quartet of doublets (qd). Accurate masses were measured using a Micromass LCT ESI-TOF-MS equipped with a Waters 2795 HPLC. Log P and purity analyses were performed using a Hewlett Packard 1100 HPLC equipped with a diode array detector. A Phenomenex Luna 150 mm×4.6 mm, 5 µm, C-18 column was used for all HPLC analyses.

The abbreviations used in the examples below have the following meaning: melting point (Mp), mass spectroscopy (MS), thin layer chromatography (TLC), the parent peak in the MS plus H$^+$ ([M+H]$^+$), minute (min), kilogram (kg), milligram (mg), nanomolar (nM), tetrahydrofuran (THF), tertiary butoxy carbonyl (BOC), potassium sulfate (KHSO$_4$), potassium hydroxide (KOH), magnesium sulfate (MgSO$_4$), hydrogen chloride (HCl), dimethylsulfoxide (DMSO), ethyl (Et), ethyl acetate (EtOAc), methanol (MeOH), dichloromethane (CH$_2$Cl$_2$, DCM), area under the concentration (AUC).

Log P Determination.

Octanol-water partition coefficients were determined by an HPLC method following OECD guideline 117. The accepted error for this method is ±0.5 of shake flask values. Isocratic MeOH:H$_2$O (3:1, v/v), 50 mM ammonium acetate in MeOH:H$_2$O (3:1, v/v) adjusted to pH 9.0, and MeOH:H$_2$O (3:1, v/v) adjusted to pH 3.0 with H$_3$PO$_4$ were used for neutral, basic and acidic analytes, respectively, with a flow rate of 0.75 mL/min. The HPLC method was validated using compounds 24 and 54, which were found to have log P values of 1.9 and 2.3, respectively, using the shake flask method (OECD guideline 107).

Purity Determination.

Final products were dissolved in MeOH:H$_2$O (3:1, v/v) at 10 µg/mL, and 100 µL injections were analyzed in triplicate by HPLC-UV with detection at 210 nm, 230 nm, 254 nm and 290 nm. HPLC conditions were the same as those for log P determination. Purity was judged as the percent of total peak area for each wavelength. The lowest observed purity is reported. Compounds were also judged to be pure based on thin layer chromatography visualized with short wave UV and stained with basic potassium permanganate.

Method A—Synthesis of Aryl and Alkyl Isocyanates.

The aniline or amine (1 mmol) was added to an ice cold, stirred biphasic mixture of DCM (10 mL) and saturated sodium bicarbonate (10 mL), or 1N NaOH (3 mL) in brine (7 mL) where noted. Stirring was stopped momentarily, triphosgene (0.37 eq.) in DCM (1 mL) added via syringe to the lower DCM layer and stirring continued for 10 minutes. The DCM layer was removed and filtered through a bed of magnesium sulfate. The filtrate was evaporated to afford the corresponding isocyanate, which was used without further purification.

Method B—Synthesis of Ureas Via Isocyanate.

The isocyanate (1 mmol) was dissolved or suspended in dry THF (3-5 mL) and cooled in an ice bath. The amine (1 mmol) was dissolved in dry THF (1 mL) and slowly added to the reaction. Stirring was continued for 1 to 24 hours at rt. The reaction was quenched with dilute HCl (or water where the BOC group was present) and extracted into ethyl acetate. The combined organic phase was dried, evaporated and purified.

Method C—Synthesis of Ureas Via 4-Nitrophenylcarbamate.

To an ice cold solution of 4-nitrophenyl chloroformate (1 eq) in dry THF was added $Et_3N$ (1.3 eq) and the appropriate aniline (1 eq) dissolved in dry THF. The reaction was allowed to warm to rt, stirred for 30 minutes and then filtered. The filtrate was evaporated and dissolved in DMF. Amine 1 was added and the reaction warmed to 50° C. for 1-3 hours. The mixture was cooled to rt, diluted with ethyl acetate, and the organic phase washed with 1N NaOH until the wash was free of yellow p-nitrophenol. The organic phase was dried, evaporated and purified.

Method D—Synthesis of N-Acyl Piperidine Analogues.

To a solution of 41 (1 eq) in DCM was added the corresponding carboxylic acid (1.1 eq), DMAP (1 eq) and EDCI (1.1 eq). The reaction was stirred for 12-24 hours at rt, and neutral products worked up by partition with EtOAc and 1N HCl (basic products by partition with saturated sodium bicarbonate and EtOAc) and the organic phase was dried, evaporated and purified.

Method E—Synthesis of N-Sulfonyl Piperidine Analogues.

To a solution of 41 (152 mg, 0.5 mmol) in dry THF (5 mL) was added $Et_3N$ (1.3 eq) and the corresponding sulfonyl chloride (1 eq) in dry THF (1 mL). The reaction was stirred for 12 hours, quenched with 1N HCl and filtered to collect the resulting precipitate, which was further purified.

1-(4-Aminopiperidin-1-yl)propan-1-one (1)

4-Aminopiperidine (4.01 g, 40 mmol) and benzaldehyde (4.251 g, 40 mmol) were dissolved in toluene (70 mL) and refluxed on a Dean-Stark trap until water ceased to evolve. The solvent was evaporated and the residue was reconstituted in dry THF (75 mL). Triethylamine (4.04 g, 40 mmol) was added and the reaction was cooled in an ice bath. With vigorous stirring, propionyl chloride (3.70 g, 40 mmol) was added and the reaction continued for 1.5 hours at rt. The reaction was filtered, and the filtrate was evaporated and treated with 1N HCl (50 mL) for 1 hour. The aqueous phase was washed with $Et_2O$ (3×50 mL), basified to pH>10 with NaOH, saturated with sodium chloride and extracted with DCM (5×75 mL). The combined DCM extract was evaporated and azeotropically dried with toluene to give intermediate 1 (4.74 g, 64%) as a light brown oil: $^1$H NMR (500 MHz, DMSO-$d_6$) δ 4.18 (d, J=11.8 Hz, 1H), 3.74 (d, J=11.8 Hz, 1H), 3.00 (dd, J=11.8, 11.8 Hz, 1H), 2.89 (brs, 2H), 2.82-2.15 (m, 1H), 2.67 (dd, J=11.8, 11.8 Hz, 1H), 2.28 (q, J=7.1 Hz, 2H), 1.72 (d, J=11.8 Hz, 1H), 1.67 (d, J=11.8 Hz, 1H), 1.14 (q, J=10.2 Hz, 1H), 1.04 (q, J=10.2 Hz, 1H), 0.98 (t, J=7.1 Hz, 3H).

1-(1-Adamantyl)-3-(1-propionylpiperidin-4-yl)urea (2)

Prepared according to the procedure in *Bioorg. Med. Chem. Lett.*, 2006, 16, 5212-5216. Mp 217-221° C. $^1$H NMR (500 MHz, DMSO-$d_6$) δ 5.67 (d, J=7.6 Hz, 1H), 5.41 (s, 1H), 4.10 (dd, J=12.5 Hz, 1H), 3.69 (d, J=12.5 Hz, 1H), 3.55-3.46 (m, 1H), 3.07 (dd, J=11.5, 11.5 Hz, 1H), 2.79-2.72 (m, 1H), 2.29 (q, J=7.4 Hz, 2H), 1.98 (s, 3H), 1.84 (s, 6H), 1.76 (d, J=12.5 Hz, 1H), 1.70 (d, J=12.5 Hz, 1H), 1.60 (brs, 6H), 1.16 (q, J=11.0 Hz, 1H), 11.06 (q, J=11.0 Hz, 1H), 0.97 (t, J=7.4 Hz, 3H). Purity 95%. HRMS calculated for $C_{19}H_{31}N_3O_2+H^+$ 334.2494. found (ESI(+), [M+H]) 334.2489.

1-Cycloheptyl-3-(1-propionylpiperidin-4-yl)urea (3)

Cycloheptyl isocyanate was reacted with 1 by Method B. Flash chromatography eluted with 15:1 EtOAc:MeOH afforded compound 3 (66 mg, 22%) as a white solid: Mp 164-172° C. $^1$H NMR (500 MHz, DMSO-$d_6$) δ 5.69 (d, J=7.7 Hz, 1H), 5.66 (d, J=7.8 Hz, 1H), 4.13 (d, J=12.8 Hz, 1H), 3.71 (d, J=13.4 Hz, 1H), 3.61-3.52 (m, 2H), 3.07 (t, J=11.7 Hz, 1H), 2.74 (t, J=11.6 Hz, 1H), 2.29 (q, J=7.4 Hz, 2H), 1.80-1.68 (m, 4H), 1.58-1.42 (m, 6H), 1.42-1.28 (m, 4H), 1.25-1.04 (m, 2H), 0.97 (t, J=7.4 Hz, 3H). Purity 92%. HRMS calculated for $C_{16}H_{29}N_3O_2-H^+$ 294.2182. found (ESI(−), [M−H]) 294.2205.

1-Cyclohexyl-3-(1-propionylpiperidin-4-yl)urea (4)

Cyclohexyl isocyanate was reacted with 1 by Method B. Flash chromatography eluted with EtOAc:MeOH (15:1, v:v) afforded compound 4 (63 mg, 22%) as a white solid: Mp 177-179° C. $^1$H NMR (500 MHz, DMSO-$d_6$) δ 5.70 (d, J=7.6 Hz, 1H), 5.62 (d, J=7.9 Hz, 1H), 4.13 (d, J=12.4 Hz, 1H), 3.71 (d, J=14.1 Hz, 1H), 3.57 (s, 1H), 3.34 (s, 1H), 3.07 (t, J=11.8 Hz, 1H), 2.74 (t, J=11.3 Hz, 1H), 2.29 (q, J=7.4 Hz, 2H), 1.81-1.67 (m, 4H), 1.66-1.57 (m, 2H), 1.54-1.46 (m, 1H), 1.30-1.00 (m, 7H), 0.97 (t, J=7.4 Hz, 3H). Purity 97%. HRMS calculated for $C_{15}H_{27}N_3O_2+H^+$ 282.2181. found (ESI(+), [M+H]) 282.2146.

1-Octyl-3-(1-propionylpiperidin-4-yl)urea (5). Octyl isocyanate was prepared from octylamine by Method A and was subsequently reacted with 1 by Method B. Flash chromatography eluted with EtOAc:MeOH (15:1, v:v) afforded compound 5 (145 mg, 47%) as a white solid: Mp 131-132° C. $^1$H NMR (500 MHz, DMSO-$d_6$) δ 5.76 (d, J=7.7 Hz, 1H), 5.69 (t, J=5.2 Hz, 1H), 4.15 (d, J=12.4 Hz, 1H), 3.72 (d, J=13.5 Hz, 1H), 3.61-3.52 (m, 1H), 3.07 (t, J=12.0 Hz, 1H), 2.95 (dd, J=6.5 Hz, 2H), 2.73 (t, J=11.7 Hz, 1H), 2.29 (dd, J=14.8, 7.4 Hz, 2H), 1.80-1.67 (m, 1H), 1.38-1.05 (m, 7H obscured by s, 1.24), 1.24 (s, 8H), 0.97 (t, J=7.4 Hz, 3H), 0.86 (t, J=6.7 Hz, 3H). HRMS calculated for $C_{17}H_{33}N_3O_2+H^+$ 312.2651. found (ESI(+), [M+H]) 312.2601.

1-(trans-2-Phenylcyclopropyl)-3-(1-propionylpiperidin-4-yl)urea (6)

trans-2-Phenylcyclopropyl isocyanate was reacted with 1 by Method B. Flash chromatography eluted with EtOAc:MeOH (15:1, v:v) and recrystallization from EtOAc:acetone afforded compound 6 (178 mg, 57%) as a white solid: Mp 155-158° C. $^1$H NMR (500 MHz, DMSO-$d_6$) δ 7.24 (t, J=7.5

Hz, 2H), 7.14 (t, J=7.4 Hz, 1H), 7.08 (d, J=7.3 Hz, 2H), 6.23 (s, 1H), 5.77 (d, J=7.0 Hz, 1H), 4.16 (d, J=12.9 Hz, 1H), 3.72 (d, J=13.6 Hz, 1H), 3.64-3.54 (m, 1H), 3.06 (t, J=12.0 Hz, 1H), 2.71 (t, J=11.9 Hz, 1H), 2.62 (dt, J=7.3, 3.5 Hz, 1H), 2.29 (q, J=7.4 Hz, 2H), 1.87 (ddd, J=9.0, 6.0, 3.2 Hz, 1H), 1.75 (dd, J=26.8, 11.7 Hz, 2H), 1.23 (q, J=11.6 Hz, 1H), 1.18-1.01 (m, 3H), 0.97 (t, J=7.4 Hz, 3H). Purity 94%. HRMS calculated for $C_{18}H_{25}N_3O_2-H^+$ 314.1869. found (ESI(-), [M-H]) 314.1877.

1-Phenyl-3-(1-propionylpiperidin-4-yl)urea (7)

Phenyl isocyanate was reacted with 1 by Method B. Flash chromatography eluted with 15:1 EtOAc:MeOH afforded compound 6 (112 mg, 41%) as a white solid: Mp 169-171° C. $^1$H NMR (500 MHz, DMSO-$d_6$) δ 8.32 (s, 1H), 7.37 (d, J=8.0 Hz, 2H), 7.21 (t, J=7.8 Hz, 1H), 6.88 (t, J=7.4 Hz, 1H), 6.16 (d, J=7.6 Hz, 1H), 4.18 (d, J=12.7 Hz, 1H), 3.80-3.63 (m, 2H), 3.12 (t, J=12.0 Hz, 1H), 2.79 (t, J=11.6 Hz, 1H), 2.32 (dd, J=7.4 Hz, 2H), 1.88-1.75 (m, 3H), 1.35-1.13 (m, 2H), 0.98 (t, J=7.4 Hz, 3H). Purity 95%. HRMS calculated for $C_{15}H_{21}N_3O_2+276.1712$. found (ESI(+), [M+H]) 276.1658.

1-(Naphthalen-2-yl)-3-(1-propionylpiperidin-4-yl) urea (8)

2-Naphthyl isocyanate was prepared from 2-naphthylamine by Method A and was subsequently reacted with 1 by Method B. Flash chromatography eluted with 17:1 EtOAc:MeOH afforded compound 8 (159 mg, 49%) as a white solid: Mp 213-215° C. $^1$H NMR (500 MHz, DMSO-$d_6$) δ 8.48 (s, 1H), 7.98 (s, 1H), 7.76 (d, J=8.6 Hz, 2H), 7.71 (d, J=8.1 Hz, 1H), 7.46-7.38 (m, 2H), 7.30 (t, J=7.3 Hz, 1H), 6.22 (d, J=7.4 Hz, 1H), 4.17 (s, 1H), 3.75 (s, 2H), 3.17 (s, 1H), 2.84 (s, 1H), 2.32 (dd, J=14.8, 7.5 Hz, 2H), 1.86 (s, 2H), 1.42-1.19 (m, 2H), 1.00 (t, J=7.37 Hz, 3H). Purity 96%. HRMS calculated for $C_{19}H_{23}N_3O_2-H^+$ 324.1712. found (ESI(-), [M-H]) 324.1683.

1-(1-Propionylpiperidin-4-yl)-3-(pyridin-3-yl)urea (9)

Pyridine-3-isocyanate was reacted with 1 by Method B. Flash chromatography eluted with 9:1 EtOAc:MeOH afforded compound 9 (266 mg, 96%) as a colorless oil: $^1$H NMR (500 MHz, DMSO-$d_6$) δ 8.52 (d, J=2.3 Hz, 1H), 8.47 (s, 1H), 8.11 (d, J=4.5 Hz, 1H), 7.86 (d, J=8.8 Hz, 1H), 7.24 (dd, J=8.3, 4.7 Hz, 1H), 6.29 (d, J=7.5 Hz, 1H), 4.18 (d, J=11.9 Hz, 1H), 3.81-3.67 (m, 2H), 3.19-3.09 (m, 1H), 2.80 (t, J=11.6 Hz, 1H), 2.32 (q, J=7.4 Hz, 2H), 1.83 (dd, J=25.1, 12.3 Hz, 2H), 1.39-1.20 (m, 2H), 1.18 (t, J=7.1 Hz, 3H). Purity 83% by $^1$H-NMR. HRMS calculated for $C_{14}H_{20}N_4O_2-H^+$ 275.1508. found (ESI(-), [M-H]) 275.1511.

1-(1-Propionylpiperidin-4-yl)-3-o-tolylurea (10)

o-Tolyl isocyanate was prepared from o-toluidine by Method A and was subsequently reacted with 1 by Method B. Flash chromatography eluted with 16:1 EtOAc:MeOH afforded compound 10 (88 mg, 30%) as a white solid: Mp 178-183° C. $^1$H NMR (500 MHz, DMSO-$d_6$) δ 7.84 (d, J=8.1 Hz, 1H), 7.55 (s, 1H), 7.13-7.05 (m, 2H), 6.85 (t, J=7.4 Hz, 1H), 6.60 (d, J=7.3 Hz, 1H), 4.16 (d, J=13.1 Hz, 1H), 3.75 (d, J=13.8 Hz, 1H), 3.72-3.65 (m, 1H), 3.14 (t, J=11.4 Hz, 1H), 2.82 (t, J=11.1 Hz, 1H), 2.32 (dd, J=14.8, 7.4 Hz, 2H), 2.17 (s, 3H), 1.90-1.77 (m, 2H), 1.35-1.14 (m, 1H), 0.99 (t, J=7.3 Hz, 3H). Purity 95%. HRMS calculated for $C_{16}H_{23}N_3O_2+H^+$ 290.1868. found (ESI(+), [M+H]) 290.1822.

1-Propionylpiperidin-4-yl)-3-m-tolylurea (11)

m-Tolyl isocyanate was prepared from m-toluidine by Method A and was subsequently reacted with 1 by Method B. Flash chromatography eluted with 15:1 EtOAc:MeOH and recrystallization from EtOAc:MeOH afforded compound 11 (74 mg, 26%) as a white solid: Mp 173-175° C. $^1$H NMR (500 MHz, DMSO-$d_6$) δ 8.23 (s, 1H), 7.20 (s, 1H), 7.15 (d, J=8.3 Hz, 1H), 7.08 (t, J=7.7 Hz, 1H), 6.70 (d, J=7.3 Hz, 1H), 6.13 (d, J=7.5 Hz, 1H), 4.17 (d, J=13.5 Hz, 1H), 3.75 (d, J=13.9 Hz, 1H), 3.72-3.63 (m, 1H), 3.12 (t, J=11.8 Hz, 1H), 2.79 (t, J=11.5 Hz, 1H), 2.31 (q, J=7.4 Hz, 2H), 2.23 (s, 3H), 1.88-1.75 (m, 2H), 1.34-1.13 (m, 1H), 0.98 (t, J=7.4 Hz, 3H). Purity 98%. HRMS calculated for $C_{16}H_{23}N_3O_2-H^+$ 288.1712. found (ESI(-), [M-H]) 288.1693.

1-(1-Propionylpiperidin-4-yl)-3-p-tolylurea (12)

p-Tolyl isocyanate was prepared from p-toluidine by Method A and was subsequently reacted with 1 by Method B. Flash chromatography eluted with EtOAc afforded compound 12 (81 mg, 28%) as a white solid: Mp 180-182° C. $^1$H NMR (500 MHz, DMSO-$d_6$) δ 8.20 (s, 1H), 7.25 (d, J=8.3 Hz, 2H), 7.01 (d, J=8.1 Hz, 2H), 6.09 (d, J=7.5 Hz, 1H), 4.17 (d, J=13.5 Hz, 1H), 3.75 (d, J=14.1 Hz, 1H), 3.71-3.63 (m, 1H), 3.12 (t, J=11.6 Hz, 1H), 2.78 (t, J=11.2 Hz, 1H), 2.31 (q, J=7.4 Hz, 2H), 2.21 (s, 3H), 1.88-1.74 (m, 2H), 1.34-1.14 (m, 2H), 0.98 (t, J=7.4 Hz, 3H). Purity 97%. HRMS calculated for $C_{16}H_{23}N_3O_2-H^+$ 288.1712. found (ESI(-), [M-H]) 288.1716.

1-(4-Ethylphenyl)-3-(1-propionylpiperidin-4-yl)urea (13)

4-Ethylphenyl isocyanate was prepared from 4-ethylaniline by Method A and was subsequently reacted with 1 by Method B. Flash chromatography eluted with 17:1 EtOAc:MeOH and recrystallization from acetone afforded compound 13 (46 mg, 15%) as a white solid: Mp 164-165° C. $^1$H NMR (500 MHz, DMSO-$d_6$) δ 8.21 (s, 1H), 7.27 (d, J=8.4 Hz, 2H), 7.04 (d, J=8.4 Hz, 2H), 6.10 (d, J=7.6 Hz, 1H), 4.17 (d, J=13.6 Hz, 1H), 3.75 (d, J=12.9 Hz, 1H), 3.72-3.63 (m, 1H), 3.12 (t, J=12.1 Hz, 1H), 2.79 (t, J=10.9 Hz, 1H), 2.32 (q, J=7.4 Hz, 2H), 1.88-1.74 (m, 2H), 1.34-1.16 (m, 2H), 1.13 (t, J=7.6 Hz, 3H), 0.98 (t, J=7.4 Hz, 3H). Purity 97%. HRMS calculated for $C_{17}H_{25}N_3O_2+H^+$ 304.2025. found (ESI(+), [M+H]) 304.2005.

1-(4-Isopropylphenyl)-3-(1-propionylpiperidin-4-yl) urea (14)

4-Isopropylphenyl isocyanate was prepared from 4-isopropylaniline by Method A and was subsequently reacted with 1 by Method B. Flash chromatography eluted with 15:1 EtOAc:MeOH and recrystallization from acetone afforded compound 14 (44 mg, 14%) as a white solid. Mp 173-174° C. $^1$H NMR (500 MHz, DMSO-$d_6$) δ 8.25-8.18 (m, 1H), 7.27 (d, J=8.4 Hz, 2H), 7.08 (d, J=8.4 Hz, 2H), 6.10 (d, J=7.6 Hz, 1H), 4.17 (d, J=13.2 Hz, 1H), 3.75 (d, J=13.9 Hz, 1H), 3.71-3.63 (m, 1H), 3.16-3.07 (m, 1H), 2.83-2.74 (m, 2H), 2.32 (dd, J=7.4 Hz, 2H), 1.87-1.75 (m, 2H), 1.34-1.18 (m, 2H), 1.16 (d, J=6.9 Hz, 6H), 0.98 (t, J=7.4, 7.4 Hz, 3H). Purity 98%. HRMS calculated for $C_{18}H_{27}N_3O_2-H^+$ 316.2025. found (ESI(-), [M-H]) 316.1981.

1-(4-Methoxyphenyl)-3-(1-propionylpiperidin-4-yl)urea (15)

4-Methoxyphenyl isocyanate was prepared from p-anisidine by Method A and was subsequently reacted with 1 by Method B. Flash chromatography eluted with 15:1 EtOAc:MeOH afforded compound 15 (82 mg, 27%) as a white solid: Mp 164-165° C. $^1$H NMR (500 MHz, DMSO-$d_6$) δ 8.12 (s, 1H), 7.27 (d, J=8.8 Hz, 2H), 6.80 (d, J=8.8 Hz, 2H), 6.04 (d, J=7.6 Hz, 1H), 4.17 (d, J=12.9 Hz, 1H), 3.75 (d, J=13.5 Hz, 1H), 3.69 (s, 3H), 3.68-3.63 (m, 1H, obscured by s δ 3.69), 3.11 (t, J=12.1 Hz, 1H), 2.78 (dd, J=11.4, 11.4 Hz, 1H), 2.31 (dd, J=14.7, 7.3 Hz, 2H), 1.81 (dd, J=26.1, 11.4 Hz, 2H), 1.34-1.14 (m, 2H), 0.98 (t, J=7.3 Hz, 3H). Purity 95%. HRMS calculated for $C_{16}H_{23}N_3O_3+H^+$ 306.1817. found (ESI(+), [M+H]) 306.1780.

1-(4-Phenoxyphenyl)-3-(1-propionylpiperidin-4-yl)urea (16)

4-Phenoxyphenyl isocyanate was prepared from 4-phenoxyaniline by Method A and was subsequently reacted with 1 by Method B. Flash chromatography eluted with EtOAc afforded compound 16 (191 mg, 52%) as a white solid: Mp 153-154° C. $^1$H NMR (500 MHz, DMSO-$d_6$) δ 8.35 (s, 1H), 7.39 (d, J=7.9 Hz, 2H), 7.34 (t, J=7.9, 7.9 Hz, 2H), 7.07 (t, J=7.3 Hz, 1H), 6.92 (d, J=6.8 Hz, 4H), 6.14 (d, J=7.5 Hz, 1H), 4.18 (d, J=12.1 Hz, 1H), 3.76 (d, J=12.8 Hz, 1H), 3.72-3.64 (m, 1H), 3.12 (t, J=12.3 Hz, 1H), 2.79 (t, J=11.7 Hz, 1H), 2.32 (q, J=7.4 Hz, 2H), 1.88-1.76 (m, 2H), 1.35-1.15 (m, 2H), 0.98 (t, J=7.4 Hz, 3H). Purity 96%. HRMS calculated for $C_{21}H_{25}N_3O_3+H^+$ 368.1974. found (ESI(+), [M+H]) 368.1937.

1-(3,4-Methylenedioxyphenyl)-3-(1-propionylpiperidin-4-yl)urea (17)

3,4-Methylenedioxyaniline (274 mg, 2 mmol) was subject to Method C to give the desired urea via an intermediate 4-nitrophenyl carbamate. Flash chromatography eluted with EtOAc afforded compound 17 (238 mg, 37%) as a white solid: Mp 195-197° C. $^1$H NMR (500 MHz, DMSO-$d_6$) δ 8.16 (s, 1H), 7.14 (d, J=1.5 Hz, 1H), 6.75 (d, J=8.3 Hz, 1H), 6.65 (dd, J=8.4, 1.6 Hz, 1H), 6.03 (d, J=7.6 Hz, 1H), 5.92 (s, 1H), 4.16 (d, J=12.3 Hz, 1H), 3.74 (d, J=12.5 Hz, 1H), 3.71-3.62 (m, 1H), 3.12 (t, J=11.6 Hz, 1H), 2.79 (t, J=11.7 Hz, 1H), 2.32 (q, J=7.4 Hz, 2H), 1.81 (dd, J=25.2, 10.6 Hz, 2H), 1.35-1.14 (m, 2H), 0.99 (t, J=7.4 Hz, 3H). Purity 98%. HRMS calculated for $C_{10}H_{21}N_3O_4+H^+$ 320.1610. found (ESI(+), [M+H]) 320.1634.

1-(1-Propionylpiperidin-4-yl)-3-(3,4,5-trimethoxyphenyl)urea (18)

3,4,5-Trimethoxyphenyl isocyanate was prepared from 3,4,5-trimethoxyaniline by Method A and was subsequently reacted with 1 by Method B. Flash chromatography eluted with 15:1 EtOAc:MeOH and recrystallization from EtOAc afforded compound 18 (56 mg, 15%) as a white solid: Mp 173-175° C. $^1$H NMR (500 MHz, DMSO-$d_6$) δ 8.28 (s, 1H), 6.72 (s, 2H), 6.10 (d, J=7.6 Hz, 1H), 4.18 (d, J=13.3 Hz, 1H), 3.76 (d, J=13.9 Hz, 1H), 3.71 (s, 6H), 3.69-3.63 (m, 1H), 3.58 (s, 3H), 3.11 (t, J=11.4 Hz, 1H), 2.78 (t, J=11.2 Hz, 1H), 2.32 (dd, J=7.4, 7.4 Hz, 2H), 1.87-1.75 (m, 2H), 1.35-1.15 (m, 2H), 0.98 (t, J=7.4 Hz, 3H). Purity 99%. HRMS calculated for $C_{18}H_{27}N_3O_2-H^+$ 364.1873. found (ESI(-), [M-H]) 364.1906.

1-(4-Morpholinophenyl)-3-(1-propionylpiperidin-4-yl)urea (19)

4-Morpholinophenyl isocyanate was prepared from 4-morpholinoaniline by Method A using 1M NaOH in brine as the base and was subsequently reacted with 1 by Method B. Flash chromatography eluted with 9:1 EtOAc:MeOH afforded compound 19 (61 mg, 17%) as a white solid: Mp 221-225° C. $^1$H NMR (500 MHz, DMSO-$d_6$) δ 8.06 (s, 1H), 7.23 (d, J=8.9 Hz, 2H), 6.83 (d, J=8.9 Hz, 2H), 6.03 (d, J=7.6 Hz, 1H), 4.17 (d, J=13.5 Hz, 1H), 3.79-3.73 (obscured d, 1H), 3.71 (t, J=12.2 Hz, 4H), 3.69-3.62 (m, 1H), 3.11 (t, J=12.2 Hz, 1H), 2.98 (t, 4H), 2.78 (t, J=11.7 Hz, 1H), 2.31 (q, J=7.4 Hz, 2H), 1.87-1.75 (m, 2H), 1.34-1.13 (m, 2H), 0.98 (t, J=7.4 Hz, 3H). Purity 93%. HRMS calculated for $C_{19}H_{28}N_4O_3+H^+$ 359.2083. found (ESI(+), [M+H]) 359.2068.

1-(4-Nitrophenyl)-3-(1-propionylpiperidin-4-yl)urea (20)

4-Nitrophenyl isocyanate was reacted with 1 by Method B. Flash chromatography eluted with 15:1 EtOAc:MeOH afforded compound 20 (122 mg, 38%) as a white solid: Mp 240-241° C. $^1$H NMR (500 MHz, DMSO-$d_6$) δ 9.15 (s, 1H), 8.14 (d, J=9.2 Hz, 2H), 7.61 (d, J=9.2 Hz, 2H), 6.49 (d, J=7.5 Hz, 1H), 4.20 (d, J=13.2 Hz, 1H), 3.80-3.68 (m, 2H), 3.13 (t, J=12.8 Hz, 1H), 2.79 (t, J=11.9 Hz, 1H), 2.32 (q, J=7.4 Hz, 2H), 1.83 (dd, J=25.2, 12.5 Hz, 2H), 1.39-1.19 (m, 2H), 0.98 (t, J=7.4 Hz, 3H). Purity 95%. HRMS calculated for $C_{15}H_{20}N_4O_4-H^+$ 319.1407. found (ESI(-), [M-H]) 319.1410.

Methyl 4-(3-(1-propionylpiperidin-4-yl)ureido)benzoate (21)

Methyl 4-isocyanatobenzoate was reacted with 1 by Method B. Flash chromatography eluted with 15:1 EtOAc:MeOH afforded compound 21 (271 mg, 82%) as a white solid: Mp 201-204° C. $^1$H NMR (500 MHz, DMSO-$d_6$) δ 8.79 (s, 1H), 7.83 (d, J=8.8 Hz, 2H), 7.50 (d, J=8.8 Hz, 2H), 6.34 (d, J=7.5 Hz, 1H), 4.18 (d, J=13.0 Hz, 1H), 3.80 (s, 3H), 3.78-3.65 (m, 2H), 3.13 (t, J=11.9 Hz, 1H), 2.79 (t, J=11.9 Hz, 1H), 2.32 (q, J=7.4 Hz, 2H), 1.83 (dd, J=-25.29, 11.74 Hz, 2H), 1.38-1.27 (m, 1H), 1.27-1.16 (m, 1H), 0.98 (t, J=7.4 Hz, 3H). Purity 96%. HRMS calculated for $C_{17}H_{23}N_3O_4-H^+$ 332.1611. found (ESI(-), [M-H]) 332.1595.

4-(3-(1-Propionylpiperidin-4-yl)ureido)benzoic acid (22)

Compound 21 (85 mg, 0.25 mmol) was refluxed in ethanol (10 mL) containing 1M NaOH (300 μl, 1.2 eq) for 5 hours. Additional base (300 μl) was added and the reaction continued for 2 hours before cooling to RT The reaction was quenched with 1N HCl (20 mL), the organic solvent removed and the remaining suspension filtered to give compound 22 (49 mg, 60%) as a white solid: MP 201-204° C. $^1$H NMR (500 MHz, DMSO-$d_6$) δ 12.50 (s, 1H), 8.73 (s, 1H), 7.80 (d, J=8.7 Hz, 2H), 7.47 (d, J=8.7 Hz, 2H), 6.32 (d, J=7.6 Hz, 1H), 3.13 (t, J=12.1 Hz, 1H), 2.80 (t, J=11.8 Hz, 1H), 2.32 (q, J=7.4 Hz, 2H), 0.98 (t, J=7.4 Hz, 3H). Purity 94%. HRMS calculated for $C_{16}H_{21}N_3O_4-H^+$ 318.1454. found (ESI(-), [M-H]) 318.1498.

1-(4-Hydroxyphenyl)-3-(1-propionylpiperidin-4-yl)urea (23)

4-Benzyloxyphenyl isocyanate was prepared from 4-benzyloxyanline by Method A and was subsequently reacted with 1 by Method B. Flash chromatography eluted with EtOAc gave intermediate 1-(4-benzyloxyphenyl)-3-(1-propionylpiperidin-4-yl)urea, which was dissolved in ethanol and hydrogenolyzed with 10% palladium on charcoal under an atmosphere of hydrogen. Flash chromatography eluted with 15:1 DCM:MeOH gave compound 23 (13 mg, 5% overall) as a white solid: Mp 229-230° C. $^1$H NMR (500 MHz, DMSO-$d_6$) δ 8.92 (s, 1H), 7.97 (s, 1H), 7.13 (d, J=8.6 Hz, 2H), 6.62 (d, J=8.7 Hz, 2H), 6.00-5.97 (m, 1H), 4.17 (d, J=12.5 Hz, 1H), 3.75 (d, J=14.3 Hz, 1H), 3.70-3.62 (m, 1H), 3.11 (t, J=12.1 Hz, 1H), 2.81-2.74 (m, 1H), 2.31 (q, J=7.5 Hz, 2H), 1.80 (dd, J=26.6, 12.1 Hz, 2H), 1.33-1.23 (m, 1H), 1.23-1.13 (m, 1H), 0.98 (t, J=7.4 Hz, 3H). Purity 100%. HRMS calculated for $C_{15}H_{21}N_3O_3+H^+$ 292.1661. found (ESI (+), [M+H]) 292.1618.

1-(4-Fluorophenyl)-3-(1-propionylpiperidin-4-yl) urea (24)

4-Fluorophenyl isocyanate was prepared from 4-fluoroaniline by Method A and was subsequently reacted with 1 by Method B. Flash chromatography eluted with EtOAc afforded compound 24 (106 mg, 36%) as a white solid: Mp 183-184° C. $^1$H NMR (500 MHz, DMSO-$d_6$) δ 8.36 (s, 1H), 7.40-7.35 (m, 2H), 7.08-7.02 (m, 1H), 6.14 (d, J=7.6 Hz, 1H), 4.18 (d, J=13.1 Hz, 1H), 3.75 (d, J=13.9 Hz, 1H), 3.72-3.64 (m, 1H), 3.12 (t, J=12.1 Hz, 1H), 2.78 (t, J=11.3 Hz, 1H), 2.32 (dd, J=7.4 Hz, 2H), 1.88-1.75 (m, 2H), 1.36-1.14 (m, 2H), 0.98 (t, J=7.4 Hz, 3H). Purity 100%. HRMS calculated for $C_{15}H_{20}FN_3O_2-H^+$ 292.1462. found (ESI(-), [M-H]) 292.1444.

1-(4-Chlorophenyl)-3-(1-propionylpiperidin-4-yl) urea (25)

4-Chlorophenyl isocyanate was reacted with 1 by Method B. Flash chromatography eluted with 15:1 EtOAc:MeOH and recrystallization from acetone:hexane afforded compound 25 (53 mg, 17%) as a white solid: Mp 225-226° C. $^1$H NMR (500 MHz, DMSO-$d_6$) δ 8.54 (s, 1H), 7.41 (d, J=8.8 Hz, 2H), 7.25 (d, J=8.8 Hz, 2H), 6.26 (d, J=7.6 Hz, 1H), 4.17 (d, J=13.0 Hz, 1H), 3.75 (d, J=13.6 Hz, 1H), 3.72-3.64 (m, 1H), 3.12 (t, J=11.23 Hz, 1H), 2.79 (t, J=11.0 Hz, 1H), 2.31 (q, J=7.4 Hz, 2H), 1.88-1.74 (m, 2H), 1.37-1.15 (m, 2H), 0.98 (t, J=7.4 Hz, 3H). Purity 96%. HRMS calculated for $C_{15}H_{20}ClN_3O_2-H^+$ 308.1166. found (ESI(-), [M-H]) 308.1152.

1-(4-Bromophenyl)-3-(1-propionylpiperidin-4-yl) urea (26)

4-Bromophenyl isocyanate was reacted with 1 by Method B. Flash chromatography eluted with EtOAc afforded compound 26 (201 mg, 57%) as a white solid: Mp 233-239° C. $^1$H NMR (500 MHz, DMSO-$d_6$) δ 8.48 (s, 1H), 7.40-7.33 (m, 4H), 6.21 (d, J=7.6 Hz, 1H), 4.18 (d, J=13.0 Hz, 1H), 3.75 (d, J=13.8 Hz, 1H), 3.72-3.64 (m, 1H), 3.12 (t, J=12.1 Hz, 1H), 2.78 (t, J=11.8 Hz, 1H), 2.31 (q, J=7.3 Hz, 2H), 1.81 (dd, J=25.9, 12.2 Hz, 2H), 1.36-1.15 (m, 2H), 0.98 (t, J=7.4 3H). Purity 94%. HRMS calculated for $C_{15}H_{20}BrN_3O_2+H^+$ 354.0817. found (ESI(+), [M+H]) 354.0774.

1-(4-Iodophenyl)-3-(1-propionylpiperidin-4-yl)urea (27)

4-Iodophenyl isocyanate was prepared on a 2 mmol scale from 4-iodoaniline by Method A and was subsequently reacted with 1 by Method B. Trituration twice from 1:1 EtOAc:MeOH, flash chromatography eluted with 8:1 EtOAc:MeOH and recrystallization from acetone:MeOH afforded compound 27 (39 mg, 5%) as a white solid: Mp 246-247° C. $^1$H NMR (500 MHz, DMSO-$d_6$) δ 8.46 (s, 1H), 7.52 (d, J=8.7 Hz, 2H), 7.23 (d, J=8.7 Hz, 2H), 6.21 (d, J=7.6 Hz, 1H), 4.17 (d, J=12.9 Hz, 1H), 3.75 (d, J=14.3 Hz, 1H), 3.72-3.63 (m, 1H), 3.16-3.06 (m, 1H), 2.82-2.73 (m, 1H), 2.31 (q, J=7.4 Hz, 2H), 1.87-1.74 (m, 2H), 1.35-1.14 (m, 2H), 0.98 (t, J=7.4 Hz, 3H). Purity 95%. HRMS calculated for $C_{15}H_{20}IN_3O_2-H^+$ 400.0522. found (ESI(-), [M-H]) 400.0488.

1-(3-Fluorophenyl)-3-(1-propionylpiperidin-4-yl) urea (28)

3-Fluorophenyl isocyanate was reacted with 1 by Method B. Flash chromatography eluted with EtOAc afforded compound 28 (231 mg, 79%) as a white solid: Mp 158-164° C. $^1$H NMR (500 MHz, DMSO-$d_6$) δ 8.57 (s, 1H), 7.44 (d, $J_{HF}$=12.2 Hz, 1H), 7.23 (q, J=7.9 Hz, 1H), 7.00 (d, J=8.4 Hz, 1H), 6.69 (t, J=8.3 Hz, 1H), 6.25 (d, J=7.5 Hz, 1H), 4.18 (d, J=13.0 Hz, 1H), 3.76 (d, J=13.7 Hz, 1H), 3.72-3.64 (m, 1H), 3.12 (t, J=12.2 Hz, 1H), 2.78 (t, J=11.9 Hz, 1H), 2.32 (q, J=7.3 Hz, 2H), 1.82 (dd, J=25.8, 12.3 Hz, 2H), 1.31 (q, J=11.4 Hz, 1H), 1.21 (q, J=11.1 Hz, 1H), 0.98 (t, J=7.3 Hz, 3H). Purity 97%. HRMS calculated for $C_{15}H_{20}FN_3O_2-H^+$ 294.1608. found (ESI(-), [M-H]) 294.1587.

1-(2-Fluorophenyl)-3-(1-propionylpiperidin-4-yl) urea (29)

The reaction of 2-fluorophenyl isocyanate with 1 in the same manner as for compound 27 afforded compound 29 (118 mg, 40%) as a white solid: Mp 127-130° C. $^1$H NMR (500 MHz, DMSO-$d_6$) δ 8.19 (d, J=1.3 Hz, 1H), 8.12 (dt, J=8.3, 1.0 Hz, 1H), 7.19-7.14 (m, 1H), 7.07 (t, J=7.8 Hz, 1H), 6.94-6.88 (m, 1H), 6.69 (d, J=7.4 Hz, 1H), 4.12 (d, J=13.1 Hz, 1H), 3.77-3.66 (m, 2H), 3.15 (t, J=11.5 Hz, 1H), 2.86 (t, J=11.5 Hz, 1H), 2.32 (q, J=7.4 Hz, 2H), 1.83 (dd, J=25.9, 11.9 Hz, 2H), 1.34-1.25 (m, 1H), 1.25-1.14 (m, 1H), 0.98 (t, J=7.4 Hz, 3H). Purity 94%. HRMS calculated for $C_{15}H_{20}FN_3O_2-H^+$ 2924.1608. found (ESI(-), [M-H]) 294.1589.

1-(3-Chlorophenyl)-3-(1-propionylpiperidin-4-yl) urea (30)

3-Chlorophenyl isocyanate was reacted with 1 by Method B. Flash chromatography eluted with EtOAc afforded compound 30 (116 mg, 38%) as a white solid: Mp 165-166° C. $^1$H NMR (500 MHz, DMSO-$d_6$) δ 8.56 (s, 1H), 7.66 (t, J=1.9 Hz, 1H), 7.23 (t, J=8.0 Hz, 1H), 7.16 (d, J=8.0 Hz, 1H), 6.93 (dq, J=8.0, 1.0 Hz, 1H), 6.26 (d, J=7.6 Hz, 1H), 4.19 (brd, J=13.3 Hz, 1H), 3.76 (brd, J=13.3 Hz, 1H), 3.72-3.64 (m, 1H), 3.12 (dd, J=11.4, 11.4 Hz, 1H), 2.78 (dd, J=11.4, 11.4 Hz, 1H), 2.32 (q, J=7.4 Hz, 2H), 1.84 (d, J=1.84 Hz, 1H), 1.79 (d, J=12.5 Hz, 1H), 1.33 (dq, J=11.5, 3.8 Hz, 2H), 1.21 (dq, J=11.5, 3.8 Hz, 2H), 0.98 (t, J=7.4 Hz, 3H). Purity 97%. HRMS calculated for $C_{15}H_{20}ClN_3O_2-H^+$ 308.1166. found (ESI(-), [M-H]) 308.1111.

1-(2-Chlorophenyl)-3-(1-propionylpiperidin-4-yl) urea (31)

2-Chloroaniline (128 mg, 1 mmol) was subject to Method C. Flash chromatography eluted with EtOAc afforded compound 31 (48 mg, 16%) as a white solid: Mp 150-157° C. $^1$H NMR (500 MHz, DMSO-$d_6$) δ 8.16 (d, J=8.2 Hz, 1H), 7.91 (s, 1H), 7.38 (d, J=7.9 Hz, 1H), 7.22 (t, J=7.7 Hz, 1H), 7.05 (d, J=7.2 Hz, 1H), 6.94 (t, J=7.4 Hz, 1H), 4.12 (d, J=12.2 Hz, 1H), 3.79-3.67 (m, 2H), 3.16 (t, J=11.4 Hz, 1H), 2.88 (t, J=11.2 Hz, 1H), 2.32 (q, J=7.4 Hz, 2H), 1.85 (dd, J=26.0, 11.4 Hz, 2H), 1.37-1.16 (m, 2H), 0.99 (t, J=7.4 Hz, 3H). Purity 92%. HRMS calculated for $C_{15}H_{20}ClN_3O_2+H^+$ 310.1322. found (ESI(+), [M+H]) 310.1311.

1-(3,4-Dichlorophenyl)-3-(1-propylpiperidin-4-yl)urea (32)

3,4-Dichlorophenyl isocyanate was prepared from 3,4-dichloroaniline by Method A (using NaOH and brine as the base) and was subsequently reacted with 1 by Method B. Flash chromatography eluted with 17:1 EtOAc:MeOH and recrystallization from EtOAc afforded compound 32 (68 mg, 20%) as a white solid: Mp 198-200° C. $^1$H NMR (500 MHz, DMSO-$d_6$) δ 8.67 (s, 1H), 7.82 (s, 1H), 7.44 (d, J=8.8 Hz, 1H), 7.23 (d, J=8.5 Hz, 1H), 6.32 (d, J=7.8 Hz, 1H), 4.19 (d, J=13.1 Hz, 1H), 3.76 (d, J=13.8 Hz, 1H), 3.73-3.64 (m, 1H), 3.11 (t, J=11.8 Hz, 1H), 2.77 (t, J=12.1 Hz, 1H), 2.32 (q, J=7.4 Hz, 2H), 1.87-1.75 (m, 2H), 1.37-1.16 (m, 2H), 0.98 (t, J=7.3 Hz, 3H). Purity 98%. HRMS calculated for $C_{15}H_{19}Cl_2N_3O_2+H^+$ 342.0776. found (ESI(+), [M+H]) 342.0757.

1-(3,5-Dichlorophenyl)-3-(1-propylpiperidin-4-yl)urea (33)

3,5-Dichlorophenyl isocyanate was prepared from 3,5-dichloroaniline by Method A and subsequently reacted with 1 by Method B. Flash chromatography eluted with EtOAc and recrystallization from EtOAc:acetone afforded compound 33 (22 mg, 6%) as a white solid: Mp 196-198° C. $^1$H NMR (500 MHz, DMSO-$d_6$) δ 8.74 (s, 1H), 7.46 (d, J=1.5 Hz, 2H), 7.07 (t, J=1.5 Hz, 1H), 6.40 (d, J=7.6 Hz, 1H), 4.20 (d, J=13.0 Hz, 1H), 3.77 (d, J=13.2 Hz, 1H), 3.73-3.64 (m, 1H), 3.11 (t, J=12.1 Hz, 1H), 2.75 (t, J=11.9 Hz, 1H), 2.31 (q, J=7.5 Hz, 2H), 1.81 (dd, J=25.8, 12.0 Hz, 2H), 1.37-1.16 (m, 2H), 0.98 (t, J=7.4 Hz, 3H). Purity 100%. HRMS calculated for $C_{15}H_{19}Cl_2N_3O_2+H^+$ 344.0932. found (ESI(+), [M+H]) 344.0897.

1-(2,6-Dichlorophenyl)-3-(1-propylpiperidin-4-yl)urea (34)

2,6-Dichlorophenyl isocyanate was reacted with 1 by Method B. Flash chromatography eluted with EtOAc afforded compound 34 (229 mg, 67%) as a white solid: Mp 170-174° C. $^1$H NMR (500 MHz, DMSO-$d_6$) δ 7.87 (s, 1H), 7.47 (d, J=8.1 Hz, 2H), 7.25 (t, J=8.1 Hz, 1H), 6.38 (d, J=7.8 Hz, 1H), 4.20 (d, J=13.2 Hz, 1H), 3.77 (d, J=13.0 Hz, 1H), 3.70-3.60 (m, 1H), 3.15-3.05 (m, 1H), 2.75 (t, J=11.4 Hz, 1H), 2.31 (q, J=7.3 Hz, 2H), 1.89-1.75 (m, 2H), 1.38-1.16 (m, 2H), 0.98 (t, J=7.4 Hz, 3H). Purity 95%. HRMS calculated for $C_{15}H_{19}Cl_2N_3O_2-H^+$ 342.0776. found (ESI(-), [M-H]) 342.0801.

1-(4-Chloro-3-(trifluoromethyl)phenyl)-3-(1-propionylpiperidin-4-yl)urea (35)

4-Chloro-3-(trifluoromethyl)phenyl isocyanate was reacted with 1 by Method B. Flash chromatography eluted with EtOAc and recrystallization from EtOAc afforded compound 35 (89 mg, 24%) as a white solid: Mp 182-184° C. $^1$H NMR (500 MHz, DMSO-$d_6$) δ 8.85 (s, 1H), 8.06 (s, 1H), 7.54 (s, 2H), 6.37 (d, J=7.6 Hz, 1H), 4.20 (d, J=13.2 Hz, 1H), 3.77 (d, J=13.9 Hz, 1H), 3.70 (s, 1H), 3.11 (t, J=11.8 Hz, 1H), 2.76 (t, J=11.9 Hz, 1H), 2.32 (q, J=7.4 Hz, 2H), 1.88-1.74 (m, 2H), 1.38-1.28 (m, 1H), 1.28-1.17 (m, 1H), 0.98 (t, J=7.4 Hz, 3H). Purity 95%. HRMS calculated for $C_{16}H_{19}ClF_3N_3O_2+H^+$ 378.1196. found (ESI(+), [M+H]) 378.1198.

1-(1-Propionylpiperidin-4-yl)-3-(4-(trifluoromethyl)phenyl)urea (36)

4-Trifluoromethylphenyl isocyanate was reacted with 1 by Method B. Recrystallization from EtOAc:hexanes afforded compound 36 (166 mg, 48%) as a white solid: Mp 224-228° C. $^1$H NMR (500 MHz, DMSO-$d_6$) δ 8.78 (s, 1H), 7.61-7.54 (m, 4H), 6.33 (d, J=7.5 Hz, 1H), 4.19 (d, J=12.9 Hz, 1H), 3.83-3.62 (m, 2H), 3.32 (s, 1H), 3.13 (t, J=11.7 Hz, 1H), 2.79 (t, J=11.8 Hz, 1H), 2.32 (dd, J=14.8, 7.4 Hz, 2H), 1.92-1.72 (m, 1H), 1.37-1.15 (m, 2H), 0.98 (t, J=7.4 Hz, 3H). Purity 94%. HRMS calculated for $C_{16}H_{20}F_3N_3O_2-H^+$ 342.1430. found (ESI(-), [M-H]) 342.1404.

1-(1-Propionylpiperidin-4-yl)-3-(3-(trifluoromethyl)phenyl)urea (37)

3-Trifluoromethylphenyl isocyanate was reacted with 1 by Method B. Flash chromatography eluted with EtOAc and recrystallization from EtOAc:hexanes afforded compound 37 (30 mg, 9%) as a white solid: Mp 153-154° C. $^1$H NMR (500 MHz, DMSO-$d_6$) δ 8.72 (s, 1H), 7.96 (s, 1H), 7.50-7.41 (m, 2H), 7.22 (d, J=6.9 Hz, 1H), 6.31 (d, J=7.4 Hz, 1H), 4.20 (d, J=13.1 Hz, 1H), 3.80-3.73 (m, 1H), 3.74-3.65 (m, 1H), 3.12 (t, J=11.9 Hz, 1H), 2.77 (t, J=11.6 Hz, 1H), 2.32 (q, J=7.4 Hz, 2H), 1.88-1.76 (m, 2H), 1.38-1.18 (m, 2H), 0.98 (t, J=7.4 Hz, 3H). Purity 98%. HRMS calculated for $C_{16}H_{20}F_3N_3O_2-H^+$ 342.1430. found (ESI(-), [M-H]) 342.1419.

1-(4-Perfluoroisopropylphenyl)-3-(1-propionylpiperidin-4-yl)urea (38)

4-Perfluoroisopropylaniline was prepared as described previously (J. Org. Chem. 1996, 61, 3929-3934) and converted to the corresponding isocyanate by Method A using NaOH in brine as the base and was subsequently reacted with 1 by Method B. Flash chromatography eluted with EtOAc and recrystallization from EtOAc:hexanes afforded compound 38 (43 mg, 10%) as a white solid: Mp 160-164° C. dec. $^1$H NMR (500 MHz, DMSO-$d_6$) δ 8.77 (s, 1H), 7.61 (d, J=8.7 Hz, 2H), 7.50 (d, J=8.6 Hz, 2H), 6.32 (d, J=7.4 Hz, 1H), 4.19 (d, J=12.6 Hz, 1H), 3.76 (d, J=14.0 Hz, 1H), 3.73-3.66 (m, 1H), 3.13 (t, J=12.3 Hz, 1H), 2.79 (t, J=12.0 Hz, 1H), 2.32 (q, J=7.3 Hz, 2H), 1.83 (dd, J=25.7, 13.1 Hz, 2H), 1.37-1.17 (m, 2H), 0.98 (t, J=7.4 Hz, 3H). Purity 100%. HRMS calculated for $C_{18}H_{20}F_7N_3O_2+H^+$ 444.1522. found (ESI(+), [M+H]) 444.1505.

1-(2-Methyl-4-perfluoroisopropylphenyl)-3-(1-propionylpiperidin-4-yl)urea (39)

2-Methyl-4-perfluoroisopropylaniline (J. Org. Chem. 1996, 61, 3929-3934) and compound 39 (41 mg, 9%) were prepared as for compound 38: Mp 226-229° C. $^1$H NMR (500 MHz, DMSO-$d_6$) δ 8.23 (d, J=8.6 Hz, 1H), 7.84 (s, 1H), 7.40-7.35 (m, 2H), 6.87 (d, J=7.2 Hz, 1H), 4.16 (d, J=12.8 Hz, 1H), 3.80-3.67 (m, 2H), 3.15 (t, J=12.2 Hz, 1H), 2.84 (t, J=11.7 Hz, 1H), 2.33 (q, J=7.2 Hz, 2H), 2.26 (s, 3H), 1.86 (dd, J=27.2, 12.2 Hz, 1H), 1.36-1.27 (m, 1H), 1.27-1.15 (m, 1H), 0.99 (t, J=7.4 Hz, 3H). Purity 100%. HRMS calculated for $C_{19}H_{22}F_7N_3O_2-H^+$ 456.1522. found (ESI(-), [M-H]) 456.1512.

1-(1-Propionylpiperidin-4-yl)-3-(4-(trifluoromethoxy)phenyl)urea (40)

To an ice cold solution of intermediate 41 (242 mg, 0.84 mmol) in DCM (5 mL) was added triethylamine (2504, 1.8 mmol) followed by propionyl chloride (95 μL, 1.1 mmol). The reaction was allowed to warm to rt and was stirred for 5 hours. Flash chromatography eluted with 15:1 EtOAc:MeOH afforded compound 40 (178 mg, 63%) as a white solid: Mp 195-196° C. $^1$H NMR (500 MHz, DMSO-d$_6$) δ 8.55 (s, 1H), 7.47 (d, J=8.9 Hz, 2H), 7.22 (d, J=8.6 Hz, 2H), 6.23 (d, J=7.6 Hz, 1H), 4.18 (d, J=12.8 Hz, 1H), 3.76 (d, J=13.6 Hz, 1H), 3.73-3.65 (m, 1H), 3.12 (t, J=11.4 Hz, 1H), 2.78 (t, J=11.0 Hz, 1H), 2.32 (q, J=7.4 Hz, 2H), 1.82 (dd, J=25.3, 12.1 Hz, 2H), 1.36-1.15 (m, 2H), 0.98 (t, J=7.4 Hz, 3H). Purity 97%. HRMS calculated for $C_{16}H_{20}F_3N_3O_3$–H$^+$ 358.1379. found (ESI(–), [M–H]) 358.1404.

tert-Butyl 4-(3-(4-(trifluoromethoxy)phenyl)ureido)piperidine-1-carboxylate (41)

4-Trifluoromethoxyphenyl isocyanate (1.03 g, 5 mmol) was dissolved in dry THF (10 mL) and cooled in an ice bath. A solution of N—BOC-4-aminopiperidine (781 mg, 5 mmol) in dry THF (10 mL) was slowly added. The reaction was allowed to warm to RT and stir for 12 hours. The solvent was removed and the residue chromatographed from ethyl acetate to give intermediate 41 (1.71 g, 95%) as a white solid: Mp 160-162° C. $^1$H NMR (500 MHz, DMSO-d$_6$) δ 8.54 (s, 1H), 7.47 (d, J=9.0 Hz, 2H), 7.21 (d, J=8.6 Hz, 2H), 6.22 (d, J=7.6 Hz, 1H), 3.81 (d, J=13.0 Hz, 2H), 3.67-3.59 (m, 1H), 2.90 (s, 2H), 1.79 (dd, J=12.6, 2.5 Hz, 2H), 1.40 (s, 9H), 1.25 (dq, J=12.1, 3.9 Hz, 2H). HRMS calculated for $C_{18}H_{24}F_3N_3O_4$–H$^+$ 402.1641. found (ESI(–), [M–H]) 402.1612.

1-(Piperidin-4-yl)-3-(4-(trifluoromethoxy)phenyl) urea (42)

Intermediate 41 (2.02 g, 5.0 mmol) was treated with 1M HCl in methanol (35 mL) and refluxed for 3 hours. The solvent was evaporated and the residue diluted with 1N NaOH. The resulting precipitate was removed by filtration and further dried under high vacuum to give intermediate 42 (1.35 g, 89%) as a white solid: Mp 169-173° C. $^1$H NMR (500 MHz, DMSO-d$_6$) δ 8.49 (s, 1H), 7.46 (d, J=9.0 Hz, 2H), 7.21 (d, J=8.6 Hz, 2H), 6.15 (d, J=7.7 Hz, 1H), 3.55-3.45 (m, 1H), 2.89 (td, J=12.8, 3.5 Hz, 2H), 2.49-2.45 (m, 2H), 2.13 (s, 1H), 1.74 (dd, J=12.4, 2.4 Hz, 2H), 1.21 (dq, J=11.7, 3.7 Hz, 2H). HRMS calculated for $C_{13}H_{16}F_3N_3O_2$–H$^+$ 302.1117. found (ESI(–), [M–H]) 302.1114.

Propyl 3,4,5-tribenzyloxybenzoate (43)

Prepared according to *J. Med. Chem.* 2006, 49, 2829-2837. $^1$H NMR (500 MHz, CDCl$_3$) δ 7.43 (d, J=7.2 Hz, 4H), 7.41-7.30 (m, 10H), 7.30-7.23 (m, 3H), 5.14 (s, 4H), 5.12 (s, 2H), 4.24 (t, J=6.7 Hz, 2H), 1.81-1.72 (sxt, 2H), 1.01 (t, J=7.4 Hz, 3H).

3,4,5-Tribenzyloxybenzoic acid (44)

Prepared according to *J. Med. Chem.* 2006, 49, 2829-2837.

Ethyl (4-benzyl-piperazin-1-yl)acetate (45)

Prepared according to *J. Med. Chem.* 2003, 46, 1918-1930. $^1$H NMR (500 MHz, DMSO-d$_6$, 50° C.) δ 7.33-7.19 (m, 5H), 4.08 (q, J=7.1 Hz, 2H), 3.45 (s, 2H), 3.17 (s, 2H), 2.51 (dd, J=4.5, 4.5 Hz, 2H) 2.50-2.45 (m, 2H), 2.37 (dd, J=4.5, 4.5 Hz, 4H), 1.18 (t, J=7.1 Hz, 3H).

(4-Benzyl-piperazin-1-yl)acetic acid (46)

Prepared according to *J. Med. Chem.* 2003, 46, 1918-1930. $^1$H NMR (500 MHz, DMSO-d$_6$) δ 7.32 (tt, J=6.9, 1.4, 2H) 7.29 (d, J=6.9 Hz, 2H) 7.24 (t, J=6.9 Hz, 1H), 3.46 (s, 2H), 3.13 (s, 2H), 2.64 (brs, 4H), 2.42 (brs, 4H).

1-(1-Isonicotinoylpiperidin-4-yl)-3-(4-(trifluoromethoxy)phenyl)urea (47)

Intermediate 42 (152 mg, 0.5 mmol) was reacted with isonicotinic acid by Method E. Flash chromatography eluted with 9:1 DCM:MeOH afforded compound 47 (204 mg, 100%) as a white solid: Mp 210-212° C. $^1$H NMR (500 MHz, DMSO-d$_6$) δ 8.67 (d, J=6 Hz, 2H), 8.59 (s, 1H), 7.47 (d, J=9 Hz, 2H), 7.38 (d, J=6 Hz, 2H), 7.22 (d, J=9 Hz, 2H), 6.25 (d, J=8 Hz, 1H), 4.30 (d, J=12 Hz, 1H), 3.76 (s, 1H), 3.41 (d, J=12 Hz, 1H), 3.16 (t, J=12 Hz, 1H), 3.05 (t, J=12 Hz, 1H), 1.97-1.88 (m, 1H), 1.84-1.75 (m, 1H), 1.47-1.29 (m, 2H). Purity 92%. HRMS calculated for $C_{19}H_{19}F_3N_4O_3$–H$^+$ 407.1331. found (ESI(–), [M–H]) 407.1316.

1-(1-(6-Chloronicotinoyl)piperidin-4-yl)-3-(4-(trifluoromethoxy)phenyl) urea (48)

The reaction of 42 with 6-chloronicotinic in the same manner as for compound 46 afforded compound 48 (220 mg, 100%) as a white solid: Mp 208-209° C. $^1$H NMR (500 MHz, DMSO-d$_6$) δ 8.54 (s, 1H), 8.46 (d, J=2 Hz, 1H), 7.90 (dd, J=8, 2 Hz, 1H), 7.60 (d, J=8 Hz, 1H), 7.47 (d, J=9 Hz, 2H), 7.20 (d, J=9 Hz, 2H), 6.22 (d, J=7 Hz, 1H), 4.28 (s, 1H), 3.76 (s, 1H), 3.50 (s, 1H), 3.26-3.02 (m, 2H), 1.87 (s, 2H), 1.40 (s, 2H). Purity 94%. HRMS calculated for $C_{19}H_{18}ClF_3N_4O_3$–H$^+$ 441.0942. found (ESI(–), [M–H]) 441.0942.

1-(((Pyridin-2-yl)acetyl)piperidin-4-yl)-3-(4-(trifluoromethoxy)phenyl) urea (49)

The reaction of 42 with 2-pyridyl acetic acid in the same manner as for compound 46 afforded compound 49 (196 mg, 93%) as a white solid: Mp 183-187° C. $^1$H NMR (500 MHz, DMSO-d$_6$) δ 8.48 (d, J=4.3 Hz, 1H), 8.43 (s, 1H), 7.73 (dt, J=7.7, 1.7 Hz, 1H), 7.46 (d, J=9.0 Hz, 2H), 7.28 (d, J=7.8 Hz, 1H), 7.26-7.22 (m, 1H), 7.19 (d, J=8.6 Hz, 2H), 6.17 (d, J=7.5 Hz, 1H), 4.16 (d, J=12.0 Hz, 1H), 3.91 (d, J=13.3 Hz, 1H), 3.87 (s, 2H), 3.74-3.65 (m, 1H), 3.20-3.14 (m, 1H), 2.86 (t, J=11.9 Hz, 1H), 1.84-1.75 (m, 2H), 1.27-1.15 (m, 2H). Purity 91%. HRMS calculated for $C_{20}H_{21}F_3N_4O_3$–H$^+$ 421.1488. found (ESI(–), [M–H]) 421.1477.

1-(1-(2-(4-Benzylpiperazin-1-yl)acetyl)piperidin-4-yl)-3-(4-(trifluoromethoxy)phenyl)urea (50)

Intermediate 42 (303 mg, 1 mmol) was reacted with carboxylic acid 46 by Method E. Flash chromatography eluted with 9:1 DCM:MeOH afforded compound 50 (379 mg, 73%) as a white solid: Mp 178-183° C. $^1$H NMR (500 MHz, DMSO-d$_6$) δ 8.52 (s, 1H), 7.47 (d, J=8.9 Hz, 2H), 7.34-7.26 (m, 4H), 7.26-7.19 (m, 3H), 6.25 (d, J=7.5 Hz, 1H), 4.14 (d, J=13.4 Hz, 1H), 3.95 (d, J=12.5 Hz, 1H), 3.75-3.66 (m, 1H), 3.45 (s, 2H), 3.23 (d, J=13.2 Hz, 1H), 3.12 (t, J=11.9 Hz, 1H), 3.00 (d, J=13.1 Hz, 1H), 2.78 (t, J=11.6 Hz, 1H), 2.47-2.30 (m, 8H), 1.89-1.76 (m, 2H), 1.40-1.31 (m, 1H), 1.23-1.13 (m, 1H). Purity 90%. HRMS calculated for $C_{20}H_{21}F_3N_4O_3-H^+$ 518.2379. found (ESI(−), [M−H]) 518.2365.

1-(1-((4-Acetylpiperazin-1-yl)acetyl)piperidin-4-yl)-3-(4-(trifluoromethoxy)phenyl)urea (51)

Compound 50 (110 mg, 0.21 mmol) was deprotected by stirring overnight with 10% Pd/C in ethanol (15 mL) under a hydrogen atmosphere. The reaction was filtered through a bed of celite and the filtrate evaporated to give intermediate 1-(1-((piperazin-1-yl)acetyl)piperidin-4-yl)-3-(4-(trifluoromethoxy)phenyl)urea (103 mg, quantitative) as a clear oil, which was used without purification and coupled with acetic acid by Method E. Flash chromatography eluted with 9:1 DCM:MeOH and recrystallization from EtOAc:hexanes afforded compound 51 (73 mg, 74% over 2 steps) as a white solid: Mp 111-122° C. $^1$H NMR (500 MHz, DMSO-d$_6$) δ 8.52 (s, 1H), 7.47 (d, J=8.9 Hz, 2H), 7.22 (d, J=8.6 Hz, 2H), 6.25 (d, J=7.7 Hz, 1H), 4.15 (d, J=13.1 Hz, 1H), 3.92 (d, J=13.2 Hz, 1H), 3.76-3.67 (m, 1H), 3.47-3.38 (m, 4H), 3.25 (d, J=13.5 Hz, 1H), 3.12 (q, J=13.0 Hz, 2H), 2.81 (t, J=11.5 Hz, 1H), 2.37-2.32 (m, 2H), 1.98 (s, 3H), 2.44-2.40 (m, 2H), 1.90-1.77 (m, 2H), 1.42-1.31 (m, 1H), 1.26-1.15 (m, 1H). Purity 90%. HRMS calculated for $C_{20}H_{21}F_3N_4O_3-H^+$ 470.2015. found (ESI(−), [M−H]) 470.2009.

1-(1-(Cyclopropanecarbonyl)piperidin-4-yl)-3-(4-(trifluoromethoxy)phenyl) urea (52)

Intermediate 42 (76 mg, 0.25 mmol) was reacted with cyclopropane carboxylic acid by Method E. Flash chromatography eluted with EtOAc and recrystallization from EtOAc:hexane afforded compound 52 (47 mg, 51%) as a white solid: Mp 195-196° C. $^1$H NMR (500 MHz, DMSO-d$_6$) δ 8.56 (s, 1H), 7.47 (d, J=9.0 Hz, 2H), 7.22 (d, J=8.7 Hz, 2H), 6.25 (d, J=7.7 Hz, 1H), 4.15 (t, J=14.8 Hz, 2H), 3.77-3.68 (m, 1H), 3.25 (t, J=11.5 Hz, 1H, obscured), 2.81 (t, J=11.1 Hz, 1H), 1.98 (m, 1H), 1.93-1.75 (m, 2H), 1.41-1.17 (m, 2H), 0.75-0.65 (m, 4H). Purity 100%. HRMS calculated for $C_{17}H_{20}F_3N_3O_3+H^+$ 372.1535. found (ESI(+), [M+H]) 372.1546.

1-(1-(Trifluoroacetyl)piperidin-4-yl)-3-(4-(trifluoromethoxy)phenyl) urea (53)

Intermediate 42 (100 mg, 0.33 mmol) was dissolved in dry THF (1 mL), ethyl trifluoroacetate (30 μl 0.39 mmol) was added and the reaction was refluxed for 18 hours. The reaction was cooled to RT, evaporated and the residue chromatographed from EtOAc to give compound 53 (49 mg, 37%) as a white solid: Mp 150-154° C. $^1$H NMR (500 MHz, DMSO-d$_6$) δ 8.59 (s, 1H), 7.47 (d, J=9.0 Hz, 2H), 7.22 (d, J=8.6 Hz, 2H), 6.27 (d, J=7.6 Hz, 1H), 4.15 (d, J=13.1 Hz, 1H), 3.80 (d, J=11.1 Hz, 2H), 3.38 (t, J=11.9 Hz, 1H), 3.11 (t, J=12.1 Hz, 1H), 1.94 (t, J=15.2 Hz, 2H), 1.46-1.34 (m, 2H). Purity 100%. HRMS calculated for $C_{15}H_{15}F_6N_3O_3+H^+$ 400.1096. found (ESI(+), [M+H]) 400.1078.

1-(4-(Trifluoromethoxy)phenyl)-3-(1-(3,4,5-trihydroxybenzoyl)piperidin-4-yl)urea (54)

Intermediate 42 (152 mg, 0.5 mmol) was reacted with 44 by Method E. The reaction was diluted in ethyl acetate and washed with 1M NaOH, 1N HCl and finally water. The organic phase was dried and evaporated and the residue recrystallized from EtOAc:acetone to give intermediate 1-(4-(trifluoromethoxy)phenyl)-3-(1-(3,4,5-tris(benzyloxy)benzoyl)piperidin-4-yl)urea (304 mg, 84%). This intermediate (145 mg, 0.20 mmol) was hydrogenated in the same manner as for compound 51 and recrystallized from EtOAc:acetone to afford compound 54 (51 mg, 47% over 2 steps) as a white solid: Mp 168-175° C. $^1$H NMR (500 MHz, DMSO-d$_6$) δ 9.07 (s, 2H), 8.56 (s, 1H), 8.45 (s, 1H), 7.47 (d, J=9.0 Hz, 2H), 7.21 (d, J=9.0 Hz, 2H), 6.31 (s, 2H), 6.26 (d, J=7.6 Hz, 1H), 3.73 (s, 1H), 3.03 (s, 2H), 1.83 (d, J=9.6 Hz, 2H), 1.31 (dd, J=22.0, 11.9 Hz, 2H). Purity 94%. HRMS calculated for $C_{20}H_{20}F_3N_3O_6-H^+$ 454.1226. found (ESI(−), [M−H]) 454.1241.

1-(1-(Methylsulfonyl)piperidin-4-yl)-3-(4-(trifluoromethoxy)phenyl)urea (55)

Intermediate 42 (152 mg, 0.5 mmol) was reacted with methanesulfonyl chloride by Method E. Recrystallization from EtOAc:acetone afforded compound 55 (160 mg, 84%) as a white solid: Mp 233-234° C. $^1$H NMR (500 MHz, DMSO-d$_6$) δ 8.57 (s, 1H), 7.47 (d, J=9.0 Hz, 2H), 7.22 (d, J=8.6 Hz, 2H), 6.29 (d, J=7.5 Hz, 1H), 3.64-3.55 (m, 1H), 3.47 (d, J=12.2 Hz, 2H), 2.91-2.84 (m, 5H), 1.94-1.88 (m, 2H), 1.50-1.40 (m, 2H). Purity 98%. HRMS calculated for $C_{14}H_{18}F_3N_3O_4S-H^+$ 380.0892. found (ESI(−), [M−H]) 380.0931.

1-(1-(Ethylsulfonyl)piperidin-4-yl)-3-(4-(trifluoromethoxy)phenyl)urea (56)

The reaction of 42 with ethanesulfonyl chloride in the same manner as for compound 55 afforded compound 56 (122 mg, 62%): Mp 235-239° C. $^1$H NMR (500 MHz, DMSO-d$_6$) δ 8.56 (s, 1H), 7.47 (d, J=9.1 Hz, 2H), 7.22 (d, J=8.7 Hz, 2H), 6.29 (d, J=7.6 Hz, 1H), 3.66-3.58 (m, 1H), 3.52 (d, J=12.6 Hz, 2H), 3.05 (q, J=7.3 Hz, 2H), 3.00-2.93 (m, 2H), 1.89 (dd, J=12.8 Hz, 2H), 1.41 (dq, J=11.5, 4.0 Hz, 2H), 1.21 (t, J=7.3 Hz, 3H). Purity 100%. HRMS calculated for $C_{15}H_{20}F_3N_3O_4S+H^+$ 396.1205. found (ESI(+), [M+H]) 396.1179.

1-(1-(Phenylsulfonyl)piperidin-4-yl)-3-(4-(trifluoromethoxy)phenyl)urea (57)

The reaction of 42 with benzenesulfonyl chloride in the same manner as for compound 55 afforded compound 57 (183 mg, 82%): Mp 188-189° C. $^1$H NMR (500 MHz, DMSO-d$_6$) δ 8.45 (s, 1H), 7.80-7.61 (m, 4H), 7.41 (d, J=9.4 Hz, 2H), 7.19 (d, J=9.4 Hz, 2H), 6.21 (d, J=7.5 Hz, 1H), 3.55-3.39 (m, 3H), 2.54 (t, J=10.5 Hz, 2H), 1.92-1.80 (m, 2H), 1.35-1.53 (m, 2H). Purity 95%. HRMS calculated for $C_{19}H_{20}F_3N_3O_4S-H^+$ 442.1049. found (ESI(−), [M−H]) 442.1046.

1-(1-Tosylpiperidin-4-yl)-3-(4-(trifluoromethoxy)phenyl)urea (58)

The reaction of 42 with tosyl chloride in the same manner as for compound 55 afforded compound 58 (119 mg, 52%): Mp 205-207° C. $^1$H NMR (500 MHz, DMSO-d$_6$) δ 8.44 (s, 1H), 7.64 (d, J=8. Hz, 2H), 7.44 (dd, J=8. Hz, 4H), 7.18 (d, J=8. Hz, 2H), 6.18 (d, J=7. Hz, 1H), 3.52-3.45 (m, 1H), 3.41 (d, J=12. Hz, 2H), 2.56 (t, J=11. Hz, 2H), 2.42 (s, 3H), 1.87 (d, J=12. Hz, 2H), 1.45 (dd, J=10. Hz, 2H). Purity 95%. HRMS calculated for $C_{20}H_{22}F_3N_3O_4S-H^+$ 456.1205. found (ESI(−), [M−H]) 456.1247.

1-(1-(5-(Dimethylamino)naphthalen-1-ylsulfonyl) piperidin-4-yl)-3-(4-(trifluoromethoxy)phenyl)urea (59)

Intermediate 42 (200 mg, 0.7 mmol) was dissolved in DCM (7 mL) and triethylamine (100 µL, 0.7 mmol) added followed by 5-(dimethylamino)-1-naphthalenesulfonyl chloride (207 mg, 0.77 mmol). The reaction was evaporated, reconstituted in EtOAc and washed with 1N HCl and 1N $K_2CO_3$. Flash chromatography eluted with 2:1 EtOAc:hexanes afforded compound 59 (338 mg, 93%) as a tan solid: Mp 102-107° C. $^1$H NMR (500 MHz, DMSO-$d_6$ 8.52 (d, J=8.5 Hz, 1H), 8.45 (s, 1H), 8.28 (d, J=8.7 Hz, 1H), 8.14 (d, J=7.3 Hz, 1H), 7.67 (t, J=7.5 Hz, 1H), 7.62 (t, J=8.1 Hz, 1H), 7.43 (d, J=9.1 Hz, 2H), 7.28 (d, J=7.5 Hz, 1H), 7.19 (d, J=8.7 Hz, 2H), 6.24 (d, J=7.5 Hz, 1H), 3.60-3.53 (m, 3H), 2.88 (t, J=10.5 Hz, 2H, obscured by s δ 2.84), 2.84 (s, 6H), 1.84 (dd, J=12.9, 3.0 Hz, 2H), 1.38 (dq, J=10.6, 3.6 Hz, 2H). Purity 97%. HRMS calculated for $C_{25}H_{27}F_3N_4O_4S$+H$^+$ 537.1783. found (ESI(+), [M+H]) 537.1785.

Example 2

Synthesis of 1-(piperidin-4-yl)-3-(4-(trifluoromethyl) phenyl)urea (PTU)

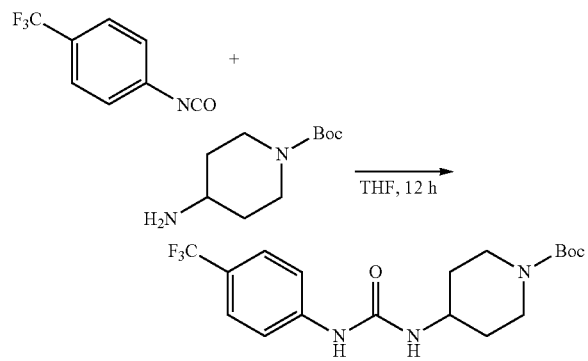

Synthesis of tert-butyl 4-(3-(4-(trifluoromethyl)phenyl) ureido)piperidine-1-carboxylate. 4-(Trifluoromethyl)phenyl isocyanate (1.068 g, 5.71 mmol) and 4-amino-1-Boc-piperidine (1.0 g, 5 mmol) was dissolved in THF (100 mL) and stirred for 12 h. The reaction was quenched by addition of water. The organic layer was isolated and the aqueous layer was extracted with EtOAc for 4 times. The combined organic layer was concentrated under vacuo and was further purified by flash chromatography (EtOAc:Hex/1:1) yielding final product (1.7 g, 4.39 mmol, 88%). $^1$H NMR ($d_6$-DMSO, 300 Mhz): ∂ 8.77 (s, 1H), 7.55 (s, 4H), 6.26 (d, J=10 Hz, 1H), 3.80 (d, J=Hz, 2H), 3.64 (m, 1H), 2.88 (br, 2H), 1.78 (d, J=5 Hz, 2H), 1.38 (s, 9H), 1.23 (m, 2H).

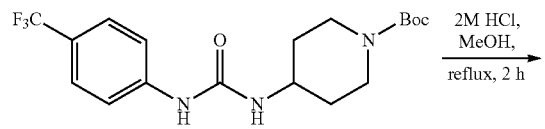

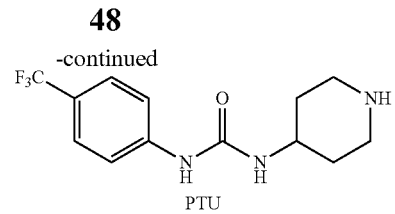

Synthesis of 1-(piperidin-4-yl)-3-(4-(trifluoromethyl)phenyl)urea (PTU). tert-butyl 4-(3-(4-(trifluoromethyl)phenyl) ureido)piperidine-1-carboxylate (1.6 g, 4.13 mmol) was dissolved in HCl solution (2M, MeOH, 100 mL). The resulting solution was refluxed for 2 h. The solvent was removed under vacuo and the crude was basified by NaOH solution (2N). The final precipitates (0.9 g, 3.13 mmol, 78%) were filtered and dried under high vacuum. The final product (PTU) was served as a scaffold for the following urea inhibitors synthesis. $^1$H NMR ($d_6$-DMSO, 300 Mhz): δ 8.77 (s, 1H), 7.57 (s, 4H), 6.30 (d, J=7.8 Hz, 1H), 3.55 (m, 1H), 2.91 (d, J=12.6 Hz, 2H), 2.48 (d, J=11.1 Hz, 2H), 1.77 (d, J=11 Hz, 2H), 1.22 (m, 2H)

Example 3

Synthesis of 1-(1-isobutyrylpiperidin-4-yl)-3-(4-(trifluoromethyl)phenyl)urea (60)

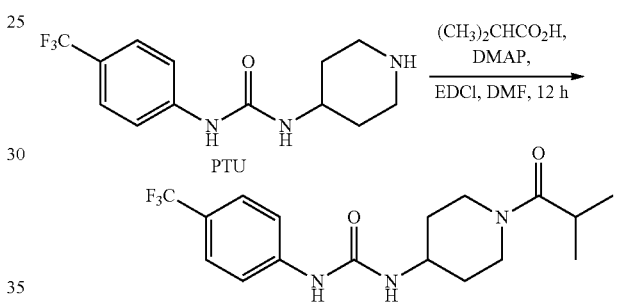

Isobutyric acid (37 mg, 0.418 mmol), DMAP (51 mg, 0.418 mmol) and EDCI (59 mg, 0.334 mmol) was dissolved in DMF (10 mL). PTU (80 mg, 0.278 mmol) was dissolved in DMF (5 mL) and was added into the reaction mixture dropwisely. The reaction mixture was stirred for 12 h and was quenched by addition of HCl solution (1M). The organic layer was collected and the aqueous layer was extracted with EtOAc for 4 times. The combined organic layer was concentrated under vacuo and further purified by flash chromatography (EtOAc:Hex/1:1) yielding final product (90 mg, 0.252 mmol, 90% yield). $^1$H NMR ($d_6$-DMSO, 300 Mhz): δ 8.79 (s, 1H), 7.57 (s, 4H), 6.38 (d, J=7.8 Hz, 1H), 4.25 (d, J=Hz, 1H), 3.85 (d, J=12.6 Hz, 1H), 3.75 (m, 1H), 3.18 (t, J=Hz, 1H), 2.85 (m, J=Hz, 1H), 2.79 (t, J=Hz, 1H), 1.85 (t, J=Hz, 2H), 1.25 (m, J=Hz, 2H), 0.98 (s, 6H).

Example 4

Synthesis of 1-(1-cyclopropanecarbonylpiperidin-4-yl)-3-(4-(trifluoromethyl)phenyl)urea (61)

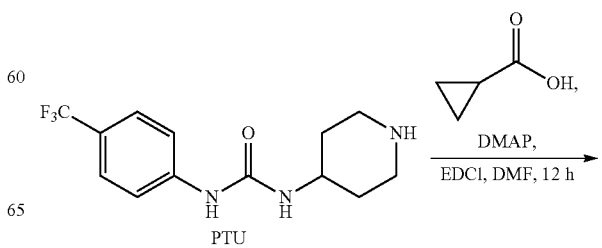

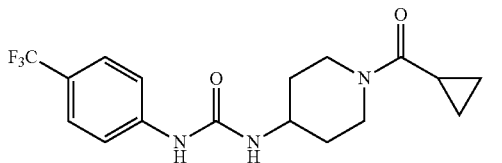

Cyclopropanecarboxylic acid (36 mg, 0.418 mmol) was reacted with PTU (100 mg, 0.348 mmol) as the same manner as the synthesis of 1-(1-isobutyrylpiperidin-4-yl)-3-(4-(trifluoromethyl)phenyl)urea yielding the final product (110 mg, 0.310 mmol, 89% yield). $^1$H NMR (d$_6$-DMSO, 300 Mhz): δ 8.80 (s, 1H), 7.57 (s, 4H), 6.37 (d, J=7.2 Hz, 1H), 4.16 (br, 2H), 3.74 (m, 1H), 3.25 (t, J=11.7 Hz, 1H), 2.81 (t, J=10.8 Hz, 1H), 1.98 (m, 1H), 1.85 (m, 2H), 1.30 (m, 2H), 0.7 (s, 4H).

Example 5

Synthesis of 1-(1-(3,3,3-trifluoropropionyl)piperidin-4-yl)-3-(4-(trifluoromethyl)phenyl)urea (62)

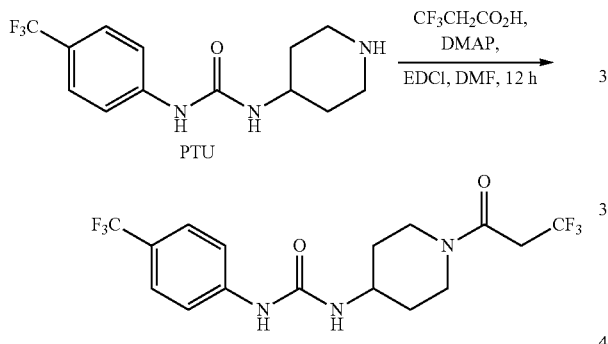

3,3,3-Trifluoropropionic acid (67 mg, 0.522 mmol) was reacted with PTU (100 mg, 0.348 mmol) as the same manner as the synthesis of 1-(1-isobutyrylpiperidin-4-yl)-3-(4-(trifluoromethyl)phenyl)urea yielding the final product (120 mg, 0.302 mmol, 87% yield). $^1$H NMR (d$_6$-DMSO, 300 Mhz): δ 8.80 (s, 1H), 7.58 (s, 4H), 6.38 (d, J=7.8 Hz, 1H), 4.19 (d, J=13.3 Hz, 1H), 3.79 (d, J=13.8 Hz, 1H), 3.71 (m, 4H), 3.16 (t, J=11.1 Hz, 1H), 2.85 (t, J=11.7 Hz, 1H), 1.84 (m, 2H), 1.30 (m, 2H).

Example 6

Synthesis of 1-(1-butyrylpiperidin-4-yl)-3-(4-(trifluoromethyl)phenyl)urea (63)

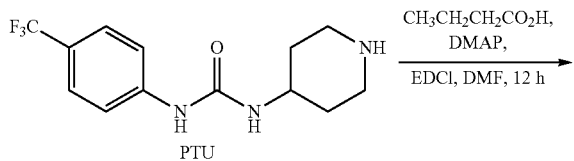

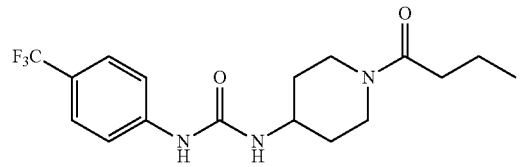

Butyric acid (37 mg, 0.418 mmol) was reacted with PTU (80 mg, 0.278 mmol) as the same manner as the synthesis of 1-(1-isobutyrylpiperidin-4-yl)-3-(4-(trifluoromethyl)phenyl)urea yielding the final product (91 mg, 0.255 mmol, 91% yield). $^1$H NMR (d$_6$-DMSO, 300 Mhz): δ 8.79 (s, 1H), 7.56 (s, 4H), 6.36 (d, J=7.8 Hz, 1H), 4.19 (d, J=12.9 Hz, 1H), 3.75 (d, J=14.4 Hz, 1H), 3.12 (t, J=11.4 Hz, 1H), 2.77 (m, J=12 Hz, 1H), 2.28 (t, J=7.5 Hz, 2H), 1.82 (t, J=13.2 Hz, 2H), 1.49 (m, 2H), 1.29 (m, 3H), 0.88 (t, J=7.5 Hz, 3H).

Example 7

Synthesis of 1-(1-(2-methylbutyryl)piperidin-4-yl)-3-(4-(trifluoromethyl)phenyl)urea (64)

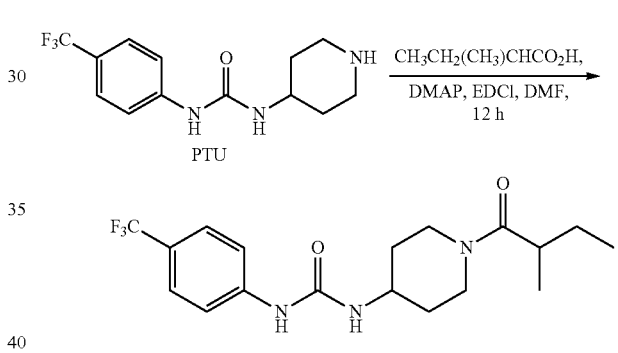

2-Methylbutyric acid (50 mg, 0.487 mmol) was reacted with PTU (70 mg, 0.244 mmol) as the same manner as the synthesis of 1-(1-isobutyrylpiperidin-4-yl)-3-(4-(trifluoromethyl)phenyl)urea yielding the final product (80 mg, 0.215 mmol, 88% yield). $^1$H NMR (d$_6$-DMSO, 300 Mhz): δ 8.77 (d, J=8.4 Hz, 1H), 7.57 (s, 4H), 6.37 (s, 1H), 4.22 (m, 1H), 3.88 (d, J=13.2 Hz, 1H), 3.71 (m, 1H), 3.17 (t, J=12.8 Hz, 1H), 2.84 (m, 2H), 1.85 (m, 2H), 1.54 (m, 1H), 1.29 (m, 3H), 0.97 (s, 3H), 0.81 (d, J=6 Hz, 3H).

Example 8

Synthesis of 1-(1-(4,4,4-trifluorobutyryl)piperidin-4-yl)-3-(4-(trifluoromethyl)phenyl)urea (65)

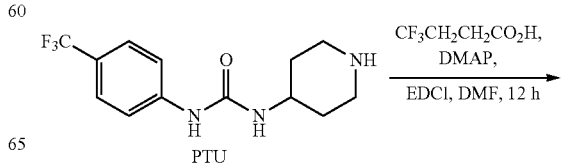

-continued

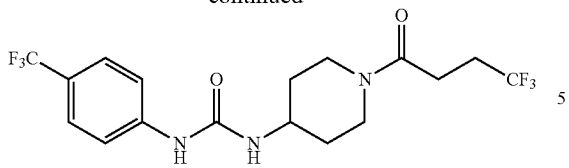

4,4,4-Trifluorobutanoic acid (59 mg, 0.418 mmol) was reacted with PTU (80 mg, 0.278 mmol) as the same manner as the synthesis of 1-(1-isobutyrylpiperidin-4-yl)-3-(4-(trifluoromethyl)phenyl)urea yielding the final product (80 mg, 0.194 mmol, 70% yield). $^1$H NMR (d$_6$-DMSO, 300 Mhz): δ 8.80 (s, 1H), 7.58 (s, 4H), 6.38 (d, J=7.8 Hz, 1H), 4.19 (d, J=13.8 Hz, 1H), 3.79 (d, J=13.8 Hz, 1H), 3.77 (m, 1H), 3.16 (t, J=12.3 Hz, 1H), 2.84 (m, J=11.4 Hz, 1H), 2.60 (d, J=6.3 Hz, 2H), 2.59 (m, 2H), 1.85 (br, 2H), 1.30 (m, 2H).

Example 9

Synthesis of 1-(1-(methylsulfonyl)piperidin-4-yl)-3-(4-(trifluoromethyl)phenyl)urea (66)

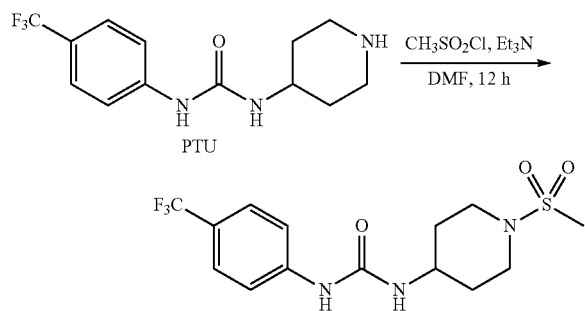

PTU (70 mg, 0.244 mmol) and Et$_3$N (30 mg, 0.292 mmol) was dissolved in DMF (10 mL) at 0° C. and methylsulfonyl chloride (56 mg, 0.487 mmol) was added into the reaction mixture dropwisely. The reaction mixture was stirred for 12 h at rt and was quenched by addition of HCl solution (1M). The organic layer was collected and the aqueous layer was extracted with EtOAc for 4 times. The combined organic layer was concentrated under vacuo and further purified by flash chromatography (EtOAc:Hex/6:4) yielding final product (45 mg, 0.123 mmol, 51% yield). $^1$H NMR (d$_6$-DMSO, 300 Mhz): δ 8.82 (s, 1H), 7.57 (s, 4H), 6.39 (d, J=7.5 Hz, 1H), 3.61 (m, 1H), 3.46 (d, J=12.3 Hz, 2H), 2.87 (s, 3H), 2.87 (m, 2H), 1.92 (d, J=9.9 Hz, 2H), 1.46 (m, 2H).

Example 10

Synthesis of 1-(1-(ethylsulfonyl)piperidin-4-yl)-3-(4-(trifluoromethyl)phenyl)urea (67)

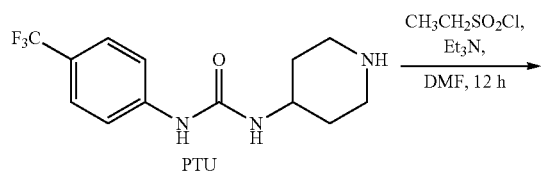

-continued

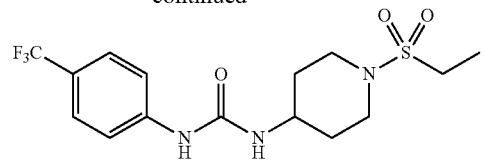

Ethylsulfonyl chloride (63 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (40 mg, 0.105 mmol, 43% yield). $^1$H NMR (d$_6$-DMSO, 300 Mhz): δ 8.77 (s, 1H), 7.57 (s, 4H), 6.38 (d, J=7.2 Hz, 1H), 3.63 (m, 1H), 3.52 (d, J=12.3 Hz, 2H), 3.05 (m, 5H), 1.89 (d, J=10 Hz, 2H), 1.47 (m, 2H), 1.22 (t, J=4.8 Hz, 3H).

Example 11

Synthesis of 1-(1-(propylsulfonyl)piperidin-4-yl)-3-(4-(trifluoromethyl)phenyl)urea (68)

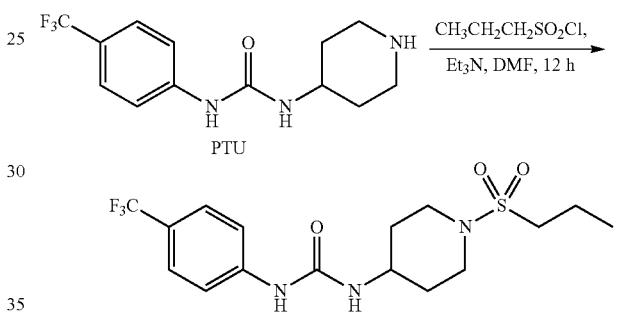

Propylsulfonyl chloride (70 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (60 mg, 0.153 mmol, 63% yield). $^1$H NMR (d$_6$-DMSO, 300 Mhz): δ 8.77 (s, 1H), 7.57 (s, 4H), 6.38 (d, J=7.5 Hz, 1H), 3.63 (m, 1H), 3.52 (d, J=12.4 Hz, 2H), 3.08 (m, 4H), 1.90 (d, J=9.6, 2H), 1.70 (m, 1H), 1.43 (m, 2H), 0.99 (t, J=7.2 Hz, 3H).

Example 12

Synthesis of 1-(1-(butylsulfonyl)piperidin-4-yl)-3-(4-(trifluoromethyl)phenyl)urea (69)

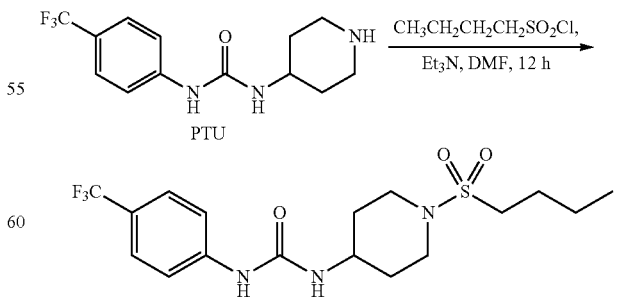

Butylsulfonyl chloride (76 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (65 mg, 0.160 mmol, 66% yield). ¹H NMR (d₆-DMSO, 300 Mhz): δ 8.78 (s, 1H), 7.57 (s, 4H), 6.38 (d, J=7.5 Hz, 1H), 4.19 (d, J=Hz, 1H), 3.82 (d, J=Hz, 1H), 3.73 (m, 1H), 3.18 (t, J=12.4 Hz, 1H), 2.82 (m, 1H), 2.78 (t, J=Hz, 1H), 1.80 (t, J=9.6, 2H), 1.43 (m, 2H), 0.97 (s, 6H).

Example 13

Synthesis of 1-(1-(cyclopropylsulfonyl)piperidin-4-yl)-3-(4-(trifluoromethyl)phenyl)urea (70)

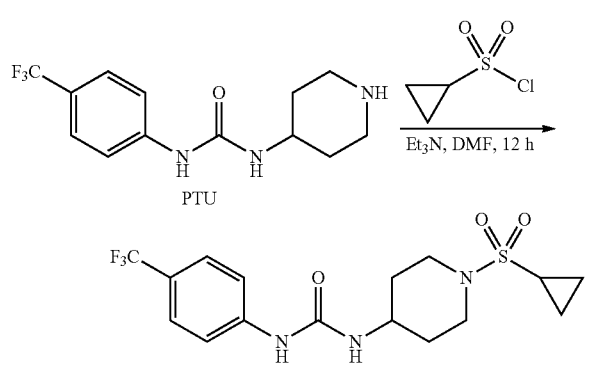

Cyclopropylsulfonyl chloride (68.5 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (65 mg, 0.166 mmol, 68% yield). ¹H NMR (d₆-DMSO, 300 Mhz): δ 8.78 (s, 1H), 7.57 (s, 4H), 6.38 (d, J=7.5 Hz, 1H), 4.19 (d, J=Hz, 1H), 3.52 (d, J=12.3 Hz, 2H), 2.99 (t, J=11.4 Hz, 2H), 2.58 (m, 1H), 1.91 (d, J=12.6 Hz, 2H), 1.46 (m, 2H), 0.96 (m, 4H).

Example 14

Synthesis of 1-(1-(isopropylsulfonyl)piperidin-4-yl)-3-(4-(trifluoromethyl)phenyl)urea (71)

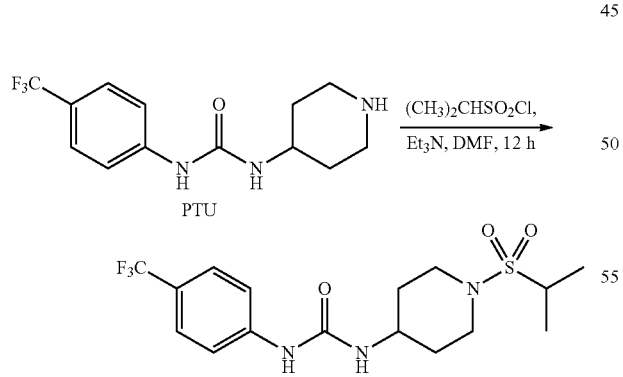

Isopropylsulfonyl chloride (70 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (80 mg, 0.203 mmol, 83% yield). ¹H NMR (d₆-DMSO, 300 Mhz): δ 8.78 (s, 1H), 7.57 (s, 4H), 6.38 (d, J=7.5 Hz, 1H), 4.19 (d, J=Hz, 1H), 3.82 (d, J=Hz, 1H), 3.73 (m, 1H), 3.18 (t, J=12.4 Hz, 1H), 2.82 (m, 1H), 2.78 (t, J=Hz, 1H), 1.80 (t, J=9.6, 2H), 1.43 (m, 2H), 0.97 (s, 6H).

Example 15

Synthesis of 1-(1-(2,2,2-trifluoroethylsulfonyl)piperidin-4-yl)-3-(4-(trifluoromethyl)phenyl)urea (72)

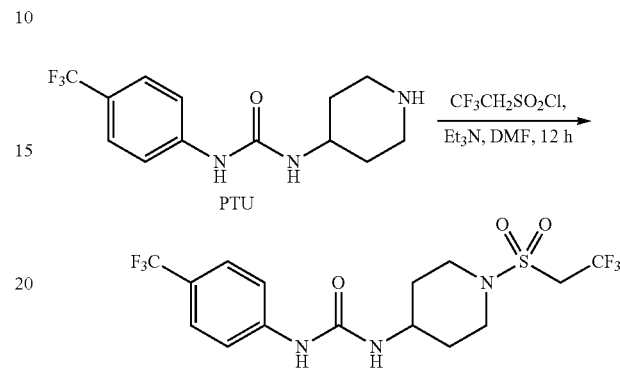

2,2,2-trifluoroethylsulfonyl chloride (89 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (48 mg, 0.111 mmol, 46% yield). ¹H NMR (d₆-DMSO, 300 Mhz): δ 8.81 (s, 1H), 7.56 (s, 4H), 6.41 (d, J=6.9 Hz, 1H), 4.51 (q, J=9.9 Hz, 2H), 3.58 (d, J=12 Hz, 1H), 3.58 (m, 1H), 3.02 (t, J=11.4 Hz, 2H), 1.92 (d, J=12.4 Hz, 2H), 1.45 (m, 2H).

Example 16

Synthesis of 1-(1-(3,3,3-trifluoropropylsulfonyl)piperidin-4-yl)-3-(4-(trifluoromethyl)phenyl) urea (73)

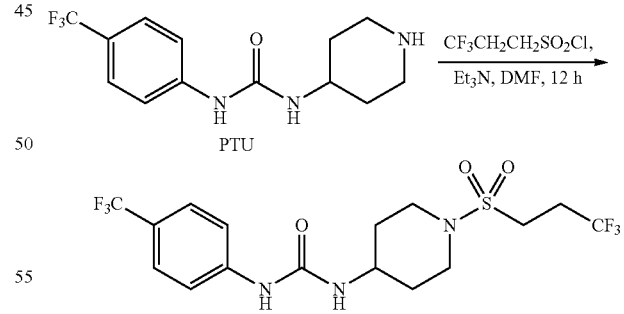

3,3,3-Trifluoropropylsulfonyl chloride (96 mg, 0.487 mmol) was reacted with PTU (70 mg, 0.244 mmol) as the same manner as the synthesis of 1-(1-(methylsulfonyl)piperidin-4-yl)-3-(4-(trifluoromethyl)phenyl)urea yielding the final product (55 mg, 0.123 mmol, 51% yield). ¹H NMR (d₆-DMSO, 300 Mhz): δ 8.78 (s, 1H), 7.57 (s, 4H), 6.38 (d, J=7.5 Hz, 1H), 4.19 (d, J=Hz, 1H), 3.82 (d, J=Hz, 1H), 3.73 (m, 1H), 3.18 (t, J=12.4 Hz, 1H), 2.82 (m, 1H), 2.78 (t, J=Hz, 1H), 1.80 (t, J=9.6, 2H), 1.43 (m, 2H), 0.97 (s, 6H).

Example 17

Synthesis of 1-(1-(cyclopropylsulfonyl)piperidin-4-yl)-3-(4-(trifluoromethyl)phenyl)urea (74)

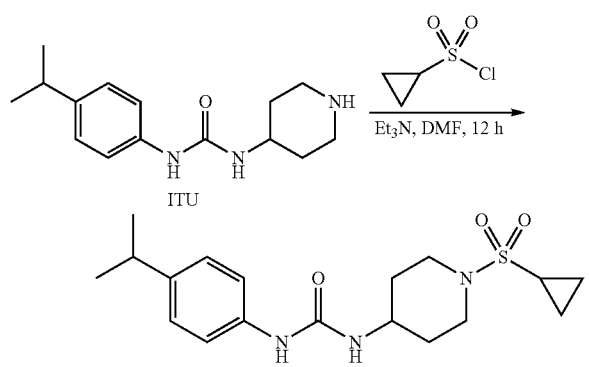

Cyclopropylsulfonyl chloride (75 mg, 0.536 mmol) was reacted with ITU (70 mg, 0.268 mmol) as the same manner as the synthesis of 1-(1-(methylsulfonyl)piperidin-4-yl)-3-(4-(trifluoromethyl)phenyl)urea yielding the final product (53 mg, 0.145 mmol, 54.1% yield). $^1$H NMR (d$_6$-DMSO, 300 Mhz): δ 8.20 (s, 1H), 7.26 (d, J=6.9 Hz, 2H), 7.07 (d, J=7.5 Hz, 2H), 6.14 (d, J=7.8 Hz, 1H), 3.59 (m, 1H), 3.52 (d, J=12.8 Hz, 2H), 2.98 (t, J=11.4 Hz, 2H), 2.79 (m, 1H), 2.57 (m, 1H), 1.90 (d, J=12.3 Hz, 2H), 1.42 (m, 2H), 1.15 (d, J=6.6 Hz, 6H), 0.95 (m, 4H).

Example 18

Pharmacokinetic Study

Enzyme Purification.

Recombinant murine and human sEH were produced in a polyhedron positive baculovirus expression system, and were purified by affinity chromatography as previously reported (*Arch. Biochem. Biophys.* 1993, 305, 197-201; *J. Biol. Chem.* 1993, 268, 17628-17633; *Anal. Biochem.* 1988, 169, 71-80).

IC$_{50}$ Assay Conditions.

IC$_{50}$ values were determined using a sensitive fluorescent based assay (*Anal. Biochem.* 2005, 343, 66-75). Cyano(2-methoxynaphthalen-6-yl)methyl trans-(3-phenyl-oxyran-2-yl)methyl carbonate (CMNPC) was used as the fluorescent substrate. Human sEH (1 nM) or murine sEH (1 nM) was incubated with the inhibitor for 5 min in pH 7.0 Bis-Tris/HCl buffer (25 mM) containing 0.1 mg/mL of BSA at 30° C. prior to substrate introduction ([S]=5 μM). Activity was determined by monitoring the appearance of 6-methoxy-2-naphthaldehyde over 10 minutes by fluorescence detection with an excitation wavelength of 330 nm and an emission wavelength of 465 nm. Reported IC$_{50}$ values are the average of three replicates. The fluorescent assay as performed here has a standard error between 10 and 20%, suggesting that differences of two-fold or greater are significant (*Anal. Biochem.* 2005, 343, 66-75).

Pharmacokinetics (PK) Study.

Male CFW mice (7 week old, 24-30 g) were purchased from Charles River Laboratories. All the experiments were performed according to protocols approved by the Animal Use and Care Committee of University of California, Davis. Inhibitors (1 mg each) were dissolved in 1 mL of oleic acid-rich triglyceride containing 20% polyethylene glycol (average molecular weight: 400) to give a clear solution for oral administration. Cassette 1 contained compounds 2, 24, 25, and 27. Cassette 2 contained compounds 12, 13, and 14. Cassette 3 contained compounds 3, 4 and AUDA. Cassette 4 contained compounds 2, 15, and 35. Each cassette was orally administered to 3 or 4 mice at a dose of 5 mg/kg in 120-150 μl of vehicle depending on animal weight. Blood (10 μL) was collected from the tail vein using a pipette tip rinsed with 7.5% EDTA(K3) at 0, 0.5, 1, 1.5, 2, 4, 6, 8, 24 hours after oral dosing with the inhibitor. The blood samples were prepared according to the methods detailed in our previous study (*Br. J. Pharmacol.* 2009, 156, 284-296). Blood samples were analyzed using an Agilent 1200 Series HPLC equipped with a 4.6 mm×150 mm Inertsil ODS-4 3 μm column (GL Science Inc., Japan) held at 40° C. and coupled with an Applied Biosystems 4000 QTRAP hybrid, triple-quadrupole mass spectrometer. The instrument was equipped with a linear ion trap and a Turbo V ion source and was operated in positive ion MRM mode (see Table 6). The solvent system consisted of water/acetic acid (999/1 v/v, solvent A) and acetonitrile/acetic acid (999/1 v/v; solvent B). The gradient was begun at 30% solvent B and was linearly increased to 100% solvent B in 5 min. This was maintained for 3 min, then returned to 30% solvent B in 2 min. The flow rate was 0.4 mL/min. The injection volume was 10 μL and the samples were kept at 4° C. in the auto sampler.

There is less than 5% variation in compound levels in replicate blood samples from the same mice. Thus the standard deviation shown in FIG. S2 represents variation among mice treated with the same compound. The PK parameters of individual mice were calculated by fitting the time dependent curve of blood inhibitor concentration (FIG. S2) to a non-compartmental analysis with the WinNonlin software (Pharsight, Mountain View, Calif.). Parameters determined include the time of maximum concentration (T$_{max}$), maximum concentration (C$_{max}$), half-life (t$_{1/2}$), and area under the concentration-time curve to terminal time (AUC$_t$). In separate studies to determine dose linearity of selected compounds, pharmacokinetic parameters determined by cassette dosing were found to be predictive of results from dosing individual compounds (*Br. J. Pharmacol.* 2009, 156, 284-296; *Anal. Chim. Acta.* 2006, 559, 37-44).

TABLE 1

Alkyl, carbocycle and unsubstituted aryl analogues

| Compd | R | IC$_{50}$ (nM)$^a$ Human | IC$_{50}$ (nM)$^a$ Murine | log P (±0.5) |
|---|---|---|---|---|
| 2 | (adamantyl) | 2.8 | 1.2 | 3.1 |

TABLE 1-continued

Alkyl, carbocycle and unsubstituted aryl analogues

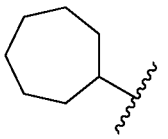 [SMILES: *C1CCCCCC1]

| Compd | R | IC$_{50}$ (nM)$^a$ Human | Murine | log P (±0.5) |
|---|---|---|---|---|
| 3 | 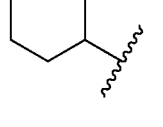 | 3.9 | 0.9 | 2.3 |
| 4 | 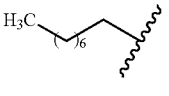 | 12 | 3.5 | 1.8 |
| 5 | 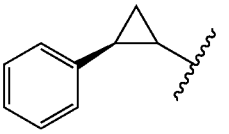 | 3.2 | 0.4 | 3.5 |
| 6 | 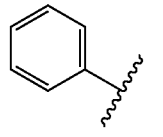 [SMILES: *c1ccccc1] | 2.7 | 7.4 | 1.8 |
| 7 | 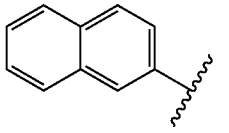 [SMILES: *c1ccc2ccccc2c1] | 130 | 49 | 1.3 |
| 8 | 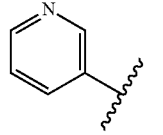 [SMILES: *c1cccnc1] | 3.0 | 4.2 | 2.4 |
| 9 | 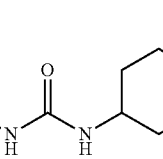 | 3,800 | >5,000 | nd$^b$ |

$^a$IC$_{50}$ values were determined with a fluorescent assay using homogenous recombinant murine and human enzymes (see methods) . . .
$^b$HPLC method used is limited to log P values greater than zero.

TABLE 2

Substituted phenyl analogues

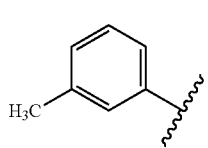 [SMILES: *c1cccc(C)c1]

| Compd | R | IC$_{50}$ (nM) Human | Murine | log P (±0.5) |
|---|---|---|---|---|
| 10 | 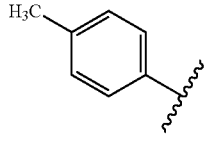 | 1,700 | >5,000 | 1.6 |
| 11 | 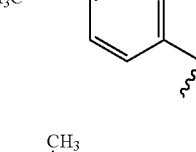 | 40 | 8.7 | 1.8 |
| 12 | 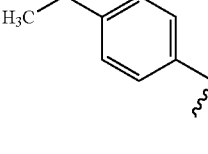 | 43 | 55 | 1.8 |
| 13 | 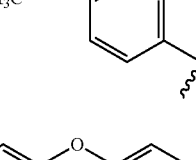 | 8.3 | 1.3 | 2.3 |
| 14 | 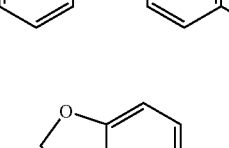 | 2.8 | 3.3 | 2.8 |
| 15 | 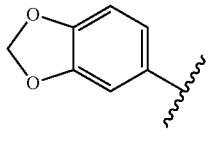 [SMILES: *c1ccc2c(c1)OCO2] | 87 | 8.7 | 1.0 |
| 16 |  | 3.5 | 0.4 | 2.8 |
| 17 |  | 61 | 100 | 1.1 |

TABLE 2-continued

Substituted phenyl analogues

[Structure: R-NH-C(=O)-NH-piperidine-N-C(=O)-CH2CH3]

| Compd | R | IC50 (nM) Human | IC50 (nM) Murine | log P (±0.5) |
|---|---|---|---|---|
| 18 | 3,4,5-trimethoxyphenyl | >5,000 | >5,000 | 0.8 |
| 19 | 4-morpholinophenyl | 2,000 | 650 | 0.2 |
| 20 | 4-nitrophenyl | 38 | 97 | 1.7 |
| 21 | 4-(methoxycarbonyl)phenyl | 140 | 64 | 1.6 |
| 22 | 4-carboxyphenyl | 330 | 1,000 | 0.4 |
| 23 | 4-hydroxyphenyl | 406 | 1,400 | 0.0 |

TABLE 3

Halophenyl urea analogues

[Structure: R-NH-C(=O)-NH-piperidine-N-C(=O)-CH2CH3]

| Compd | R | IC50 (nM) Human | IC50 (nM) Murine | log P (±0.5) |
|---|---|---|---|---|
| 24 | 4-fluorophenyl | 79 | 110 | 1.4 |
| 25 | 4-chlorophenyl | 10 | 23 | 2.2 |
| 26 | 4-bromophenyl | 3.6 | 15 | 2.4 |
| 27 | 4-iodophenyl | 7.2 | 1.4 | 2.5 |
| 28 | 3-fluorophenyl | 39 | 20 | 1.7 |
| 29 | 2-fluorophenyl | 300 | 780 | 1.6 |
| 30 | 3-chlorophenyl | 21 | 6.6 | 2.2 |
| 31 | 2-chlorophenyl | 1100 | 2900 | 2.0 |

TABLE 3-continued

Halophenyl urea analogues

| Compd | R | IC$_{50}$ (nM) Human | IC$_{50}$ (nM) Murine | log P (±0.5) |
|---|---|---|---|---|
| 32 | 3,4-diCl-phenyl | 3.4 | 0.6 | 2.9 |
| 33 | 3,5-diCl-phenyl | 0.4 | 1.0 | 3.3 |
| 34 | 2,6-diCl-phenyl | >5,000 | >5,000 | 1.3 |
| 35 | 4-Cl-3-CF$_3$-phenyl | 4.1 | 2.3 | 3.0 |
| 36 | 4-CF$_3$-phenyl | 0.7 | 6.5 | 2.4 |
| 37 | 3-CF$_3$-phenyl | 17 | 8.8 | 2.4 |
| 38 | 4-C(F)(CF$_3$)(CF$_3$)-phenyl | 0.4 | 0.7 | 3.5 |
| 39 | 4-C(F)(CF$_3$)(CF$_3$)-3-CH$_3$-phenyl | 17 | 28 | 3.8 |
| 40 | 4-OCF$_3$-phenyl | 3.7 | 2.8 | 2.5 |

TABLE 4

N-Acyl and N-sulfonyl piperidine analogues

| Compd | R$^2$ | IC$_{50}$ (nM) Human | IC$_{50}$ (nM) Murine | log P (±0.5) |
|---|---|---|---|---|
| 47 | 4-pyridinyl-C(O)- | 0.7 | 1.3 | 2.4 |
| 48 | 6-chloro-3-pyridinyl-C(O)- | 0.6 | 0.7 | 2.9 |
| 49 | 2-pyridinyl-CH$_2$-C(O)- | 3.1 | 5.0 | 2.6 |

TABLE 4-continued

N-Acyl and N-sulfonyl piperidine analogues

F₃CO–C₆H₄–NH–C(=O)–NH–(piperidine)–N–R²

| Compd | R² | IC₅₀ (nM) Human | IC₅₀ (nM) Murine | log P (±0.5) |
|---|---|---|---|---|
| 50 | –C(=O)CH₂–N(piperazine)N-Bn | 1.5 | 18 | 3.8 |
| 51 | –C(=O)CH₂–N(piperazine)N-C(=O)CH₃ | 0.5 | 1.2 | 2.4 |
| 52 | –C(=O)-cyclopropyl | 0.4 | 0.4 | 2.7 |
| 53 | –C(=O)CF₃ | 0.4 | 0.4 | 3.1 |
| 54 | –C(=O)–(3,4,5-trihydroxyphenyl) | 0.5 | 2.7 | 2.0 |
| 55 | –S(=O)₂CH₃ | 2.9 | 2.0 | 2.2 |
| 56 | –S(=O)₂CH₂CH₃ | 0.4 | 0.7 | 2.6 |
| 57 | –S(=O)₂–C₆H₅ | 1.8 | 0.4 | 3.1 |
| 58 | –S(=O)₂–(4-methylphenyl) | 0.4 | 0.4 | 3.5 |
| 59 | –S(=O)₂–(5-(dimethylamino)naphthalen-1-yl) | 0.8 | nd[a] | 4.3 |

[a] nd = Not determined

TABLE 5

Pharmacokinetic Screening Results[a]

| Compound | $C_{max}$ (nM) | $T_{max}$ (min) | $t_{1/2}$ (min) | $AUC_t$ (×10⁴ nM·min) |
|---|---|---|---|---|
| AUDA | 14 | 80 | 126 | 0.3 |
| 2 | 138 | 45 | 78 | 1.9 |
| 3 | 2,770 | 60 | 50 | 35 |
| 4 | 4,600 | 50 | 56 | 58 |
| 12 | 5,570 | 30 | 72 | 92 |
| 13 | 4,810 | 30 | 56 | 74 |
| 14 | 5,860 | 50 | 58 | 95 |
| 15 | 13,000 | 70 | 82 | 283 |
| 24 | 8,410 | 83 | 378 | 467 |
| 25 | 18,300 | 188 | 381 | 1,360 |
| 27 | 3,790 | 440 | 881 | 375 |
| 35 | 5,940 | 230 | 814 | 516 |

[a] Values are from single oral cassette dosing at 1 mg/kg in 120-150 μl of PEG400 in triglyceride

TABLE 6

Optimum mass spectrometer conditions and key fragmentation of the sEH inhibitors.

| Compound ID | Precursor ions m/z [M + H]⁺ | Predominant product ion m/z | DP (V) | CE (V) | CXP (V) |
|---|---|---|---|---|---|
| CUDA[a] | 341.2 | 216.2 | 76 | 25 | 10 |
| 2 | 334.2 | 157.1 | 51 | 15 | 6 |
| 3 | 296.1 | 157.1 | 51 | 21 | 8 |
| 4 | 282.1 | 157.1 | 61 | 19 | 12 |
| 12 | 290.1 | 183.1 | 56 | 19 | 14 |
| 13 | 304.4 | 122.1 | 56 | 29 | 6 |
| 14 | 318.1 | 183.1 | 51 | 21 | 14 |
| 15 | 305.8 | 84.1 | 51 | 55 | 4 |
| 24 | 293.7 | 183.1 | 31 | 19 | 8 |
| 25 | 310.0 | 183.0 | 66 | 21 | 16 |
| 27 | 402.1 | 183.1 | 77 | 19 | 12 |
| 35 | 378.1 | 183.1 | 66 | 23 | 12 |
| APAU[b] | 320.2 | 143.1 | 71 | 19 | 10 |
| AUDA | 393.2 | 135.1 | 81 | 37 | 10 |

[a] 12-(3-cyclohexan-1-yl-ureido)-dodecanoic acid (CUDA) was used as an internal standard to track instrument stability.
[b] 1-(1-acetypiperidin-4-yl)-3-adamantanylurea (APAU) was used as an internal standard added after thawing samples but before extraction to track the extraction efficiency of structurally similar target analytes.

TABLE 7

Cumulative table of inhibitor structures, results and properties.

| Compound ID | Structure | IC$_{50}$ (nM) Human | IC$_{50}$ (nM) Murine | log P (±0.5) | MP (°C.) | Synthetic Method(s) |
|---|---|---|---|---|---|---|
| 2 | | 2.8 | 1.2 | 3.1 | 201-221 | Ref. 12 |
| 3 | | 3.9 | 0.9 | 2.3 | 164-172 | B |
| 4 | | 12 | 3.5 | 1.8 | 177-179 | B |
| 5 | | 3.2 | 0.4 | 3.5 | 131-132 | A, B |
| 6 | | 2.7 | 7.4 | 1.8 | 155-158 | B |
| 7 | | 130 | 49 | 1.3 | 169-171 | B |
| 8 | | 3.0 | 4.2 | 2.4 | 213-215 | A, B |
| 9 | | 3,800 | 12,000 | <0 | Oil | B |

TABLE 7-continued

Cumulative table of inhibitor structures, results and properties.

| Compound ID | Structure | IC$_{50}$ (nM) Human | IC$_{50}$ (nM) Murine | log P (±0.5) | MP (° C.) | Synthetic Method(s) |
|---|---|---|---|---|---|---|
| 10 | 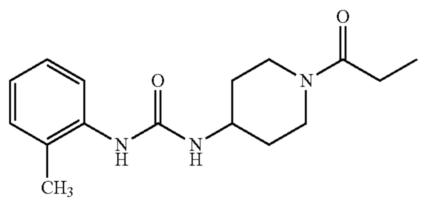 [SMILES: CCC(=O)N1CCC(NC(=O)Nc2ccccc2C)CC1] | 1,700 | 5,100 | 1.6 | 178-183 | A, B |
| 11 | 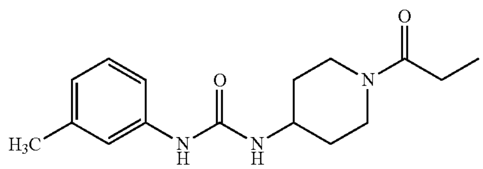 [SMILES: CCC(=O)N1CCC(NC(=O)Nc2cccc(C)c2)CC1] | 40 | 8.7 | 1.8 | 173-175 | A, B |
| 12 | 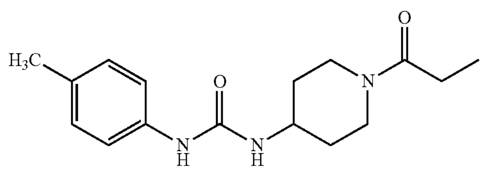 | 43 | 55 | 1.8 | 180-182 | A, B |
| 13 | 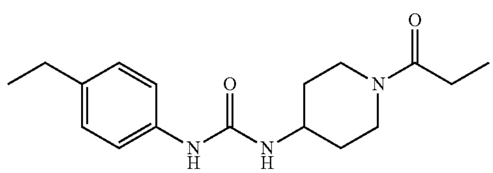 [SMILES: CCC(=O)N1CCC(NC(=O)Nc2ccc(CC)cc2)CC1] | 8.3 | 1.3 | 2.3 | 164-165 | A, B |
| 14 | 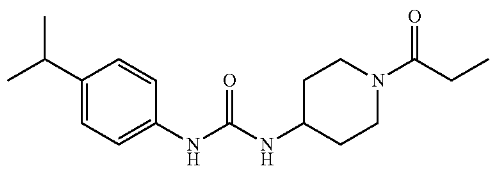 [SMILES: CCC(=O)N1CCC(NC(=O)Nc2ccc(C(C)C)cc2)CC1] | 2.8 | 3.3 | 2.8 | 173-174 | A, B |
| 15 | 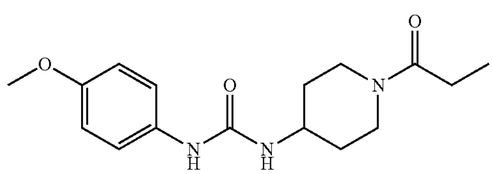 [SMILES: CCC(=O)N1CCC(NC(=O)Nc2ccc(OC)cc2)CC1] | 87 | 8.7 | 1.0 | 164-165 | A, B |
| 16 | 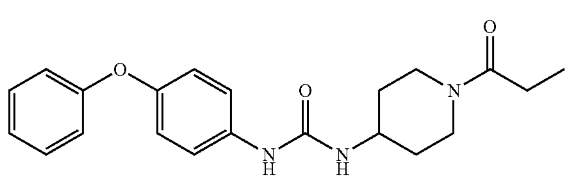 [SMILES: CCC(=O)N1CCC(NC(=O)Nc2ccc(Oc3ccccc3)cc2)CC1] | 3.5 | 0.4 | 2.8 | 153-154 | A, B |
| 17 | 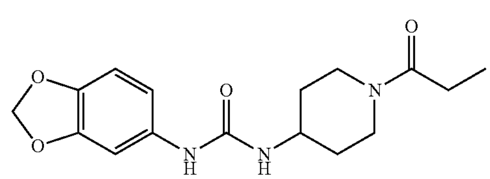 [SMILES: CCC(=O)N1CCC(NC(=O)Nc2ccc3c(c2)OCO3)CC1] | 61 | 100 | 1.1 | 195-197 | C |

TABLE 7-continued

Cumulative table of inhibitor structures, results and properties.

| Compound ID | Structure | IC$_{50}$ (nM) Human | IC$_{50}$ (nM) Murine | log P (±0.5) | MP (° C.) | Synthetic Method(s) |
|---|---|---|---|---|---|---|
| 18 | 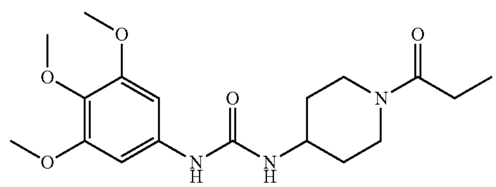 [SMILES: CCC(=O)N1CCC(NC(=O)Nc2cc(OC)c(OC)c(OC)c2)CC1] | >5,000 | 25,000 | 0.8 | 173-175 | A, B |
| 19 | 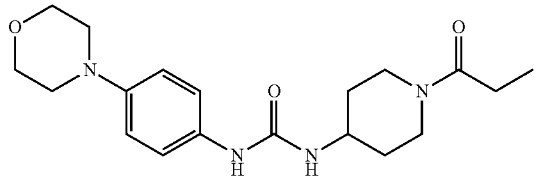 [SMILES: CCC(=O)N1CCC(NC(=O)Nc2ccc(N3CCOCC3)cc2)CC1] | 2,000 | 650 | 0.2 | 221-225 | A, B |
| 20 | 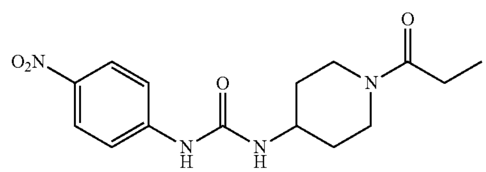 [SMILES: CCC(=O)N1CCC(NC(=O)Nc2ccc([N+](=O)[O-])cc2)CC1] | 38 | 97 | 1.7 | 240-241 | B |
| 21 | 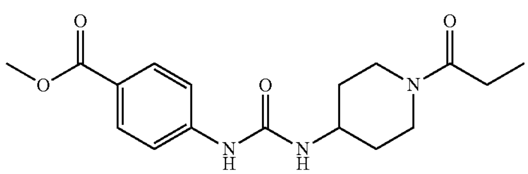 [SMILES: CCC(=O)N1CCC(NC(=O)Nc2ccc(C(=O)OC)cc2)CC1] | 140 | 64 | 1.6 | 192-204 | B |
| 22 | 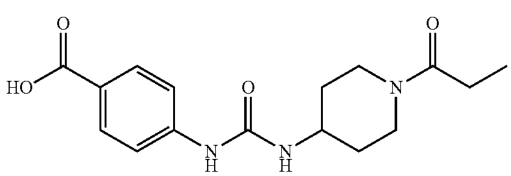 [SMILES: CCC(=O)N1CCC(NC(=O)Nc2ccc(C(=O)O)cc2)CC1] | 330 | 1,000 | 0.4 | 201-204 | From 21 |
| 23 | 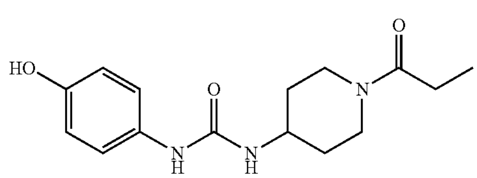 [SMILES: CCC(=O)N1CCC(NC(=O)Nc2ccc(O)cc2)CC1] | 15 | 1,400 | 0.0 | 229-230 | A, B |
| 24 | 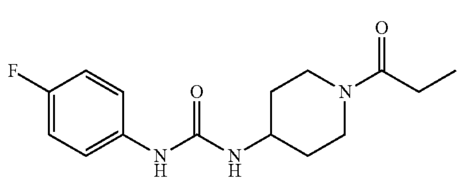 [SMILES: CCC(=O)N1CCC(NC(=O)Nc2ccc(F)cc2)CC1] | 79 | 110 | 1.4 | 183-184 | B |
| 25 | 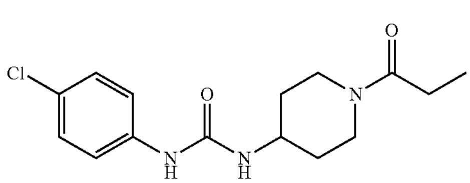 [SMILES: CCC(=O)N1CCC(NC(=O)Nc2ccc(Cl)cc2)CC1] | 10 | 23 | 2.2 | 225-226 | B |

TABLE 7-continued

Cumulative table of inhibitor structures, results and properties.

| Compound ID | Structure | IC₅₀ (nM) Human | IC₅₀ (nM) Murine | log P (±0.5) | MP (° C.) | Synthetic Method(s) |
|---|---|---|---|---|---|---|
| 26 | 4-Br-C₆H₄-NH-C(O)-NH-(piperidine-N-C(O)Et) | 3.6 | 15 | 2.4 | 233-239 | B |
| 27 | 4-I-C₆H₄-NH-C(O)-NH-(piperidine-N-C(O)Et) | 7.2 | 1.4 | 2.5 | 246-247 | A, B |
| 28 | 3-F-C₆H₄-NH-C(O)-NH-(piperidine-N-C(O)Et) | 39 | 20 | 1.7 | 158-164 | B |
| 29 | 2-F-C₆H₄-NH-C(O)-NH-(piperidine-N-C(O)Et) | 300 | 780 | 1.6 | 127-130 | B |
| 30 | 3-Cl-C₆H₄-NH-C(O)-NH-(piperidine-N-C(O)Et) | 21 | 6.6 | 2.2 | 165-166 | B |
| 31 | 2-Cl-C₆H₄-NH-C(O)-NH-(piperidine-N-C(O)Et) | 1100 | 2900 | 2.0 | 150-157 | C |
| 32 | 3,4-diCl-C₆H₃-NH-C(O)-NH-(piperidine-N-C(O)Et) | 3.4 | 0.6 | 2.9 | 198-200 | A, B |
| 33 | 3,5-diCl-C₆H₃-NH-C(O)-NH-(piperidine-N-C(O)Et) | 0.4 | 1.0 | 3.3 | 196-198 | A, B |

TABLE 7-continued

Cumulative table of inhibitor structures, results and properties.

| Compound ID | Structure | IC$_{50}$ (nM) Human | IC$_{50}$ (nM) Murine | log P (±0.5) | MP (° C.) | Synthetic Method(s) |
|---|---|---|---|---|---|---|
| 34 | 2,6-dichlorophenyl urea piperidine propionyl | >50,000 | 38,000 | 1.3 | 170-174 | B |
| 35 | 4-chloro-3-trifluoromethylphenyl urea piperidine propionyl | 4.1 | 2.3 | 3.0 | 182-184 | B |
| 36 | 4-trifluoromethylphenyl urea piperidine propionyl | 0.7 | 6.5 | 2.4 | 224-228 | B |
| 37 | 3-trifluoromethylphenyl urea piperidine propionyl | 17 | 8.8 | 2.4 | 153-154 | B |
| 38 | 4-(perfluoro-isopropyl)phenyl urea piperidine propionyl | 0.4 | 0.7 | 3.5 | 160-164 | A, B |
| 39 | 4-(perfluoro-isopropyl)-2-methylphenyl urea piperidine propionyl | 17 | 28 | 3.8 | 226-229 | A, B |
| 40 | 4-trifluoromethoxyphenyl urea piperidine propionyl | 3.7 | 2.8 | 2.5 | 195-196 | B |
| 47 | 4-trifluoromethoxyphenyl urea piperidine isonicotinoyl | 0.7 | 1.3 | 2.4 | 210-212 | D |

TABLE 7-continued

Cumulative table of inhibitor structures, results and properties.

| Compound ID | Structure | IC$_{50}$ (nM) Human | Murine | log P (±0.5) | MP (° C.) | Synthetic Method(s) |
|---|---|---|---|---|---|---|
| 48 | 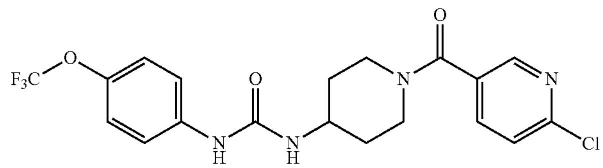 [SMILES: O=C(Nc1ccc(OC(F)(F)F)cc1)NC1CCN(C(=O)c2ccc(Cl)nc2)CC1] | 0.6 | 0.7 | 2.9 | 208-209 | D |
| 49 | 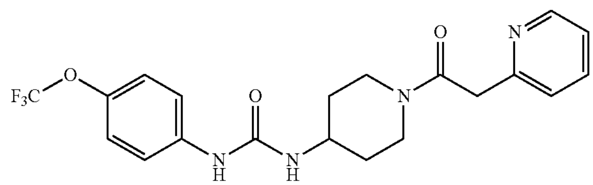 [SMILES: O=C(Nc1ccc(OC(F)(F)F)cc1)NC1CCN(C(=O)Cc2ccccn2)CC1] | 3.1 | 5.0 | 2.6 | 183-187 | D |
| 50 | 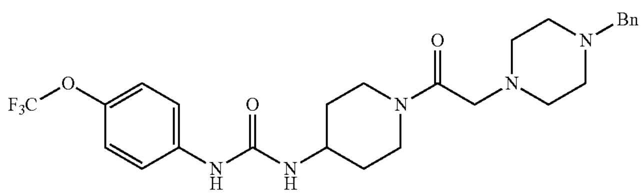 [SMILES: O=C(Nc1ccc(OC(F)(F)F)cc1)NC1CCN(C(=O)CN2CCN(Cc3ccccc3)CC2)CC1] | 1.5 | 18 | 3.8 | 178-183 | D |
| 51 | 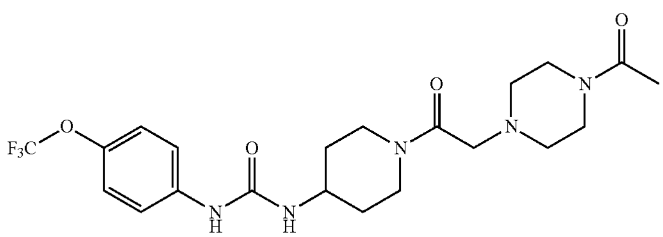 [SMILES: CC(=O)N1CCN(CC(=O)N2CCC(NC(=O)Nc3ccc(OC(F)(F)F)cc3)CC2)CC1] | 0.5 | 1.2 | 2.4 | 111-122 | From 50 |
| 52 | 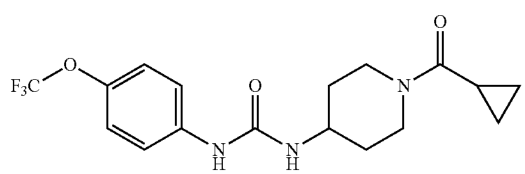 [SMILES: O=C(Nc1ccc(OC(F)(F)F)cc1)NC1CCN(C(=O)C2CC2)CC1] | 0.4 | 0.4 | 2.7 | 195-196 | D |
| 53 | 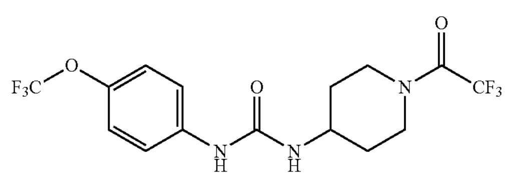 [SMILES: O=C(Nc1ccc(OC(F)(F)F)cc1)NC1CCN(C(=O)C(F)(F)F)CC1] | 0.4 | 0.4 | 3.1 | 150-154 | See text |
| 54 | 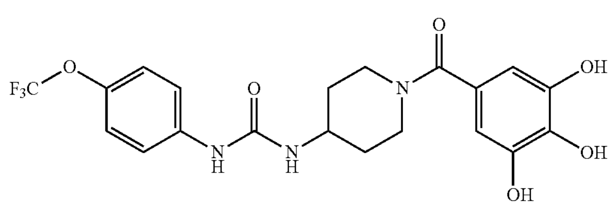 [SMILES: O=C(Nc1ccc(OC(F)(F)F)cc1)NC1CCN(C(=O)c2cc(O)c(O)c(O)c2)CC1] | 0.5 | 2.7 | 2.0 | 168-175 | D |
| 55 | 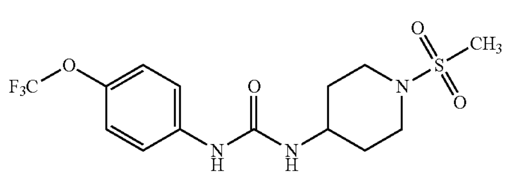 [SMILES: CS(=O)(=O)N1CCC(NC(=O)Nc2ccc(OC(F)(F)F)cc2)CC1] | 2.9 | 2.0 | 2.2 | 233-234 | E |

TABLE 7-continued

Cumulative table of inhibitor structures, results and properties.

| Compound ID | Structure | IC$_{50}$ (nM) Human | IC$_{50}$ (nM) Murine | log P (±0.5) | MP (° C.) | Synthetic Method(s) |
|---|---|---|---|---|---|---|
| 56 | F$_3$CO-C$_6$H$_4$-NH-C(O)-NH-piperidine-N-SO$_2$-Et | 0.4 | 0.7 | 2.6 | 235-239 | E |
| 57 | F$_3$CO-C$_6$H$_4$-NH-C(O)-NH-piperidine-N-SO$_2$-Ph | 1.8 | 0.4 | 3.1 | 188-159 | E |
| 58 | F$_3$CO-C$_6$H$_4$-NH-C(O)-NH-piperidine-N-SO$_2$-C$_6$H$_4$-CH$_3$ | 0.4 | 0.4 | 3.5 | 205-207 | E |
| 59 | F$_3$CO-C$_6$H$_4$-NH-C(O)-NH-piperidine-N-SO$_2$-(5-dimethylamino-naphthalenyl) | 0.8 | nd[a] | 4.3 | 102-107 | E |

[a] nd = Not Determined

TABLE 8

Haloalkyl-Phenyl Ureas

| Compound | Structure | Name | IC$_{50}$ (FA[1]) | IC$_{50}$ (tDPPO[2]) |
|---|---|---|---|---|
| 36 | F$_3$C-C$_6$H$_4$-NH-C(O)-NH-piperidine-N-C(O)-Et | 1-(1-propionoylpiperidin-4-yl)-3-(4-(trifluoromethyl)phenyl)urea | 9.3 | 89.6 |
| 60 | F$_3$C-C$_6$H$_4$-NH-C(O)-NH-piperidine-N-C(O)-CH(CH$_3$)$_2$ | 1-(1-isobutyrylpiperidin-4-yl)-3-(4-(trifluoromethyl)phenyl)urea | 5.5 | 37.5 |

TABLE 8-continued

Haloalkyl-Phenyl Ureas

| Compound | Structure | Name | IC$_{50}$ (FA[1]) | IC$_{50}$ (tDPPO[2]) |
|---|---|---|---|---|
| 61 | 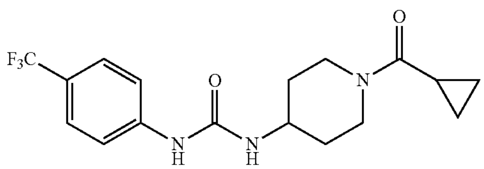 [SMILES: O=C(Nc1ccc(C(F)(F)F)cc1)NC1CCN(C(=O)C2CC2)CC1] | 1-(1-(cyclopropanecarbonyl)piperidin-4-yl)-3-(4-(trifluoromethyl)phenyl)urea | 1.7 | 22.6 |
| 62 | 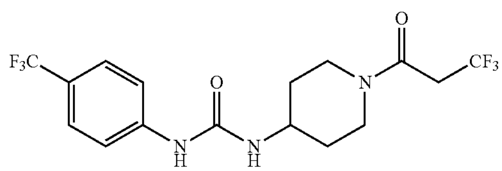 [SMILES: O=C(Nc1ccc(C(F)(F)F)cc1)NC1CCN(C(=O)CC(F)(F)F)CC1] | 1-(4-(trifluoromethyl)phenyl)-3-(1-(3,3,3-trifluoropropionoyl)piperidin-4-yl)urea | 1.5 | 9.1 |
| 63 | 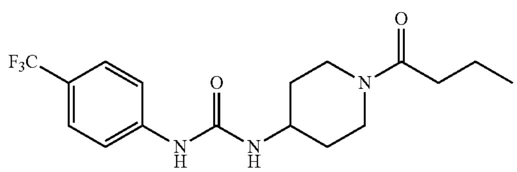 [SMILES: CCCC(=O)N1CCC(NC(=O)Nc2ccc(C(F)(F)F)cc2)CC1] | 1-(1-butyrylpiperidin-4-yl)-3-(4-(trifluoromethyl)phenyl)urea | 7.9 | 63.8 |
| 64 | 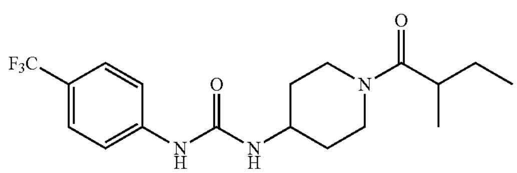 [SMILES: CCC(C)C(=O)N1CCC(NC(=O)Nc2ccc(C(F)(F)F)cc2)CC1] | 1-(1-(2-methylbutanoyl)piperidin-4-yl)-3-(4-(trifluoromethyl)phenyl)urea | 4 | 17.8 |
| 65 | 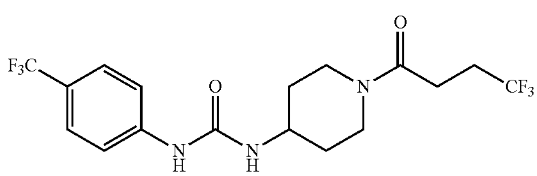 [SMILES: O=C(Nc1ccc(C(F)(F)F)cc1)NC1CCN(C(=O)CCC(F)(F)F)CC1] | 1-(1-(4,4,4-trifluorobutanoyl)piperidin-4-yl)-3-(4-(trifluoromethyl)phenyl)urea | 9.3 | 70.8 |
| 66 | 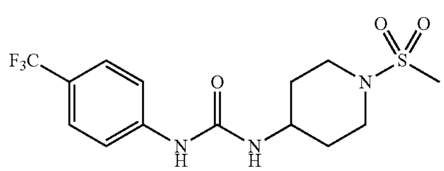 [SMILES: CS(=O)(=O)N1CCC(NC(=O)Nc2ccc(C(F)(F)F)cc2)CC1] | 1-(1-(methylsulfonyl)piperidin-4-yl)-3-(4-(trifluoromethyl)phenyl)urea | 28.9 | 148.0 |
| 67 | 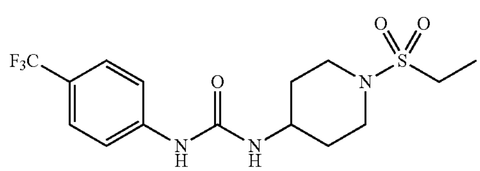 [SMILES: CCS(=O)(=O)N1CCC(NC(=O)Nc2ccc(C(F)(F)F)cc2)CC1] | 1-(1-(ethylsulfonyl)piperidin-4-yl)-3-(4-(trifluoromethyl)phenyl)urea | 11.0 | 93.9 |
| 68 | 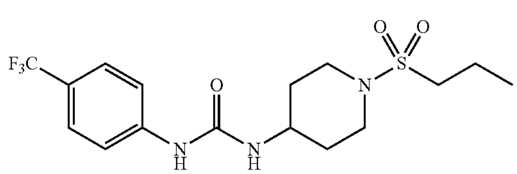 [SMILES: CCCS(=O)(=O)N1CCC(NC(=O)Nc2ccc(C(F)(F)F)cc2)CC1] | 1-(1-(propylsulfonyl)piperidin-4-yl)-3-(4-(trifluoromethyl)phenyl)urea | 6.0 | 45.4 |

TABLE 8-continued

Haloalkyl-Phenyl Ureas

| Compound | Structure | Name | IC$_{50}$ (FA[1]) | IC$_{50}$ (tDPPO[2]) |
|---|---|---|---|---|
| 69 | 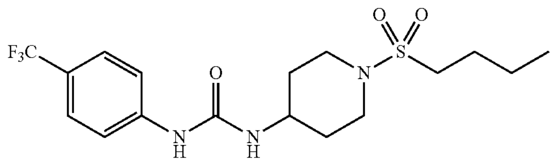 [SMILES: CCCCS(=O)(=O)N1CCC(NC(=O)Nc2ccc(C(F)(F)F)cc2)CC1] | 1-(1-(butylsulfonyl)piperidin-4-yl)-3-(4-(trifluoromethyl)phenyl)urea | 6.8 | 27.0 |
| 70 | 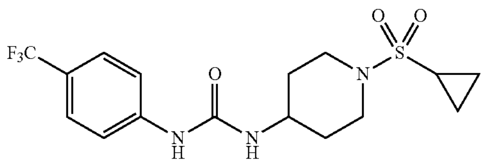 [SMILES: O=C(Nc1ccc(C(F)(F)F)cc1)NC1CCN(S(=O)(=O)C2CC2)CC1] | 1-(1-(cyclopropylsulfonyl)piperidin-4-yl)-3-(4-(trifluoromethyl)phenyl)urea | 9.3 | 92.1 |
| 71 | 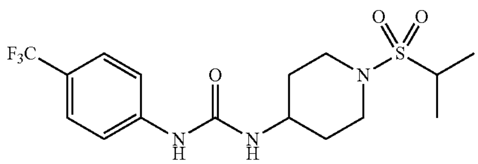 [SMILES: CC(C)S(=O)(=O)N1CCC(NC(=O)Nc2ccc(C(F)(F)F)cc2)CC1] | 1-(1-(isopropylsulfonyl)piperidin-4-yl)-3-(4-(trifluoromethyl)phenyl)urea | 10.1 | 37.5 |
| 72 | 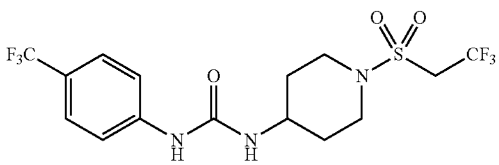 [SMILES: O=C(Nc1ccc(C(F)(F)F)cc1)NC1CCN(S(=O)(=O)CC(F)(F)F)CC1] | 1-(1-((2,2,2-trifluoroethyl)sulfonyl)piperidin-4-yl)-3-(4-(trifluoromethyl)phenyl)urea | 3.6 | 23.6 |
| 73 | 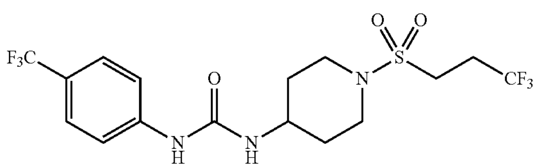 [SMILES: O=C(Nc1ccc(C(F)(F)F)cc1)NC1CCN(S(=O)(=O)CCC(F)(F)F)CC1] | 1-(1-((3,3,3-trifluoropropyl)sulfonyl)piperidin-4-yl)-3-(4-(trifluoromethyl)phenyl)urea | | |
| 74 | 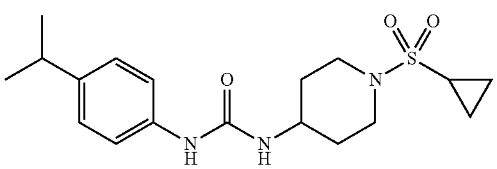 [SMILES: CC(C)c1ccc(NC(=O)NC2CCN(S(=O)(=O)C3CC3)CC2)cc1] | 1-(1-(cyclopropylsulfonyl)piperidin-4-yl)-3-(4-isopropylphenyl)urea | 14.3 | 157.4 |

[1]FA is fluoresence competitive assay.
[2]t-DPPO is trans-diphenylpropene oxide, used in a radiometric competitive assay.

TABLE 9

Pharmacokinetic Screening Results for Selected Haloalkyl-Phenyl Ureas

| Inhibitors | Tmax (h) | Cmax(uM) | T1/2 (h) | AUC(uM*h) |
|---|---|---|---|---|
| A (61) | 4 | 10.2 | 10.6 | 170 |
| B (70) | 4 | 10.9 | 11.9 | 167 |
| C (69) | 1 | 1.7 | 4.5 | 15.5 |
| D (64) | 4 | 4.0 | 2.5 | 3.9 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound, the compound being 1-(1-cyclopropanecarbonylpiperidin-4-yl)-3-(4-(trifluoromethyl)phenyl)urea, or salts and isomers thereof.

2. A pharmaceutical composition comprising a compound of claim 1 and a pharmaceutically acceptable excipient.

* * * * *